US010806532B2

(12) United States Patent
Grubbs et al.

(10) Patent No.: US 10,806,532 B2
(45) Date of Patent: Oct. 20, 2020

(54) SURGICAL SIMULATION SYSTEM USING FORCE SENSING AND OPTICAL TRACKING AND ROBOTIC SURGERY SYSTEM

(71) Applicant: KINDHEART, INC., Chapel Hill, NC (US)

(72) Inventors: W. Andrew Grubbs, Chapel Hill, NC (US); Samuel D. Drew, Chapel Hill, NC (US)

(73) Assignee: KINDHEART, INC., Chapel Hill, NC (US)

(*) Notice: Subject to any disclaimer, the term of this patent is extended or adjusted under 35 U.S.C. 154(b) by 320 days.

(21) Appl. No.: 15/956,801

(22) Filed: Apr. 19, 2018

(65) Prior Publication Data

US 2018/0338806 A1 Nov. 29, 2018

Related U.S. Application Data

(60) Provisional application No. 62/567,946, filed on Oct. 4, 2017, provisional application No. 62/532,470, filed
(Continued)

(51) Int. Cl.
*G09B 23/28* (2006.01)
*A61B 34/35* (2016.01)
(Continued)

(52) U.S. Cl.
CPC .............. *A61B 34/35* (2016.02); *A61B 34/10* (2016.02); *A61B 34/30* (2016.02); *G06T 19/003* (2013.01);
(Continued)

(58) Field of Classification Search
CPC ......... A61B 34/35; A61B 34/30; A61B 34/10; A61B 18/00; A61B 2090/064;
(Continued)

(56) References Cited

U.S. PATENT DOCUMENTS 5,765,561 A * 6/1998 Chen ...................... G09B 23/28
348/77
5,792,135 A 8/1998 Madhani et al.
(Continued)

OTHER PUBLICATIONS

A. Simon Turner, "Experiences with Sheep as an Animal Model for Shoulder Surgery: Strengths and Shortcomings," Journal of Shoulder and Elbow Surgery, vol. 16, Issue 5, Supplement, Sep.-Oct. 2007, pp. 158S-163S.
(Continued)

*Primary Examiner* — Michael C Grant
(74) *Attorney, Agent, or Firm* — Allen, Dyer, Doppelt + Gilchrist, P.A.

(57) ABSTRACT

A surgical simulation device includes a support structure and animal tissue carried in a tray. A simulated human skeleton is carried by the support structure above the animal tissue and includes simulated human skin. A camera images the animal tissue and an image processor receives images of markers positioned on the ribs and animal tissue and forms a three-dimensional wireframe image. An operating table is adjacent a local robotic surgery station as part of a robotic surgery station and includes at least one patient support configured to support the patient during robotic surgery. At least one patient force/torque sensor is coupled to the at least one patient support and configured to sense at least one of force and torque experienced by the patient during robotic surgery.

10 Claims, 29 Drawing Sheets

Related U.S. Application Data on Jul. 14, 2017, provisional application No. 62/512,933, filed on May 31, 2017, provisional application No. 62/510,494, filed on May 24, 2017.

(51) Int. Cl.
| | | |
|---|---|---|
| *A61B 34/10* | (2016.01) | |
| *G06T 19/00* | (2011.01) | |
| *A61B 34/30* | (2016.01) | |
| *A61B 18/00* | (2006.01) | |
| *A61B 90/00* | (2016.01) | |
| *A61B 34/20* | (2016.01) | |

(52) U.S. Cl.
CPC ............ *G09B 23/285* (2013.01); *A61B 18/00* (2013.01); *A61B 2034/101* (2016.02); *A61B 2034/2055* (2016.02); *A61B 2034/2065* (2016.02); *A61B 2090/064* (2016.02); *A61B 2090/066* (2016.02); *A61B 2090/365* (2016.02); *A61B 2090/368* (2016.02); *A61B 2090/3937* (2016.02); *A61B 2090/3941* (2016.02); *G06T 2207/30061* (2013.01); *G06T 2210/41* (2013.01)

(58) Field of Classification Search
CPC ...... A61B 2034/2065; A61B 2090/365; A61B 2090/368; A61B 2090/066; A61B 2090/3941; A61B 2034/2055; A61B 2090/3937; A61B 2034/101; G09B 23/285; G06T 19/003; G06T 2210/41; G06T 2207/30061
USPC ........................................................ 434/262
See application file for complete search history.

(56) References Cited

U.S. PATENT DOCUMENTS

| | | | |
|---|---|---|---|
| 5,817,084 A | 10/1998 | Jensen | |
| 6,331,181 B1 | 12/2001 | Tierney et al. | |
| 6,428,323 B1 | 8/2002 | Pugh | |
| 6,441,577 B2 | 8/2002 | Blumenkranz et al. | |
| 6,491,701 B2 | 12/2002 | Tierney et al. | |
| 6,538,791 B2 | 3/2003 | Trezza | |
| 6,659,939 B2 | 12/2003 | Moll et al. | |
| 6,693,712 B1 | 2/2004 | Trezza | |
| 6,817,974 B2 | 11/2004 | Cooper et al. | |
| 7,784,126 B2 | 8/2010 | Meissner et al. | |
| 7,798,815 B2 | 9/2010 | Ramphal et al. | |
| 7,963,913 B2 | 6/2011 | Devengenzo et al. | |
| 8,684,914 B2 | 4/2014 | McDowall et al. | |
| 8,706,184 B2 | 4/2014 | Mohr et al. | |
| 8,764,450 B2 | 7/2014 | Pugh | |
| 8,810,631 B2 | 8/2014 | Scott et al. | |
| 9,037,215 B2 | 5/2015 | Higgins et al. | |
| 9,254,090 B2 | 2/2016 | Watson et al. | |
| 9,342,997 B2 | 5/2016 | Feins et al. | |
| D773,686 S | 12/2016 | Moore | |
| 9,687,301 B2 | 6/2017 | Lee et al. | |
| 9,805,625 B2 | 10/2017 | Feins et al. | |
| 2003/0031993 A1 | 2/2003 | Pugh | |
| 2005/0064378 A1* | 3/2005 | Toly | G09B 23/285 434/262 |
| 2005/0084833 A1* | 4/2005 | Lacey | G09B 23/285 434/262 |
| 2006/0258938 A1 | 11/2006 | Hoffman | |
| 2009/0208915 A1 | 8/2009 | Pugh | |
| 2009/0305215 A1* | 12/2009 | Wilkins | G09B 23/28 434/274 |
| 2010/0035222 A1* | 2/2010 | Kukora | G09B 23/28 434/262 |
| 2010/0167249 A1* | 7/2010 | Ryan | G09B 23/285 434/267 |
| 2010/0167250 A1* | 7/2010 | Ryan | G09B 23/285 434/267 |
| 2010/0167253 A1* | 7/2010 | Ryan | G09B 23/30 434/272 |
| 2010/0274087 A1 | 10/2010 | Diolaiti et al. | |
| 2012/0290134 A1 | 11/2012 | Zhao et al. | |
| 2013/0226343 A1 | 8/2013 | Baiden | |
| 2013/0330700 A1 | 12/2013 | Feins et al. | |
| 2014/0142591 A1 | 5/2014 | Alvarez et al. | |
| 2014/0236175 A1 | 8/2014 | Cooper et al. | |
| 2014/0282196 A1 | 9/2014 | Zhao et al. | |
| 2014/0287393 A1 | 9/2014 | Kumar et al. | |
| 2014/0329215 A1 | 11/2014 | Pugh | |
| 2014/0356835 A1* | 12/2014 | Montalbano | G09B 23/283 434/263 |
| 2015/0024362 A1* | 1/2015 | Feins | G09B 23/303 434/268 |
| 2015/0082226 A1 | 3/2015 | Liu | |
| 2015/0206456 A1* | 7/2015 | Foster | A61M 5/31 434/262 |
| 2015/0374259 A1 | 12/2015 | Garbey et al. | |
| 2016/0133158 A1* | 5/2016 | Sui | G09B 23/285 434/262 |
| 2016/0140876 A1* | 5/2016 | Jabbour | G09B 23/285 434/262 |
| 2016/0203738 A1* | 7/2016 | Ho-Fung | G09B 23/30 434/272 |
| 2016/0314711 A1 | 10/2016 | Grubbs | |
| 2016/0314712 A1 | 10/2016 | Grubbs | |
| 2016/0314716 A1* | 10/2016 | Grubbs | A61B 34/35 |
| 2016/0314717 A1* | 10/2016 | Grubbs | G09B 23/306 |
| 2016/0324580 A1* | 11/2016 | Esterberg | A61B 34/10 |
| 2016/0329000 A1 | 11/2016 | Feins et al. | |
| 2017/0053564 A1* | 2/2017 | Triano | G09B 23/32 |
| 2017/0076636 A1* | 3/2017 | Moore | G09B 23/285 |
| 2017/0200399 A1* | 7/2017 | Thomas | G09B 23/285 |
| 2017/0294146 A1* | 10/2017 | Grubbs | G09B 9/00 |
| 2018/0174491 A1* | 6/2018 | Sauer | G09B 23/34 |
| 2018/0338806 A1* | 11/2018 | Grubbs | A61B 34/10 |
| 2019/0122581 A1* | 4/2019 | Munro | G09B 19/24 |
| 2019/0172371 A1* | 6/2019 | Eckert | G09B 23/303 |

OTHER PUBLICATIONS

La Torre et al., "Resident Training in Laparoscopic Colorectal Surgery: Role of the Porcine Model"; World J Surg. Sep. 2012; 36(9):2015-20; Abstract only—1 page.

Maier-Hein et al., "Surgical Data Science: Enabling Next-Generation Surgery"; Nature Biomedical Engineering, vol. 1; Sep. 2017; 10 pages.

Zhang et al., "Finite Element Meshing for Cardiac Analysis"; Institute for Computational Engineering and Sciences, Department of Computer Sciences, The University of Texas at Austin; Scholarly Paper; Aug. 2004, 9 pages.

Alan S. Brown, "A Model Heart Digital Simulation Takes on Its Toughest Challenge"; Mechanical Engineering, Apr. 2015; pp. 30-35.

Brock et al., "Accuracy of Finite Element Model-Based Multi-Organ Deformable Image Registration"; Med. Phys. 32 (6); Jun. 2005; pp. 1647-1659.

Feussner et al., 2017; Chapter 5 "Sugery 4.0"; In Thuemmler et al. (Ed); "Health 4.0: How Virtualization and Big Data are Revolutionizing Healthcare"; pp. 91-107; Springer International Publishing.

Bajaj et al., "Spatially Realistic Human Heart Finite Element Models From Medical Imaging"; Institute for Computational Engineering and Sciences, Department of Computer Sciences, The University of Texas at Austin; Scholarly Paper; Available at https://www.researchgate.net/ publication uploaded by Chandrajit L. Bajaj, Jan. 15, 2015; 15 pages.

Bajaj et al., "Modeling Cardiovascular Anatomy from Patient-Specific Imaging"; Comput Methods Appl Sci ; NIH-PA Author Manuscript; Jan. 1, 2009; 13:1-28; DOI: 10.1007/978-1-4020-9086-8_1 Source: PubMed; pp. 1-37.

(56) References Cited

OTHER PUBLICATIONS

U.S. Appl. No. 61/554,741, filed Nov. 2, 2011, entitled "Method and System for Stereo Gaze Tracking" by Wenyi et al.

* cited by examiner

SURGICAL SIMULATION SYSTEM USING FORCE SENSING AND OPTICAL TRACKING AND ROBOTIC SURGERY SYSTEM

PRIORITY APPLICATION(S)

This application is based upon U.S. provisional application Ser. No. 62/567,946 filed Oct. 4, 2017; and U.S. provisional application Ser. No. 62/532,470 filed Jul. 14, 2017; and U.S. provisional application Ser. No. 62/512,933 filed May 31, 2017; and U.S. provisional application Ser. No. 62/510,494 filed May 24, 2017; the disclosures which are hereby incorporated by reference in their entirety.

FIELD OF THE INVENTION

The invention relates generally to robotic surgery systems, and more particularly, this invention relates to robotic surgery systems and sensing the forces experienced by the patient during robotic surgery.

BACKGROUND OF THE INVENTION

Historically, surgery has been performed by making relatively large incisions in a patient to access a surgical site. More recently, robotic surgery allows a surgeon to perform procedures through relatively small incisions. The surgeon passes an endoscope through a small incision, and the endoscope includes a camera that allows the surgeon to view the patient's internal organs. Robotic procedures tend to be less traumatic, and to have shorter recovery times than conventional surgical procedures.

Representative examples of procedures that can be performed using robotic surgery include heart surgery, lung surgery, prostate surgery, hysterectomies, joint surgery, and back surgery. Companies like Intuitive Surgical, Inc. ("Intuitive") provide robotic systems that allows surgeons to perform minimally invasive surgery, including coronary artery by-pass grafting (CABG) procedures. The procedures are performed with instruments that are inserted through small incisions in the patient's chest, and controlled by robotic arms. The surgeon controls the movement of the arms, and actuates "effectors" at the end of the arms using handles and foot pedals, which are typically coupled to electronic controllers. Recent advances allow the surgeon to use voice commands, or "line-of-sight," to control the movement of the endoscope and other robotic arms. Further, the surgeon can "feel" the force applied to the tissue, so as to better control the robotic arms.

In addition to using an endoscope to view the surgical site, the surgeon can use a laser or scalpel to cut tissue, an electrocautery device to cauterize tissue, a "grabber" to grab tissue, such as cancerous tissue, to be removed from the body, and lights to illuminate the surgical site.

Each instrument has a unique control interface for its operation, so a surgeon, or pair of surgeons, must independently operate each device. For example, a surgeon might use a first foot pedal to control an electrocautery device, a second foot pedal to operate a robotic arm, and another interface to operate a laser. The handles and a screen are typically integrated into a console operated by the surgeon to control the various robotic arms and medical instruments.

One of the drawbacks of robotic surgery is a surgeon may manipulate the tool in a manner that generates excessive force, which injures tissue, or worse, breaks blood vessels and causes internal bleeding and even death. Training in robotic surgery reduces this problem. However, often training occurs with a trainee working under the direction of a skilled surgeon operating the robot. A surgical simulation device that would allow training and includes some type of force sensing generated by the robot tool and clarifies the anatomy to the trainee would be advantageous. It is also desirable to sense at least one of the force and torque experienced by a patient during surgery resulting from movement of the surgery tool and surgery arm once a surgeon has been adequately trained to perform live surgery on a patient.

SUMMARY OF THE INVENTION

This summary is provided to introduce a selection of concepts that are further described below in the Detailed Description. This summary is not intended to identify key or essential features of the claimed subject matter, nor is it intended to be used as an aid in limiting the scope of the claimed subject matter.

A surgical simulation device includes a support plate that defines a datum reference. A mannequin support structure is carried by the support plate. A mannequin is carried by the mannequin support structure and has a body cavity corresponding to at least one of a thorax and abdomen. A pedestal is connected to the support plate and extends upward through the mannequin support structure into the body cavity. A tissue tray is carried by the pedestal within the body cavity. Animal tissue is carried by the tissue tray. A first sensor is connected to the pedestal between the tissue tray and support plate and configured to sense force and torque exerted against the animal tissue from at least one surgical tool exerting force against the tissue during surgical training. A second sensor is connected between the mannequin support structure and support plate and configured to sense force and torque exerted against the mannequin onto the support plate. A processor is connected to the first and second sensors and configured to determine the force exerted against respective areas of the animal tissue and mannequin during surgeon training.

The surgical simulation device may comprise at least one camera connected to the processor. Markers are positioned within the mannequin and on the animal tissue. The processor is configured to receive video images and form a three-dimensional wire frame image of the body cavity and animal tissue. The markers may comprise light emitting diodes, an optical fiber, or passive reflectors. The at least one camera may comprise a three-dimensional video camera.

A surgical simulation device includes a support structure and a tray carried by the support structure. Animal tissue is carried by the tray. A simulated human skeleton portion is carried by the support structure above the animal tissue. Simulated human skin covers the simulated human skeleton portion. Markers are positioned on the ribs and animal tissue. At least one camera is positioned to image the animal tissue and simulated human skeleton portion during surgeon training. An image processor is connected to the at least one camera and configured to receive images of the markers and form a three-dimensional wireframe image of the tissue and the skeleton.

In an example, a display is connected to the image processor for displaying the three-dimensional wireframe image during surgical training. In different examples, the markers may comprise light emitting diodes, an optical fiber, or passive reflectors. The at least one camera may comprise a three-dimensional video camera and a video recorder may be connected to the at least one camera. A memory may be coupled to the image processor for storing the three-dimensional wireframe image and changes made to the wireframe image during surgical training.

In yet another example, the simulated human skeleton portion may comprise a spinal column and a rib cage coupled thereto. The simulated human skin may comprise an innermost layer and an outermost layer. The innermost layer may protrude between the ribs of the rib cage. In yet another example, a simulated human diaphragm is within the rib cage and the animal tissue may comprise a heart and lung block. At least one animating device may be coupled to the heart and lung block. The animal tissue may comprise harvested porcine tissue or human cadaver tissue. A robotic surgery station may be adjacent the support structure and comprise at least one surgical tool.

A robotic surgery system includes a local robotic surgery station configured to perform robotic surgery on a patient and an operating table adjacent the local robotic surgery station. The operating table includes at least one patient support configured to support the patient during robotic surgery, and at least one patient force/torque sensor coupled to the at least one patient support and configured to sense at least one of force and torque experienced by the patient during robotic surgery.

A processor may be coupled to the at least one patient force/torque sensor and configured to generate an alert indication when a threshold is exceeded or to stop the local robotic surgery station when the threshold is exceeded or any combination. The local robotic surgery station may comprise a robotic surgery device and at least one robot force/torque sensor coupled thereto and configured to sense at least one of force and torque experienced by the robotic surgery device during robotic surgery. The processor may be configured to record data from the at least one patient force/torque sensor and the at least one robot force/torque sensor. The robotic surgery device may comprise at least one robotic surgery arm and a surgery tool coupled thereto.

In another example, a remote robotic surgery station may be coupled to the local robotic surgery station. A cable may be coupled to the remote robotic surgery station and the local robotic surgery station. The remote robotic surgery station may be configured for use geographically remote from the local robotic surgery station.

The at least one patient force/torque sensor may comprise a plurality of semiconductor strain gauges and circuitry coupled thereto to output six components of force and torque. The operating table may comprise a frame and the at least one patient force/torque sensor may be coupled between the frame and the at least one patient support. The at least one force/torque sensor may comprise a plurality thereof. The at least one patient support may comprise a plurality thereof.

In yet another example, a robotic surgery system includes a local robotic surgery station comprising at least one robotic surgery arm and a surgery tool coupled thereto and configured to perform robotic surgery on a patient. A remote robotic surgery station is coupled to the local robotic surgery station and an operating table is adjacent the local robotic surgery station. The operating table includes a frame, at least one patient support configured to support the patient during robotic surgery, and at least one patient force/torque sensor coupled between the frame and the at least one patient support to sense at least one of force and torque experienced by the patient during robotic surgery.

A robotic surgery method includes using a local robotic surgery station to perform robotic surgery on a patient while the patient is positioned on an operating table adjacent the local robotic surgery station, the operating table comprising at least one patient support supporting the patient during robotic surgery and using at least one patient force/torque sensor coupled to the at least one patient support to sense at least one of force and torque experienced by the patient during robotic surgery.

DESCRIPTION OF THE DRAWINGS

Other objects, features and advantages of the present invention will become apparent from the detailed description of the invention which follows, when considered in light of the accompanying drawings in which.

DETAILED DESCRIPTION

Different embodiments will now be described more fully hereinafter with reference to the accompanying drawings, in which preferred embodiments are shown. Many different forms can be set forth and described embodiments should not be construed as limited to the embodiments set forth herein. Rather, these embodiments are provided so that this disclosure will be thorough and complete, and will fully convey the scope to those skilled in the art.

Figure 1:
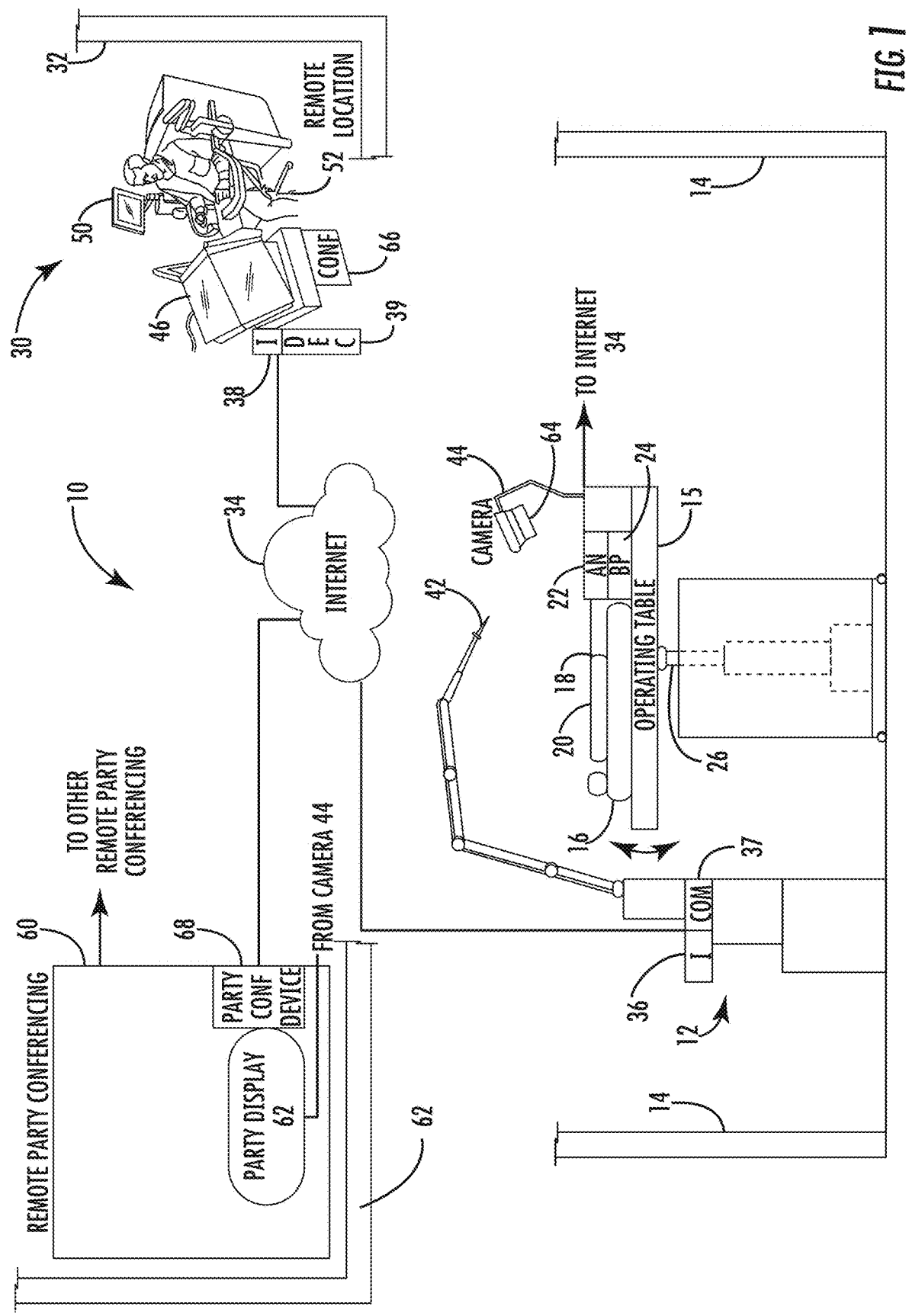
FIG. 1 is a fragmentary, block diagram of the telerobotic surgery system showing basic features in accordance with a non-limiting example.

The telerobotics surgery system for remote surgeon training is shown generally at 10 in FIG. 1 and includes a robotic surgery station 12 at a first location in a first structure 14 at a first geographic point. The first structure 14 could be a fixed building or could be a vehicle/trailer or other structure temporarily positioned for use. The robotic surgery station 12 simulates a patient undergoing robotic surgery. It includes an operating table shown generally at 15, and in this example, a mannequin 16 includes an animal tissue cassette 18 and is mounted on the operating table 14. The cassette 18 is configured to hold at least harvested animal tissue 20. At least one animating device 22 is coupled thereto. A blood perfusion device 24 is coupled to the harvested animal tissue 20, e.g., lung tissue and heart tissue in this example. In a preferred example, the harvested animal tissue 20 does not include human cadaver tissue. While porcine tissue is used for many training scenarios, the tissue of sheep, goat or canine may be used as well. The animating device 22 is a movement device that is configured to simulate normal and abnormal breathing, and normal and abnormal heartbeat using techniques such as balloons inserted into the tissue as explained below. As noted before, the mannequin 16 may receive the tissue cassette 18 that may be tilted or moved using an actuator 26.

A remote surgeon station 30 is at a second location in a second structure 32 at a second geographic point that is remote from the first geographic point. A communications network 34, such as the internet, couples the robotic surgery station 12 and the remote surgeon station 30 so that a surgeon at the remote surgeon station is able to remotely train using the harvested animated animal 20 tissue at the robotic surgery station. In the example, the communications network 34 may have a latency of not greater than 200 milliseconds, and in another example, may have a latency of not greater than 140 milliseconds. As illustrated, a first communications interface 36 is coupled to the robotic surgery station 12 and a second communications interface 38 is coupled to the remote surgeon station 30. The first and second communications interfaces 36, 38 are configured to be coupled together via the internet as the communications network 34 in this example. As illustrated, the robotic surgery station 12 is positioned adjacent the operating table 15 and has at least one surgical tool 42, which could be different tools depending on what type of surgery is simulated. At least one camera 44 is located at the robotic surgery station 12 and the remote surgeon station 30 includes at least one display 46 coupled to the at least one camera 44 via the communications network 34, in this case the internet. In an example, the first communications interface 36 is configured to determine if a latency is above a threshold, and when above a threshold, performs at least one of image size reduction and reducing the peripheral image resolution on the display 46. This will allow data to be transported over the internet connection while maintaining high image resolution at those areas of the image that are more critical for the training.

The first communications interface 36 may include a data compression device 37 and the second communications interface 38 may include a data decompression device 39. In an example, the at least one camera 44 may be formed as a stereo image camera and the at least one display 46 may include a binocular display 50 as illustrated in FIG. 1 that could be moved directly over the eyes of the trainee. Alternatively, the trainee could view the large display screen 46 or manipulate the binocular display 50 and view the surgical procedure.

As noted before, the at least one animating device 22 may include a movement animating device to simulate at least one of the breathing and heartbeat, including normal and abnormal breathing, and normal and abnormal heartbeat.

In an example, the first location having the robotic surgery station 12 may be associated with a room not for live human operations. The second location having the remote surgeon station 30 may be associated with an operating room for live human operations in one example. The trainee such as a student surgeon or experienced surgeon learning new techniques may sit in the operator chair that is part of a real operating room and operate the robotic surgery station 12 telerobotically as described in greater detail below. As noted before, the remote surgeon station 30 includes at least one input device 52 as hand controls in this example, and the robotic surgery station includes at least one output device coupled to the at least one manual input device 52, which in this example is the at least one robotic surgical tool 42 as illustrated that provides a feedback signal with the at least one manual input device shown as the hand controls and responsive to the feedback signal.

As illustrated in FIG. 1, a remote party conferencing station 60 is at a third location in a third structure 62 at a third geographic point remote from the first and second geographic points. The communications network 34 such as the internet not only couples the robotic surgery station 12 to the remote surgeon station 30, but also couples to the remote party conferencing station 60 so that a surgeon at the remote surgeon station 30 is able to remotely train using the harvested animal tissue 20 at the robotic surgery station 12, and while conferencing with a party at the remote party conferencing station 60. For example, there could be a group of surgeons or students located at the remote party conferencing station that will observe, watch and even confer with the surgeon or student trainee located at the remote surgery station. There can be multiple stations and multiple persons present at each station. The remote party conferencing station 60 may also include at least one party display 62 coupled to the at least one camera 44 located at the robotic surgery station 12 via the communications network 34. A video recorder 64 may be coupled to the at least one camera 44. The remote surgeon station 30 may include a surgeon conferencing device 66 and the remote party conferencing station 60 may including a party conferencing device 68 coupled to the surgeon conferencing device via the communications network 34. Thus, a voice conference may be established between the surgeon at the surgeon conferencing device 66 located at the remote surgeon station 30 and the party conferencing device 68 located at the remote party conferencing station 60.

Figure 2:
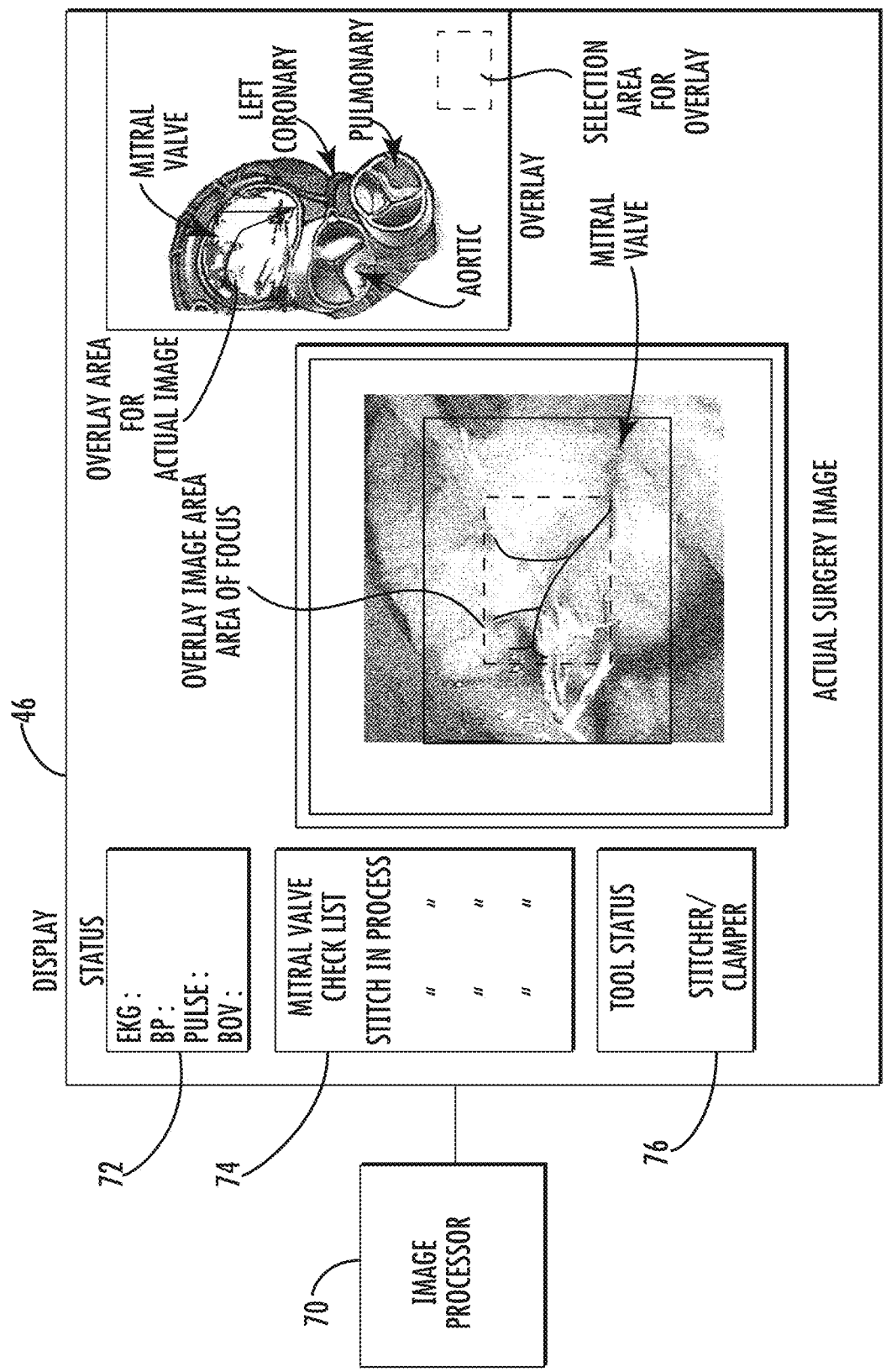
FIG. 2 is a block diagram of a surgeon display and an image processor that generates an additional image in accordance with a non-limiting example.

At the remote surgeon station 30, an image processor 70 may generate an additional image on the at least one surgeon display 46 and the additional image may include an anatomical structure image corresponding to the actual animal tissue image such as shown in FIG. 2. This image processor 70 may be configured to overlay the anatomical structure image on the actual animal tissue image. For example, the additional image may include a surgery status information image 72, for example, a training scenario. The surgery status information image 72 may include at least one of an EKG value, a blood pressure value, a heart rate value, and a blood oxygen value and be synchronized to the actual animal tissue image. The additional image may also include a surgery instructional image 74, for example, a surgery checklist. For example, the harvested animal tissue may simulate a desired heartbeat, for example, 78 bpm, and the tissue, if cut, will bleed and the heartbeat will be displayed and recorded. The "corresponding" anatomical image added on the surgeon display could be the heart and lung image or heart image 76 of a person such as from Grey's Anatomy, for example. The surgical status information could be an indication such as the color change for the robotic tool, or color change to indicate operation of a cautery tool or activation of a stapler. This all helps in training the surgeon or student surgeon.

The operating table could include an immersion tank carried by the operating table and configured to contain liquid. An inflator could be configured to be coupled to harvested animal lung tissue to inflate lung tissue and be connected to a heart tissue via inflatable balloons and pulsed to form a heartbeat as explained below. The operating table could include a lift mechanism to move the animal tissue cassette and/or mannequin between different operating positions.

Examples of simulated surgical procedures include heart by-pass operations, valve replacements or repair, lung re-sectioning, tumor removal, prostatectomy, appendectomy, hernia operations, stomach stapling/lap band operations, orthopedic surgery, such as rotator cuff repair and arthroscopic knee surgery. In addition to actual operations, specific skill sets can be developed, for example, vein dissection, use of staplers, cautery, and the like. Each of these surgeries and/or skill sets can be practiced using an appropriate tissue, organ or organ block, as discussed in detail below.

The systems include one or more surgical simulator units that include animal, cadaver, or artificial tissues, organs, or organ systems, providing a non-living but realistic platform on which to perform surgery. The systems also include one or more instruments for performing robotic surgery, so that one or more simulated surgical procedures can be performed on tissues, organs, or organ systems in the surgical simulator units. The systems optionally, but preferably, also include a telecommunications system which allows remote access to, and control of, the instruments used to perform robotic surgery, thus allowing simulated robotic surgery to be performed remotely.

In one aspect of this embodiment, a surgeon can remotely access a simulation center, and either perform an operation or practice their skills. The simulation center includes one or more surgical simulators, one or more instruments for robotic surgery and animated animal tissue such as part of a cassette or mannequin.

In another aspect of this embodiment, a teaching surgeon can remotely access a surgical simulation center that includes the systems described herein, and instruct a student surgeon on how to perform a particular robotic surgical operation. The student surgeon can either be present at the simulation center, or can remotely access the simulation center. The teaching surgeon can perform one or more of the following:

a) teach the procedure as the student observes, b) observe the student as the student performs the procedure, and give feedback, which can include real-time feedback and/or feedback after the procedure is completed, and c) allow the student to perform the procedure, but take over control of the instruments where the student, for example, where the instructor perceives that the student has made a mistake, optionally by providing tactile feedback to the student, so that the student "feels" how the proper motion of the surgical instruments should be.

In still another aspect of this embodiment, multiple surgeons can access a simulation center, with each surgeon individually accessing the center locally or remotely. A plurality of surgical simulators, each of which includes its own tissue, organ, or organ block "cassettes," and each of which is controlled by a different robot. In this embodiment, a single instructor can guide a plurality of students through a surgery or skills exercise. Where more than one surgeon is operating a robotic instrument, the instructor and/or students can be joined in a virtual surgical setting using appropriate web conferencing software, such as that provided by Adobe Connect.

By using web conferencing software, one can provide access across devices, and allow sessions to be recorded and, optionally, edited at a later time. Web conferencing can provide highly secure communications, and can also ensure compliance with applicable laws. The conference can provide an immersive experience for the students, and allows for them to easily create a record of their attendance. Each surgical simulation can be customized, and different types of content can be delivered. For example, an instructor can alternate between a visual slide presentation and/or video presentation of the type of surgical procedure to be performed, and the performance of the actual procedure in real-time. The web conference can allow for mobile learning across multiple devices, and allow some students to participate live, and others to participate later in an "on-demand" manner. As a result, a web conference can provide efficient management and tracking for training on surgical simulators.

In one aspect of this embodiment, cloud computing is used to control the robotic surgical instruments, where one or more surgeons can participate in the surgical procedure. For example, one surgeon can teach other surgeons how to perform the procedure, and/or multiple surgeons can work collaboratively on a single "patient" to perform one or more procedures.

The individual elements of the systems described herein are described in detail below.

I. Types of Tissue/Organs

The surgical simulator systems includes animal, cadaver human, or artificial tissue and/or organs, and/or organ blocks including the organs, or combinations thereof. These tissues, organs, and/or organ blocks are included in simulated surgical devices, such that a surgeon can perform lifelike surgery on real, or at least realistic, tissue.

One or more of these tissue, organs, and/or organ blocks can be hooked up to a source of animal blood, theater blood, or other colored liquid to simulate bleeding, and/or can be hooked up to a source of a gas and/or vacuum, which can be used to simulate organ movement.

For example, animal lungs present in the surgical simulator can be expanded and contracted to simulate normal breathing, or to simulate other types of breathing, such as shallow breathing, coughing, and the like. A heart can be expanded and contracted to simulate a heartbeat, for example, by inflating one or more balloons inside the heart, for example, inside the ventricles.

So as to allow connection to a source of a gas or vacuum (to inflate/deflate the lung or cause the heart to "beat"), or to artificial or animal blood, the organs can be equipped with quick-connect tubes. Using these quick-connect tubes, the organs or organ blocks can be quickly incorporated into a surgical simulator, and attached to a source of air and vacuum, such as a bellows, an ambu bag, and the like. Where the surgical simulator includes a heart, the heart can be expanded and contracted, for example, using a balloon attached to a source of air and a source of vacuum.

Though judicious application of a gas to a balloon or other expandable member, different heartbeat rhythms can be produced, simulating a normal heartbeat, a distressed heartbeat, arrhythmias, a heart attack, and the like. In one aspect of this embodiment, a surgeon can simulate the steps needed to be taken following a myocardial infarction, where the surgical instruments must often be removed before resuscitation efforts can be initiated.

The surgical simulator can also include animal joints that simulate human joints, so that joint surgery can be simulated. For example, sheep and goats are a convenient large-animal model for rotator cuff repair (Turner, "Experiences with Sheep as an Animal Model for Shoulder Surgery: Strengths and shortcomings," Journal of Shoulder and Elbow Surgery, Volume 16, Issue 5, Supplement, September-October 2007, Pages S158-S163). Tenotomy of the infraspinatus tendon and subsequent reattachment to the proximal humerus is useful to address the biomechanical, histologic, and biochemical processes of rotator cuff repair. Detaching this tendon and immediately reattaching it does not represent the clinical picture but serves as a relatively rapid way to screen different suture anchors, suture patterns, scaffolds, and other treatments. A porcine model can be used to simulate knee surgery. For example, anatomic ACL reconstructions and other types of knee surgeries can be simulated using a porcine model.

Laparoscopic colorectal surgery (LCRS) is an effective option for the treatment of various colorectal conditions, and can be evaluated in an animal porcine model (La Torre and Caruso, "Resident training in laparoscopic colorectal surgery: role of the porcine model." World J Surg. 2012 September; 36(9):2015-20).

Non-limiting examples of animals from which the tissue, organ, and organ blocks can be obtained include cow, sheep, goat, pig, baboon, dog, and cat.

Development of a Module Lot

A group of animal tissue collections may be made from a series of animals before butchering for food so that no animals are sacrificed beyond what would be butchered for food. By collecting a series of tissue collections by the same facility using the same procedure from the same herd of animals (same breed, same age, same food), there will be extensive similarities among the collected tissue samples. As is understood by those of skill in art, some features vary even between identical twins such as the vascular pattern around the exterior of the heart so some features cannot be closely controlled. However, certain degrees of variability can be decreased by clustering tissue samples by gender of donor animal, nominal weight of donor animal, or some other property of the animal or classification made of the harvested tissue sample.

The organs used in the surgical simulators can be preselected so as to have various defects, such as tumors, valve defects, arterial blockages, and the like, or can be selected to be as close to identical as possible. In the former embodiment, a surgeon can demonstrate a particular type of operation where a particular defect is present, and in the latter embodiment, a surgical instructor can demonstrate a technique to multiple students, using organs that are closely matched, so that the results would be expected to be the same if the students perform the surgery correctly.

In general, the organs may be characterized using a wide variety of available metrics. These may include volume of ventricles, stiffness of the muscle tissue (restitution test), specific gravity, % fat, pressure testing, presence or absence of tumors, blockage or arteries, etc. The recorded metrics will be specific to the scenario being replicated. Ideally, the organs selected are as close to the size and weight of human organs.

Examples of classification of the tissue samples may include:

A) Some characterization of the amount of fatty material surrounding the tissue of interest.

B) Some characterization of the pliability/stiffness of the tissue.

C) Some characterization of the properties of the relevant blood vessels such as degree of occlusion.

D) One way to characterize an organ is the time it takes for a fluid to drip out from a container and into an organ. As the receiving volume of the organ will be relatively uniform (for organs of the same size) this may characterize the ability of fluids to flow through the structures in the organ and out.

Representative Xenographic Organ Preparation

Porcine organ blocks including the heart with pericardium, lungs, trachea, esophagus, and 8-12 inches of aorta can be obtained from a local supplier. There is no need to sacrifice animals to obtain these organs or organ blocks, as these can be harvested from an animal before butchering the animal for food products.

Organ preparation can begin with an incision of the pericardium on the right posterior side of the heart, so it can later be reattached with no noticeable holes when viewed from the left side. The superior vena cava, inferior vena cava, right pulmonary artery, and right pulmonary veins can then be divided with care taken to leave as much vessel length as possible. After the right lung is fully detached, the organs can be washed extensively to remove coagulated blood from the heart and vessels. All divided vessels, except for the main branch of the right pulmonary artery and right superior pulmonary vein, can be tied off, for example, using 0-silk.

As an example of quick-connect tubes, small diameter plastic tubes with Luer-Lok® connectors can then be placed into the divided right pulmonary artery and right superior pulmonary vein, and fixed in place, for example, using purse-string sutures. To create distention of the aorta, one can inject silicone caulking to the level of the ascending aorta.

After the silicone cures, the brachiocephalic trunk and left common carotid can be tied off, for example, using 0-silk.

The left main stem bronchus can be occluded, for example, by stapling the divided right main stem bronchus as well as the proximal trachea. The left hilum can remain unaltered, and all modifications to the heart can be hidden by the pericardium during the procedure.

Following preparation, the organs can be stored at a relatively low temperature, for example, 4 degrees Celsius, in an alcoholic solution, for example, 10% ethanol containing teaspoon of red food coloring. In this manner, the organs typically remain fresh for at least 1 month. Use of higher concentrations of alcohol, such as 40% ethanol, can preserve the organs for over a year, and, ideally, up to 18 months, and can perform as well as freshly-harvested organs.

Simulating Trauma

While having similar tissue for use in creating various staged reality modules within a lot is helpful, the ability to precisely create trauma in ex vivo tissue samples is of even greater importance. Having harvested tissue samples of a similar size and quality allows the tissue samples to be placed in a jig so that the trauma may be applied in a controlled way a precise offset from one or more anatomic markers. Examples of trauma include:

A) A set of uniform metal pieces may be created and implanted a set depth in a set location to allow for a set of shrapnel wounds to be placed in a series of tissue samples that will become staged reality modules within a given lot.

B) A particular volume of silicon or some analogous material may be placed in the same location in a series of harvested lungs to emulate lung tumors.

C) Trauma may be emulated for chemical burns or other trauma to the outer layers of tissue of a faux patient.

D) In lieu of implanting faux ballistic debris, organs placed in jigs can receive ballistic projectiles from a weapon.

In order to verify that the trauma induced fits within the parameters for this particular set of traumatized organs, the trauma could be examined and characterized by ultrasound or some other diagnostic imaging method. One may also sprinkle a little gunpowder around the wound just before the session started and ignite it to create fresh burns and realistic smells of the battlefield.

Spleen Example

Another example of a staged reality module is a spleen that has received a standardized shrapnel injury (precise and repeatable insertion of standardized pieces of metal rather than actual pieces of shrapnel from an explosion). The staged reality module for the injured spleen can be placed as module A-50 (Figure A). The staged reality module would be prepared with quick connect fittings to allow connection to a port on an umbilical cable to provide a source of faux blood and to provide a clear liquid to weep from the wound.

Optionally, the spleen may have instrumentation to provide an indication of when the spleen was first by cut the surgeon. This information could be conveyed by the data bus. In order to provide a standardized set of injured spleens for testing or simply for use in an ordered curriculum, a set of substantially identical spleens harvested from donor animals that will be butchered for food may be prepared in the substantially same way.

As noted above, the packaging may convey information about the staged reality spleen module.

A porcine organ block can be placed in a lower tray to retain fluids analogous to a metal baking tray. For purposes of simulating a human, the porcine heart can be rotated to emulate the position of a human heart in a torso. For example, the left side of the porcine heart can be placed into the tray with the left lung placed over an inflatable air bladder.

Adapting Organs for Inflation/Deflation, Beating, and/or Bleeding

Inflation and deflation of lungs of a real patient causes the rise and fall of the mediastinum. An appropriate volume of air or some other fluid may be used to inflate and deflate an appropriately sized and placed container hidden under the tissue to be animated with movement. For example a respiration rate of 20 breaths per minute can be simulated by periodically expanding an air bladder such as a whoopee cushion, or an empty one-liter IV bag that is folded in half.

Lightly pressurized theater blood or animal blood can be provided through a connection to the umbilical cable port to provide blood emulating fluid into the divided right pulmonary artery and divided right superior pulmonary vein to distend and pressurize the venous and arterial systems. Static fluid pressure within the vessels can be achieved using gravity flow from an IV bag. Pressure is ideally limited, to avoid severe pulmonary edema. Extended perfusion times (1-2 hours) can be maintained without substantial fluid leakage into the airways by preparing the porcine organ block to occlude the left mainstem bronchus to inhibit leaking and loss of pressure.

A balloon placed in the heart and connected to a closed system air source to allow for emulating the beating of a heart (such as at a rate of 78 beats per minute) adds to the sense of realism of the simulated surgical procedure. In this manner, the organs and/or organ blocks can be animated by providing one quick connect fitting to connect the heart balloon to an air supply to provide a beating heart effect, and a second quick connect fitting can be connected to a different pneumatic connection to provide air to the lungs, providing lung movement to simulate breathing. A fluid quick connect fitting connected to the joined blood vessels can allow for slightly pressured simulated blood to be provided. One or more of these connections can be made to an umbilical cable.

As used in this specification, a quick connect fitting is one that may be connected to a corresponding fitting without using tools. A quick connect fitting can be used to connect to hydraulic line, pneumatic line, electrical line, and/or digital communication bus.

II. Surgical Simulator

The tissue, organs, and/or organ blocks described above are included in a carrier/container to simulate the view a surgeon would see when performing surgery. This view may simply include draping over the tissue, organs, or organ blocks to be operated on, where the organs are stored in a box or other suitable container, held at the height appropriate for the surgeon to perform the surgery. However, in some embodiments, the tissue, organs, and/or organ blocks described above are included in a mannequin, and/or are provided along with photographs representative of what would be seen in an actual human undergoing this surgical procedure, so as to provide a more realistic surgical experience.

Modules including the tissue, organs, and/or organ blocks, along with the quick connections to sources of gas, vacuum, and/or animal or fake blood, can be quickly inserted into a relevant portion of a segmented mannequin, connected via one or more quick connect fittings to corresponding fittings on a convenient umbilical cable port to quickly prepare a mannequin for simulated robotic surgery.

Other staged reality modules may be likewise connected. Pressure levels (such as the height of an IV bag supplying the master-controller) or pulse volumes (for heart or lung motion) may be adjusted at the master-controller. The mannequin may then be draped to expose the relevant surgical sites. Optionally, the packaging carrying the staged reality module (the porcine organ block with modifications and quick connect fittings) may include a bar code, data matrix code, other optical code, or other machine readable data storage device that is accessed by a bar code reader or other reader device in data communication with the master-controller. Thus data concerning this specific staged reality module can be made available to the master-controller and combined with other information gathered during the surgical simulation and made part of a data record for this training or certification session. Another option would be the use of a passive RFID label.

Figure 3:
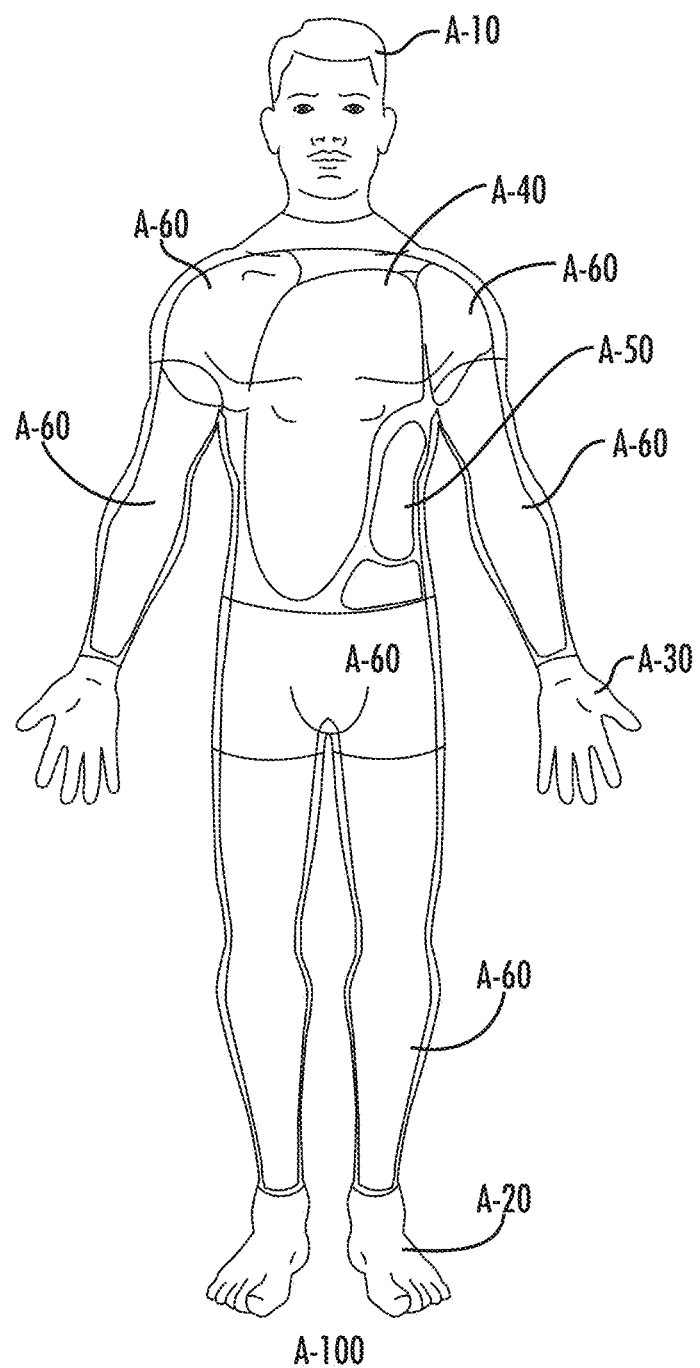
FIG. 3 is a top view of a segmented mannequin A-100.

Although other embodiments can be used, in one embodiment, the surgical simulator includes a segmented mannequin, as shown in FIG. 3. FIG. 3 is a top view of a segmented mannequin A-100. The mannequin may include certain permanent features such as a mannequin head A-10, mannequin feet A-20, mannequin hands A-30. These permanent features may be made of a material that roughly approximates the feel and weight of a human component although without the need to emulate the properties of tissue when cut or sewn. These components could be obtained from sources that provide mannequin parts for mannequins used for CPR practice. The permanent mannequin parts used away from the surgical sites are there to assist in the perception in the staged reality that the patient is a living person. Alternatively, preserved parts from a cadaver may be used. In other alternatives, these body portions that are not directly involved with a staged reality of an event requiring surgery may be omitted and covered with drapes.

Staged reality component A-40 may be some subset of the mediastinum. For example, A-40 may represent a heart and pair of lungs. A separate staged reality module present in FIG. 3 is a spleen module shown as A-50. Note that while this example shows two active staged reality modules, in many training exercises, a single staged reality module will be presented with a number of repetitions.

The remainder of the segmented mannequin A-100 may be filled with a series of mannequin filler pieces A-60. The filler pieces may be made of ballistic gelatin. Ballistic gelatin approximates the density and viscosity of human muscle tissue and is used in certain tests of firearms and firearm ammunition. Approximating the density of human tissue may add to the realism by adding weight to the mannequin segments that approximates the weight of actual human components so that lifting a leg of the mannequin approximates the effort to lift a human leg. Alternatively, multiple staged reality modules may be present on single mannequin.

Filler pieces made of ballistic gelatin may have a finite life as that material degrades. An alternative material for filler pieces may be made from commercially available synthetic human tissue from a vendor such as SynDaver™ Labs that supplies synthetic human tissues and body parts. SynDaver™ Labs is located in Tampa, Fla., and has a web presence at http://www.syndaver.com. Some mannequin filler pieces may be sized to fill in around a specific staged reality module such as the spleen staged reality module. Others may be standard filler pieces for that particular mannequin. (A child mannequin or a mannequin for a super obese patient may have proportionately sized filler pieces).

Figure 4:
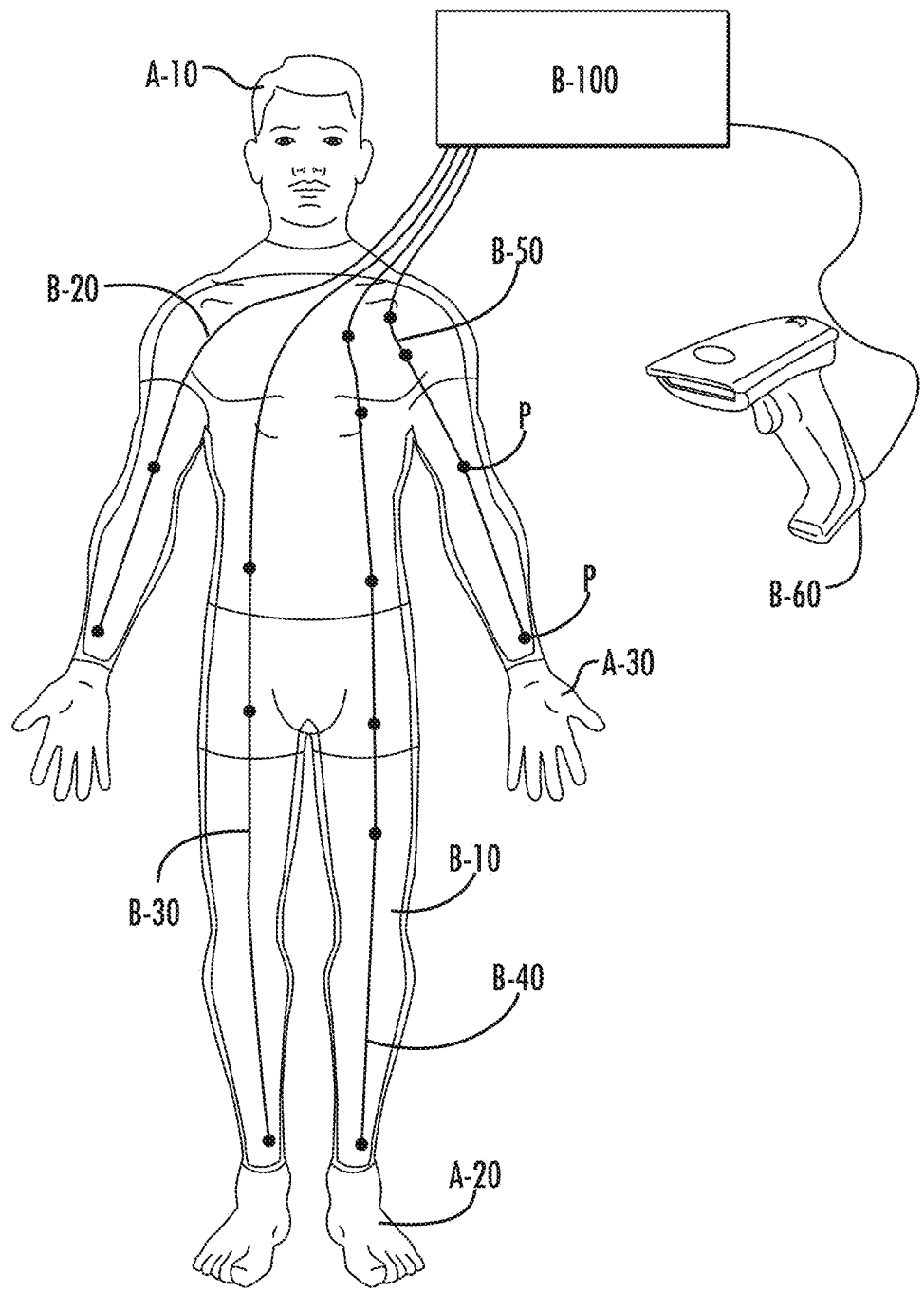
FIG. 4 shows a segmented mannequin A-100 similar to that shown in FIG. 3 with an open body cavity B-10 without the staged reality modules A-40 and A-50 that may be used in accordance with a non-limiting example.

FIG. 4 shows segmented mannequin A-100 with an open body cavity B-10 without the staged reality modules A-40 and A-50. FIG. 4 also lacks the mannequin filler pieces A-60 but retains the permanent mannequin parts A-10, A-20 and A-30.

The mannequin may include drain gutters and drain holes to remove excess liquid from the body cavity (not shown).

FIG. 4 includes a high level representation of the control system. Master-controller B-100 is connected to a series of umbilical cables, shown here in this example as umbilical cords B-20, B-30, B-40, and B-50. The mannequin may have fewer than four umbilical cables or more than four umbilical cables without departing from the teachings of the present disclosure. As described in more detail below, each umbilical cable may provide some combination of one or more pneumatic supply lines, one or more pressurized fluid supply lines, one or more instrument communication buses, and low voltage electrical supply to power module electronics and sensors.

FIG. 4 includes a series of ports P at various points along the four umbilical cables. The ports P allow for a staged reality module to be connected to an umbilical cord to receive pressurized fluids, pneumatic air (or other gas), connection to instrument communication buses, and low voltage electrical supply. While for simplicity, each port P is shown as an enlarged dot, a port is likely to have a series of different connections for different services provided to a module. Unless the port is located at the distal end of an umbilical cable, the port may appear as a short branch that is part of a T-connection to the umbilical cable.

A particular module may connect to one or many different connections. Several staged reality modules (such as A-40 and A-50) may be connected to ports along one umbilical cable (B-40). A designer of a comprehensive mediastinum module representing a number of structures found in the thorax cavity might find it useful to connect to ports on two parallel umbilical cables (such as B-30 and B-40) in order to minimize routing of connectors within the module.

FIG. 4 includes a bar code scanner B-60 that may be used to read bar code information from the packaging for the staged reality module. A bar code or other optical code could be used to convey a unique identifier for the module (source and unique serial number). A series of bar codes, a data matrix code (a two-dimensional matrix bar code), or some other optical code could be used on the module packaging to convey an array of data about the module. This data could be different for different types of modules but it may include the creation date of the module, the harvest date when the tissue components of the module were collected, and characterization data that may be relevant.

Characterization data may include:

A) a lot number which would provide a way to know that a given set of modules was created at the same time and intended to be used to provide substantially repeatable staged reality simulations;

B) a grade number which would apply across more than one lot so that modules created at different times but to a certain array of standards would have the grade number so that modules within the same grade number could be used if a sufficient number of modules within a particular lot number were not available;

C) an indication of the level of blockage of certain vessels;

D) an indication of the level of pliability/stiffness of certain tissue structures (which may increase the level of difficulty for certain procedures and mimic characteristics of certain patient populations);

E) an indication of the level of obesity associated with this module which may include the use of simulated fatty material that was added to the module to obfuscate the structure of the underlying tissue as often happens in actual surgery.

Inflation and Deflation of Lungs in an Organ Block

Where the organ block includes lungs, the lungs can be inflated and deflated using the methods described herein.

Inflation and deflation of lungs of a real patient causes the rise and fall of the mediastinum. To simulate this, an appropriate volume of air or some other fluid can be used to inflate and deflate an appropriately sized and placed container hidden under the tissue to be animated with movement. For example a respiration rate of 20 breaths per minute can be simulated by periodically expanding an air bladder such as a whoopee cushion, or an empty one-liter IV bag that is folded in half.

Rather than merely animating the tissue by causing it to rise and fall, one can connect lungs to a source of gas, such as air or nitrogen, and cycle the air going into and out of the lungs in such a way as to mimic respiration. For example, a bellows or an "Ambu bag," can be used to provide a "pulsatile" air supply. A suitable arrangement is described, for example, in U.S. Patent Publication No. 2013/0330700.

Figure 5:
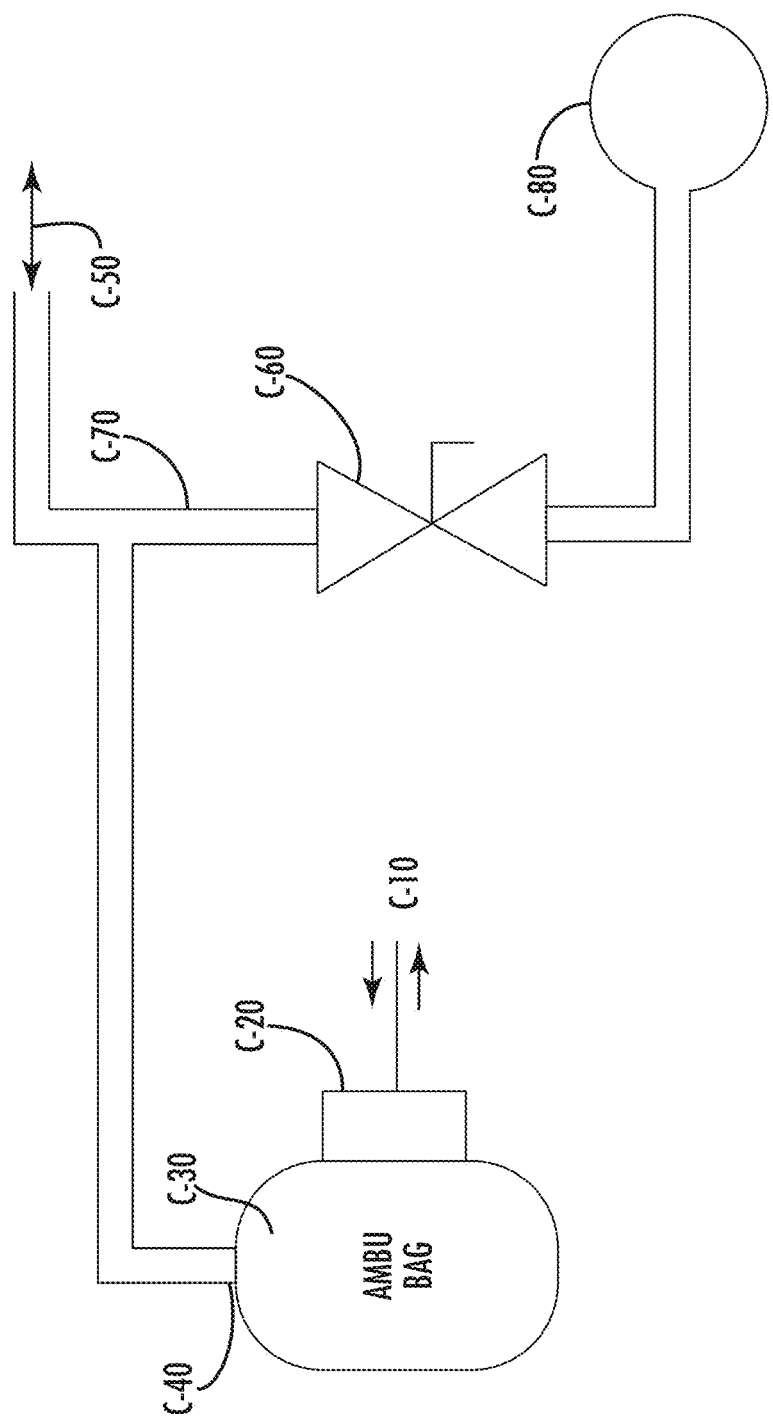
FIG. 5 shows a diagram for a pulsatile air pump that may be used in accordance with a non-limiting example.

In one embodiment, the lungs on a simulated patient can be inflated and deflated using the pulsatile air pump shown in FIG. 5. The air provided to the pulsatile air supply on the umbilical cable can be generated as symbolized by elements in FIG. 5. A linear input source (potentially stabilized by a linear bearing) moves a contact element C-20 relative to an anchored Ambu bag C-30. An Ambu bag (also known as a bag valve mask ("BVM")) is a hand-held device used to provide positive pressure ventilation to a patient that is breathing inadequately or not at all. The Ambu bag has a number of one way valves useful for this purpose.

One of skill in the art will recognize that moving the contact element C-20 relative to the Ambu bag will mean that for a portion of the stroke of the linear actuator C-10 that the contact element does not impact the Ambu bag. Thus the input to the Ambu bag C-30 can be altered from a sinusoidal input to more of a pulsatile input. Adjustments to the size of the Ambu Bag or its analogous replacement, the size of the contact element C-20 and the stroke length of the linear actuator after contact with the Ambu Bag will alter the air output at C-40. While the linear actuator C-10 could be a stepper-motor, other simpler solutions such as a windshield wiper motor could be used.

If this air source is used to animate a heartbeat then it would need to operate at a reasonable pulse rate for example 78 beats per minute. This pulse rate could be adjustable if desired or relevant to the staged reality.

Alternatively, if the air source is used to animate movements in response to respiration, then the pulses per minute would need to be reasonable for a patient undergoing surgery.

Fine tuning to control the amount of air C-50 provided to the umbilical cable (not shown) or a series of two or more umbilical cables via a header (not shown), may be achieved by a ball valve C-60 connected via Tee joint C-70. The ball valve C-60 may be used to divert air to bladder C-80 (such as a pair of balloons one within the other). The bladder should be operated in an elastic range so that the expanded bladder presses the air back towards the Ambu Bag when the Ambu Bag is not being compressed by the contact element C-20. The bladder may be connected to the air line by a segmented air nipple.

It may be desirable to maintain the pulsatile air system as a closed system so that one or more animation bladders connected to the ports of the one or more umbilical cables operate to force back the air into the tubing through operation of the bladder in an elastic range and the weight of the animated tissue.

Figure 6:
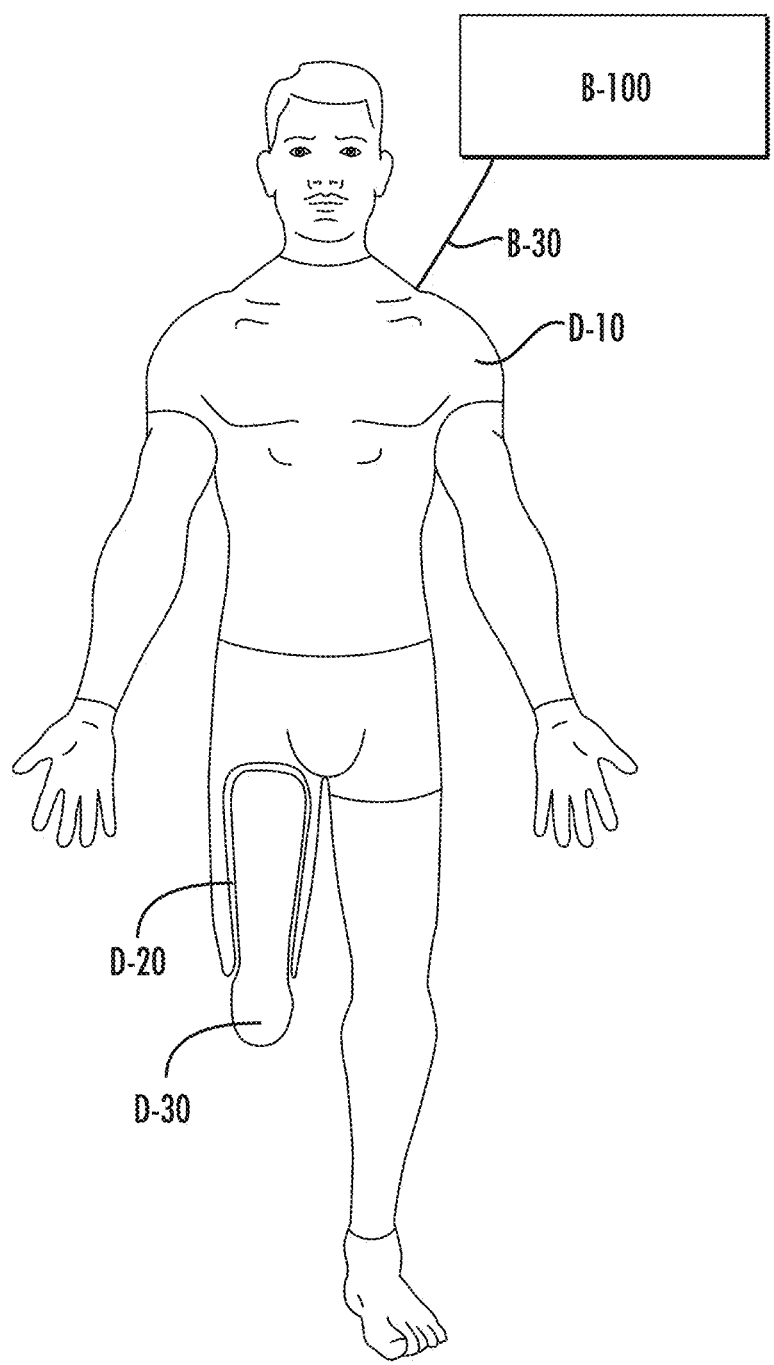
FIG. 6 shows a leg trauma mannequin D-10 that may be used in accordance with a non-limiting example.

FIG. 6 shows a leg trauma mannequin D-10 that includes the master controller B-100 and shows the shoulder portion D-10 and the leg area D-20 with an animated tissue portion D-30. The portion of the leg shown by D-20 and D-30 could be included as part of the animated tissue cassette.

In another embodiment, a more sophisticated system can be used to inflate and deflate the lungs, if desired. For example, a lung inflation/deflation system can include the following parts/sub-systems:

a. Programmable Logic Controller (PLC), such as an industrial computer that is designed to run 24/7 and to control machines, b. Human-Machine Interface (HMI), such as a touch-screen used to run/control the machine, c. Database of waveforms, where the waveforms reside in a non-volatile memory board or card and are accessed by the PLC. For heart beats, these waveforms can look like EKG traces, and for lung functions, including coughs and sneezes, these wave forms can look like audio recordings of the sound made during a cough or sneeze, d. Servo-Controller Power Amplifier, similar to a high-fidelity analog sound amplifier such as those found in a stereo systems, e. Servo Motor, where the term "servo" indicates that there is a feedback loop between the signal fed to the amplifier and the actual motion of the servo motor. The motor is an electric motor, which is connected to, and draws power from, the amplifier. In this manner, when the amplifier outputs a waveform, the motor connected to it will dutifully follow the exact waveform it is being tasked to reproduce, f. Actuator, where the servo motor drives a lead screw in order to convert rotational motion to linear motion. The actuator is attached to bellows.

g. Bellows, which form an expandable chamber (for example, a rubberized and expandable chamber) that pushes air out and draws air back in again, all in direct proportion to the linear motion of the lead screw, h. Air output, where air coming out of the bellows passes through an air hose connection that connects, directly or indirectly to one or more balloons attached to or present in a heart, or directly to the windpipe or bronchus of the lung(s), i. Air make-up valve, which valve opens when needed to begin a cycle. The opening and closing of the valve can be controlled by the PLC, j. An optional isolation valve, which functions as a liquid trap, and which can optionally include a filter, such as a HEPA filter. The isolation valve serves to prevent liquids from the animal heart, lung, or other biological components of the organ block from coming into the expensive bellows and decomposing. This valve can also be connected to the PLC, and, in one embodiment, can include a detector to determine whether liquids are present, and, optionally, can shut the system down if a pre-determined volume of liquid is detected.

k. Pressure transducer, which is an accurate pressure gauge, ideally connected to the PLC, used to size the heart or lungs (and thus prevent over-filling), and to scale the waveforms, l. Connection to the organs, such as "quick-connect" fittings which allow hoses to go from the pump system to the "driven" organ.

The "bellows" element can alternatively be a bladder, such as an automotive ride-leveler industrial bladder.

Simulated Heartbeat

In one embodiment, the invention relates to an animal or human heart, in which from one to four balloons are placed within from one and four ventricles (typically with only one balloon per ventricle). The inflation and contraction of the balloon replicates a heartbeat.

Anywhere from one to four balloons can used, in anywhere from one to four ventricles, depending on the type of surgery to be simulated. The balloons are inflated with air, and allowed to deflate. The inflation and deflation of the balloons causes real or fake blood to circulate through the simulated "patient," or at least those parts of which that are exposed to the surgeon undergoing training.

By placing the balloon(s) inside of the ventricles, one can reasonably accurately reproduce the movement of the heart. That is, the heart is a muscle that expands and contracts. The inflation of the balloon causes active expansion, and the deflation of the balloon causes only passive contraction.

The addition and removal of a gas to the balloon can be controlled using the same mechanisms described above for moving a gas into and out of the lungs, except that the gas is moved in and out of a balloon, placed inside the heart, rather than the lungs.

Figure 7:
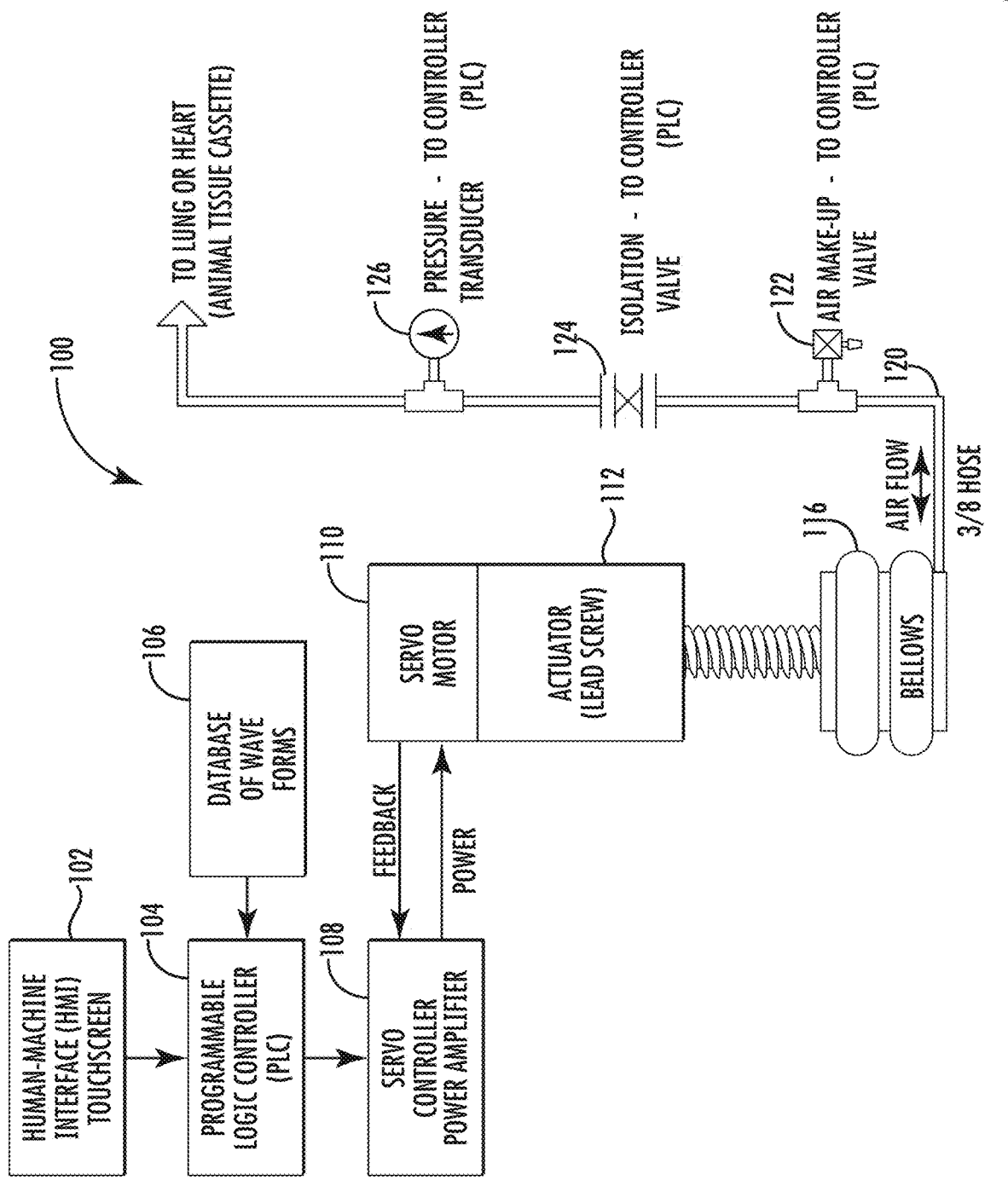
FIG. 7 is a block diagram of a system that can be used for inflating the lungs and/or heart in accordance with a non-limiting example.

A system 100 for inflating the lungs or the heart is shown in FIG. 7. A human-machine interface (HMI) 102 equipped with a touchscreen is connected to a programmable logic controller (PLC) 104, which includes or is attached to a database 106 of suitable waveforms. The waveforms can be used to simulate different types of breathing or different types of heartbeats. For example, a waveform can be used to simulate a normal heartbeat, cardiac arrest, various arrhythmias, and a flat-line (i.e., no pulse). Similarly, a waveform can be used to simulate normal breathing, shallow breathing, coughing, sneezing, sleep apnea, choking, and the like.

The PLC 104 is attached to a servo controller 108, which includes a power amplifier. The servo controller sends power to a servo motor 110, which sends feedback to the servo controller. The servo motor 110 is connected to an actuator 12, which actuator includes a means for translating energy into linear motion.

This can be, for example, a lead screw, ball screw, or rocker screw. Linear motion, or motion that occurs along a straight line, is the most basic type of movement. There are a number of linear energy devices enabling work functions like pumping. Electro mechanical actuators, which utilize an electric motor, can be used for these tasks. The motor turns a screw, such as a lead screw, ball screw, or rocker screw. Machine screw actuators convert rotary motion into linear motion, and the linear motion moves bellows up and down.

Bellows 116 are present in an actuator assembly to transfer pressure into a linear motion, or linear motion into pressure, depending on whether a gas is being blown into the lungs or heart, or being removed from the lungs or heart.

Edge welded bellows allow a long stroke, excellent media compatibility, and high temperature and pressure capabilities. Edge welded bellows also provide extreme flexibility in the design to fit size, weight, and movement requirements and allow the movement to be driven by internal or external forces. Bellows actuators can be used in valve applications, where pressure is internal or external to the bellows. Custom flanges, end pieces and hardware can be integrated into the assembly as appropriate.

The bellows is attached to an appropriately-sized hose 120, typically between ¼ and 1 inch in diameter, more typically ⅜ or ½ inch in diameter, which allows for the passage of a gas. The tubing can pass through an air make-up valve 122, an isolation valve 124, and a pressure transducer 126, any and all of which can be connected to the PLC. Once the appropriate pressure is attained, the gas can pass to the lung(s) and/or heart. The screw can be moved in one direction to fill the heart/lungs, and in the other direction to withdraw gas from the heart/lungs.

Master-Controller

The surgical simulator can be controlled using a master-controller. Master-controller B-100 is shown in FIG. 4 as a single component but it may in practice be distributed over several pieces of equipment.

Master-controller provides to the umbilical cables one or more pneumatic supplies. One pneumatic supply may be a closed loop system where air flow passes into and back from the umbilical cables on a periodic basis. For example, to support a staged reality of a beating heart, one pneumatic supply line may have air that pulses into the pneumatic line at 78 beats per minute. Optionally, this rate may be adjustable and may be altered to simulate a heart that stops or goes into some form of distress. Inflatable elements within the staged reality modules may thus expand and contract as paced by the pulses of air. Having a closed system avoids situations where staged reality module elements are over-filled. The amount of air provided by the pulse into the pneumatic line may be fine-tuned by the operator in order to adjust the simulation.

A pulsatile pump which better emulates a heartbeat than a sinusoidal oscillation of air in the pneumatic line may be included in the master-controller or the master-controller may receive pulsatile air from an external pulsatile pump. One suitable pulsatile pump is described in U.S. Pat. No. 7,798,815 to Ramphal et al. for a Computer-Controlled Tissue-Based Simulator for Training in Cardiac Surgical Techniques (incorporated herein by reference). A pulsatile pump may be created as indicated in FIG. 5.

Additional pneumatic supply lines at various target air pressures may be included in the umbilical cable.

The umbilical cable may include lines at ambient pressure (vented to ambient) or at a slight vacuum to allow expanded balloon-type structures to be emptied.

The master-controller B-100 (FIG. 4) may provide one or more fluids. The fluids may contain medical grade ethanol, dyes, and thickening agents. Medical grade ethanol has been found useful in maintaining the staged reality modules and in making the staged reality modules inhospitable to undesired organisms. Ethanol is useful compared to other chemicals which may be used to preserve tissue in that the ethanol maintains the pliability of the tissue so that it behaves like live tissue in a patient. A mixture with 40% ethanol works well, but the mixture should be made with an effort to avoid flammability when exposed to sparks or a cauterization process. Ethanol is desirable in that it does not produce a discernable odor to remind the participant that this is preserved tissue.

The storage life of some staged reality modules may be extended by storing them with fluid containing ethanol. A particular staged reality module that is not expected to be exposed to ignition sources should be made with an ethanol mixture that would be safe to have in proximity in a mannequin adjacent another staged reality module that did have ignition sources.

The master-controller may isolate the umbilical cable or cables from the fluid supply to allow the replacement of a module to allow the trainee to repeat a simulation with a new staged reality module.

Some staged reality modules may have prepared the module by connecting the venous and arterial systems together so that one pressurized fluid supply may animate both the arterial and venous vessels by filling them with colored fluid. The pressure for the fluid may be maintained by mere fluid head as an IV bag is suspended at a desired height above the master-controller or the master-controller may provide fluid at a given pressure using conventional components.

The umbilical cable may be provided with two blood simulating fluids, one being dyed to resemble arterial blood and a second dyed to resemble venous blood.

When the mannequin is to be used outdoors with a low ambient temperature, the staged reality module may have a circulation path that allows a warm fluid (approximately body temperature) to be circulated through the staged reality module and the umbilical cable to maintain the warmth of the tissue in the staged reality module. For staged reality modules that are expected to be completed within a short period of time, the staged reality module may be preheated to body temperature before the staged reality event and the fluids provided may be warmed to avoid cooling the staged reality module even when the fluid merely fills vessels in the staged reality module and is not circulated.

The umbilical cable may be provided with fluid lines for one or more non-blood fluids to be simulated such as digestive fluids, cerebral-spinal fluids, lymphatic fluids, fluids associated with pulmonary edema, pleural effusions, saliva, urine, or others fluids depending on the disease or trauma to be simulated.

The fluid and pneumatic connections used to connect the staged reality module to the various supplies on the umbilical cable may be any suitable connector for the desired pressure. Quick-connect fittings may be preferred so that the act of replacing a module with a similar module to allow the trainee to try it again may be accomplished quickly.

Depending on the quick-connect fitting used, the port may need to have blanks inserted to close the port to flow. When a module is to be connected to the port, the blank is removed and the module is connected.

The master-controller (B-100) may record the volume of fluids and gas provided to the particular lines or alternatively the pressure maintained on particular lines over time. This data record may be used to assess when a trainee effectively ligated a blood vessel or shut off some other structure such as a urinary tract.

The umbilical cable may include one or more instrument control cables. Control cables with common interface standards such as USB (Universal Serial Bus) may be used. The USB connection may be used to provide power to instruments and local logic devices in the staged reality modules. One of skill in the art will recognize that other data communication protocols may be used including RS-232 serial connection, IEEE 1394 (sometimes called Fire Wire or i.LTNK), and even fiber optic cable connections.

The USB connection allows for communication between a module and the master-controller. Depending on the staged reality presentation the communication may be to the module such as:

A) The master-controller (B-100) may send random or triggered commands for a staged reality component to twitch within a staged reality module.

B) The master-controller (B-100) may send a command to one or more staged reality modules to instigate quivering such as may be seen from a patient in shock. The staged reality module may implement quivering by opening and closing a series of small valves to alternatively connect a small balloon like structure to a high pressure gas via a port on the umbilical cable or to a vent line in the umbilical cable via the umbilical cable port. The valves providing the pressurized gas or venting of the balloon-like structure may be under the local control of logic within the staged reality module or they may be controlled directly from the master-controller.

C) The experience of staged reality may be increased by having more than one staged reality module quiver at the same time. Mannequins may make gross motions in response to pain such as sitting up or recoiling to add to the staged reality. This may startle the participant, but that may be a useful addition to the training.

The USB connection allows for communication from the staged reality module to the master-controller such as a time-stamp when the module detects the surgeon starting to cut into a portion of the module, pressure readings, accelerometer indications (respect for tissue).

The master-controller (B-100) may receive input from a simulation operator. The simulation operator may trigger adverse events that complicate the staged reality scenario such as a simulated cardiac event. The adverse event may be added to challenge a participant that has already demonstrated mastery.

The master-controller (B-100) may serve as part of a data collection system that collects data about the training of each particular participant so that the effectiveness of one training regime for one population of participants can be compared with the effectiveness of another training regime on another population of participants so that the differences of effectiveness can be quantified.

The master-controller (B-100) may have access to the training records for a particular participant in order to assess the need for additional repetitions of a particular training module.

Use of Bar Code Scanners

A bar code scanner B-60 can also be used to read bar codes on equipment or faux drug delivery devices to augment the simulation with recording the receipt of the therapy from the equipment or provision of a specific amount of a specific drug (even if no drug is actually delivered to the mannequin). This information may be used by the master-controller or communicated to one or more staged reality modules to alter the staged reality. For example, the intramuscular or intravenous delivery of a drug may alter the rate of bleeding, the heart rate, or some other parameter that impacts the presentation of the staged reality.

Representative Endoscopic Surgical Simulator

Endoscopic procedures can be simulated, for example, using the Endoscopy VR Simulator from CAE Healthcare. This simulator is a virtual reality endoscopic simulation platform that uses realistic, procedure-based content to teach cognitive and motor skills training. It is an interactive system with tactile feedback that permits learning and practice without putting patients at risk. The tissue, while not animal tissue, looks real, and 'moves' when it is touched. The virtual patient exhibits involuntary muscle contractions, bleeding, vital sign changes, etc., and the surgeon feels feedback resistance during the simulated procedure.

III. Robotic Surgical Instruments

In the systems described herein, one or more surgeons performs surgery on the animal tissue, organs, and/or organ blocks using robotic surgical instruments.

Typically, the robotic surgical devices include one or more arms, which control one or more tools, such as an endoscope (which provides the surgeon with the ability to see inside of the patient, and, typically, a tool selected from the group consisting of jaws, scissors, graspers, needle holders, micro-dissectors, staple appliers, tackers, suction irrigation tools, clip appliers, cutting blades, cautery probes, irrigators, catheters, suction orifices, lasers, and lights.

In robotically-assisted telesurgery, the surgeon typically operates a master controller to control the motion of surgical instruments at the surgical site from a location that may be remote from the surgical simulator (e.g., across the operating room, in a different room, or a completely different building from the surgical simulator).

The master controller B-100 usually includes one or more hand input devices, such as hand-held wrist gimbals, joysticks, exoskeletal gloves or the like. These control the movement of one or more of the robotic arms. Occasionally, line-of-sign/gaze tracking and oral commands are used to control movement of one or more of the robotic arms, and/or the audio/video components that transmit signal back to the surgeon.

Gaze tracking is described, for example, in U.S. Patent Publication No. 2014/0282196 by Zhao et al. A gaze tracker can be provided for tracking a user's gaze on a viewer. Preferably, the gaze tracker is a stereo gaze tracking system. An example of such a gaze tracking system is describe in U.S. Patent Application Ser. No. 61/554,741 entitled, "Method and System for Stereo Gaze Tracking." If the viewer only has a single two-dimensional display screen, however, any conventional gaze tracker may be usable with a video-based system preferred since it is non-contacting.

When the surgeon is in the same room as the robotic surgical device, these devices can be operatively coupled to the surgical instruments that are releasably coupled to a surgical manipulator near the surgical simulator ("the slave"). However, when the surgeon is remote from the actual room in which the surgery is taking place, these devices are coupled using the internet, or an intranet, preferably using some form of cloud computing.

In this case, the master controller B-100 controls the instrument's position, orientation, and articulation at the surgical site. The slave is an electro-mechanical assembly which includes one or more arms, joints, linkages, servo motors, etc. that are connected together to support and control the surgical instruments. In a surgical procedure, the surgical instruments (including an endoscope) may be introduced directly into an open surgical site, through an orifice, or through cannulas into a body cavity present in the animal tissue, organs and/or organ blocks.

For minimally invasive surgical procedures, the surgical instruments, controlled by the surgical manipulator, can be introduced into a simulated body cavity through a single surgical incision site, multiple closely spaced incision sites on the simulated body, and/or one or more natural orifices in the anatomy of the organ and/or organ block (such as through the rectum where a porcine or other animal gastro-intestinal system is used as the organ block).

For some minimally invasive surgical procedures performed through particularly small entry ports, multiple surgical instruments may be introduced in a closely gathered cluster with nearly parallel instrument shafts.

In one embodiment, the surgical systems and techniques maintain a common center of motion, known as a "remote center," at an area near the anatomical entry point. However, where there is a particularly narrow surgical incision or a particularly narrow natural orifice, such as an animal throat or cervix, this may result in the collision of the proximal ends of the surgical instruments. To control the surgical instruments while minimizing the occurrence of surgical instrument collisions, it may be desirable to use a robotic system such as that described in U.S. Patent Publication No. 2014/0236175 by Intuitive Surgical Operations, Inc.

A more detailed explanation of certain the components of robotic systems is provided below:

A robotic surgical system includes a master system, also referred to as a master or surgeon's console, for inputting a surgical procedure and a slave system, also referred to as a patient-side manipulator (PSM), for robotically moving surgical instruments at a surgical site within a patient. The robotic surgical system is used to perform minimally invasive robotic surgery. One example of a robotic surgical system architecture that can be used to implement the systems and techniques described in this disclosure is a da Vinci®. Surgical System manufactured by Intuitive Surgical, Inc. of Sunnyvale, Calif. Alternatively, a smaller scale robotic surgical system with a single manipulator arm may be suitable for some procedures. The robotic surgical system also includes an image capture system, which includes an image capture device, such as an endoscope, and related image processing hardware and software. The robotic surgical system also includes a control system that is operatively linked to sensors, motors, actuators, and other components of the master system and the slave system and to the image capture system.

The system is used by a system operator, generally a surgeon, who performs a minimally invasive simulated surgical procedure on a simulated patient. The system operator sees images, captured by the image capture system, presented for viewing at the master system. In response to the surgeon's input commands, the control system effects servo-mechanical movement of surgical instruments coupled to the robotic slave system.

The control system includes at least one processor and typically a plurality of processors for effecting control between the master system, the slave system, and the image capture system. The control system also includes software programming instructions to implement some or all of the methods described herein. The control system can include a number of data processing circuits (e.g., on the master system and/or on the slave system), with at least a portion of the processing optionally being performed adjacent an input device, a portion being performed adjacent a manipulator, and the like. Any of a wide variety of centralized or distributed data processing architectures may be employed. Similarly, the programming code may be implemented as a number of separate programs or subroutines, or may be integrated into a number of other aspects of the robotic systems described herein. In one embodiment, control system may support wireless communication protocols such as Bluetooth, IrDA, HomeRF, IEEE 802.11, DECT, and Wireless Telemetry.

The robotic surgical system can also include an instrument chassis that couples to the slave system. The instrument chassis provides a common platform for coupling surgical instruments and endoscope for introduction into an entry point on the simulated patient. In one embodiment, the entry point can be a mouth, where access to the throat or larynx is desired, the rectum where access to the gastrointestinal system, or, more particularly, to the colon, is desired, or previously-prepared or surgically created openings or orifices.

In one embodiment, the system can also include an instrument chassis having a proximal section and a distal section. The chassis supports an endoscope. Generally, the dimensions and shape of the chassis at its distal section are typically reduced compared to its proximal end, to minimize the volume of the surgical equipment near the surgical entry point. Instrument interfaces can be movably mounted to the proximal section of the instrument chassis. Surgical instruments can be mounted at the proximal end to the instrument interface. Surgical instruments can be mounted at its proximal end to the instrument interface. The interface drives movable components in the surgical instrument as described in U.S. Pat. No. 6,491,701 which is incorporated by reference herein in its entirety. The interface drives the instrument in a similar way. The surgical instruments are also movably coupled to the distal section of the chassis. The instrument interfaces are mounted to the proximal section of the chassis such that rotational and linear motion is permitted. Specifically, an instrument interface mounting or a flexible instrument shaft permits a pitch motion of the instrument interfaces relative to the chassis, a yaw motion of the instrument interfaces relative to the chassis and an insertion sliding motion of the instrument interfaces relative to the chassis. The system can function in a manner similar to the manner in which chopsticks operate, in that small motions at the proximal end of the tool, near a pivot location, can correspond to larger motions at the distal end of the tool for manipulating objects.

An actuation system operates the components of instrument, such as an end effector and various wrist joints. An actuation system operates the components of instrument, such as an end effector and various wrist joints. The actuation systems can include motors, actuators, drive systems, control systems, and other components for effecting controlling the instruments. An interface actuation system controls the movement of the instrument with respect to the chassis, and an interface actuation system controls the movement of the instrument with respect to the chassis. The surgical system can be configured to manipulate one, two, or more instruments.

Some robotic surgery systems use a surgical instrument coupled to a robotic manipulator arm and to an insertion linkage system that constrained motion of the surgical instrument about a remote center of motion aligned along the shaft of the surgical instrument and coincident with a patient entry point, such as an entry incision. Further details of these methods and systems are described in U.S. Pat. Nos. 5,817,084 and 6,441,577, which are incorporated by reference herein in their entirety.

Actuators can be operably coupled to interface discs. A more detailed description of the interface discs and their function in driving a predetermined motion in an attached surgical instrument is fully described, for example, in U.S. Pat. No. 7,963,913, filed Dec. 10, 2006, disclosing "Instrument Interface of Robotic Surgical System," which is incorporated by reference herein in its entirety.

Various embodiments of surgical instruments, end effectors, and wrist mechanisms are explained in detail in U.S. Pat. Nos. 5,792,135; 6,331,181; and 6,817,974, which are incorporated by reference herein in their entirety.

Software Control

One or more elements in embodiments described herein can be implemented in software to execute on a processor of a computer system such as control system. When implemented in software, the elements of the embodiments described herein are essentially the code segments to perform the necessary tasks. The program or code segments can be stored in a processor readable storage medium or device that may have been downloaded by way of a computer data signal embodied in a carrier wave over a transmission medium or a communication link. The processor readable storage device may include any medium that can store information including an optical medium, semiconductor medium, and magnetic medium. Processor readable storage device examples include an electronic circuit; a semiconductor device, a semiconductor memory device, a read only memory (ROM), a flash memory, an erasable programmable read only memory (EPROM); a floppy diskette, a CD-ROM, an optical disk, a hard disk, or other storage device, The code segments may be downloaded via computer networks such as the Internet, Intranet, etc.

The processes and displays presented may not inherently be related to any particular computer or other apparatus. Various general-purpose systems may be used with programs in accordance with the teachings herein, or it may prove convenient to construct a more specialized apparatus to perform the operations described. The required structure for a variety of these systems will appear as elements in the claims. In addition, the embodiments of the invention are not described with reference to any particular programming language. It will be appreciated that a variety of programming languages may be used to implement the teachings of the invention as described herein.

Surgeon's Remote Control of Instruments

As discussed above, in use, the surgeon must control a number of surgical instruments. This can be performed using, for example, gimbals, foot pedals, oral commands, and/or "gaze tracking," although gaze-tracking is not a popular method of controlling surgical instruments at the present time. Motions by the surgeon are interpreted by software, and a signal can be transmitted, either through a wire, or wirelessly, to a controller connected to the robotic instrument, which translates the signal into instructions for moving one or more robotic arms.

As the signal is received, and the robotic arms are moved, it is critically important that the surgeon can see how the instruments are moved, and how the instruments in turn affect the "patient." That is, if there is bleeding, changes in heartbeat or respiration, and the like, the physician must respond in a timely manner. Accordingly, a "live" video, and, optionally, audio feed is transmitted back to the surgeon.

It is critically important to minimize latency in the signal being passed back and forth between the surgeon and the robotic system. Ways to control latency are discussed in more detail below.

U.S. Pat. No. 6,659,939 entitled, "Cooperative Minimally Invasive Telesurgical System," which is incorporated herein by reference, provides additional details on a medical robotic system such as described herein.

Typically, a robotic system includes an image capture device, which is preferably a high-definition digital stereo camera that generates a video stream of stereo images captured at a frame rate of the camera, such as thirty frames per second. Each frame of stereo images includes a left stereo image and a right stereo image. In use, the image capture device captures video and, optionally, audio feed at the surgical site, providing one or more surgeons with real-time information on how the operation is proceeding.

The system uses a processor, programmed to process images received from the image capture device and display the processed images on a viewer. The viewer is preferably a stereo viewer having left and right display screens for respectively displaying left and right stereo images derived from the left and right stereo images captured by the image capture device.

A variety of input devices are provided to allow the surgeon(s) to control the robotic system. For example, user interfaces can include wrist gimbals, foot pedals, microphones, speakers, and gaze trackers. These input devices (also referred to as "masters") can also include any conventional computer input device, such as a joystick, computer mouse, keyboard, microphone, or digital pen and pad. Each of these devices can optionally be equipped with an on-off switch. The microphone facilitates user input to a voice recognition function performed by the processor, and the speaker can provide auditory warnings or action prompts to the user.

A gaze tracker can include eye tracking hardware in the viewer that communicates information related to such eye tracking to the processor. The processor processes the information to determine a gaze point of the user on a display screen of the viewer. In one example, the viewer may include one or more light sources, such as one or more infrared Light Emitting Diodes (IR LEDs) for directing light onto an eye of the user, a reflected light or image capturing device such as a Charge Coupled Device (CCD) camera, and one or more mirrors such as Dichroic mirrors for directing the reflected light from and/or image of the eye of the user to the reflected light or image capturing device. Information related to the reflected light or captured image can then be transmitted from the reflected light or image capturing device to the processor, which analyzes the information using known techniques to determine the gaze and gaze point of the user's eye on the viewer.

Tools are provided so that they may interact with objects at a surgical site. The tools and the image capture device are robotically manipulated by the robotic arms to which they are attached (also referred to as "slaves"). The tools are controlled by movement of the robotic arms, which in turn is controlled by the processor, which in turn receives signals from the surgeon(s) via signals sent by the input device(s).

The system can include one, two, or more input devices, and tools. The number of input devices and tools depends on what is needed at the time for performing the desired robotic surgery. The processor performs various functions in the robotic system, including controlling the movement of the robotic arms (and, hence, the robotic operation of the tools), as well as the image capture device in response to the surgeon's interaction with the input devices. The processor can also process images captured by the image capture device and send an appropriate signal for display on the viewer.

Although described as a processor, it is to be appreciated that the processor can be implemented by any combination of hardware, software, and firmware. Also, its functions as described herein may be performed by one unit or divided up among different components, each of which may be implemented in turn by any combination of hardware, software, and firmware. In performing its various tasks, the processor executes program code which is non-transitorily stored in memory.

The processor can also be used to perform a calibration function, where movements of one or more surgeons are calibrated based on user preferences.

If the user's gaze point is on an image of a robotically manipulated tool at the work site, then identification of the tool can readily be performed by, for example, using conventional tool tracking techniques and a previously determined transform which maps points in each tool's reference frame to a viewer reference frame. Additional details for tool tracking may be found, for example, in U.S. Patent Publication No. 2006/0258938 entitled, "Methods and System for Performing 3-D Tool Tracking by Fusion of Sensor and/or Camera Derived Data During Minimally Invasive Robotic Surgery," which is incorporated herein by reference. Additional details for reference frame transforms may be found, for example, in U.S. Patent Publication No. 2012/0290134 entitled, "Estimation of a Position and Orientation of a Frame Used in Controlling Movement of a Tool," which is incorporated herein by reference.

In addition to or in place of gaze tracking, the surgeon can identify the object to be viewed and/or controlled using any of the user input mechanisms provided, such as a Graphical User Interface (GUI) or a Voice Recognition System.

Once the object is identified, the object is highlighted in some fashion on the viewer. The processor can provide a signal to the surgeon, allowing the surgeon to confirm that the object that is highlighted is the correct object, using any appropriate input device. If the incorrect object is identified, the surgeon can adjust to this by recalibrating the instrument.

Some common ways to control multiple tools include having a surgeon select an action command, such as "IDENTIFY TOOL," which displays information on the tool on or adjacent an image of the tool on the viewer, and a command of "IDENTIFY MASTER," which identifies the master currently associated with the tool. The associated master in this case is the input device which controls robotic movement of the selected tool.

Another useful command is "STATUS" which provides status information for the tool being displayed on or adjacent an image of the tool on the viewer. The status information may include the remaining life of the tool in terms of hours, number of usages, or other maintenance and/or replacement measures. It may also include warnings if the usage reaches certain thresholds or certain conditions are met.

Another useful command is "SWAP TOOL," which allows the surgeon to control a different tool. One way to allow a surgeon to swap tools is to have a selectable icon displayed on the display screen of the viewer. The surgeon can select the selectable icon using an appropriate input device, such as a conventional computer mouse. Alternatively, the surgeon can use a command "SWAP MASTER" allowing the surgeon to select the icon of another master. This can disassociate the currently associated master from the tool and the master corresponding to the selected one of the selectable icons would be associated to the tool. The icon of the newly associated master would then be highlighted and user interaction with the newly associated master would now control movement of the tool.

Yet another useful command is "FOLLOW," which allows the image capture device to automatically move so that the working end of the selected tool remains in approximately the center of its Field of View (FOV). Additional details on such a coupled control mode may be found, for example, in U.S. Patent Publication No. 2010/0274087 entitled, "Medical Robotic System with Coupled Control Modes," which is incorporated herein by reference.

Additional commands can be used to control movement of the tool, the arm, and/or the image capture device, for example, commands made to correct direction, such as "UP", "DOWN," "RIGHT," "LEFT," "FORWARD," and "BACK" in three-dimensional space. The correctional action may be a correctional sizing, such as "INCREASE WIDTH," "DECREASE WIDTH," "INCREASE LENGTH," "DECREASE LENGTH," "INCREASE DEPTH," and "DECREASE DEPTH" for a three-dimensional box.

Additional commands can be used to control the image capture device. For example, "ADJUST FOCUS," "ZOOM-IN" or "ZOOM-OUT" can be used for the well-understood purposes associated with these commands. Similarly, a command "ADJUST BRIGHTNESS" can be used to automatically adjust the brightness function on the image capture device, for example, as a function of a distance from the image capturing end of the image capture device to an object whose image is being viewed at the time inside the displayed box on the viewer. Commands of "INCREASE RESOLUTION" or "DECREASE RESOLUTION" can be used to adjust the resolution of the image captured by the image capture device.

Other commands that a surgeon may wish to use include "CONSTRAIN TOOLS" to establish a virtual constraint in which the processor, acting as a controller for robotically manipulating the tools, responds to such user selected action command by constraining commanded movement of the working ends of those tools to only move within an area/volume of the work site corresponding to the area/volume of the box defined on the viewer. Alternatively, such constraint may be to prohibit the tools from entering an area/volume of the work site corresponding to the area/volume of the box. As other examples, certain image characteristics in a region of interest defined by the box may be adjusted, images of objects within the box may be zoomed-in or zoomed-out, and the image within the box may be displayed on an auxiliary viewer that is being viewed at the time by an assistant.

These are merely examples of useful commands. Those of skill in the art will appreciate that there are a number of other suitable actions that can be defined and performed.

Additional language on robotic systems that can be used in the systems described herein can be found in U.S. Patent Publication No. 2014/0236175 by Intuitive Surgical Operations, Inc.

IV. Remote Control of Robotic Systems

Telesurgery can be used in order for a surgeon to perform surgery from a distance, or to provide consultation or education to another surgeon performing a real operation, where an expert surgeon may watch watching the real operation and instruct the doctor, where the surgery is performed on a surgical simulator. One or more of the surgeons can be located at a remote location, where a robot is used to carry out the surgery, using hand movements and other input from the surgeon at the remote location via a tele-robotic unit.

The robot can move the real endoscope or other surgical device according to the movements of the surgeon performed using the input devices described above.

A simulated procedure can be taught by one surgeon to another surgeon at a remote location in real-time using a video data feed. For example, a surgeon using a real endoscope looking at the surgical simulator, with real animal organs, which, depending on the organ, can beat like a beating heart or breathe like a living set of lungs, can move the endoscope inside the "orifices" of the simulated human patient, can receive video corresponding to data transmitted electronically to a remote point (e.g., from the Mayo Clinic or via the Internet), and an expert watching the operation in real-time can show the actual doctor performing the simulated surgery how to conduct the operation, or provide particular guidance to the other surgeon performing the operation. This guidance can be provided on a display screen in the actual operating room while the surgeon is operating on the simulated patient.

A storage library can be implemented, in which a library of simulations, problems encountered, etc. are stored for later retrieval by a student or surgeon. For example, an expert surgeon teaching surgery using the simulator can simulate a biopsy or how to use a laser or particular surgical device on a simulated patient with a particular abnormality or operation to be performed. This is particularly true where organs or organ blocks are selected which include the particular abnormality.

The present invention can thus be used in a telerobotics application for teaching surgery on a simulated surgical device, such as those described herein.

Force feedback may be provided to the surgeon by the instructor, where the instructor takes over control of the robotic instruments from the student.

A virtual surgery system according to an embodiment of the present invention can be used in which an input device is used by a user to perform virtual surgery as described above. The input devices can include one or more of a mouse device, a seven dimensional joystick device, a full size simulator, etc. The input device can also one or more of include a keyboard, a standard mouse, a three dimensional mouse, a standard joystick, a seven dimensional joystick, or a full size simulator with a full size mock-up of a medical or other industrial type instrument. Additionally, any of these input devices can be used in the present invention with force feedback being performed.

The signals, originating when the surgeon operates an input device, are transmitted through a wired or wireless connection, to a processor on the robotic surgical instrument, which is then translated to a command that moves the robotic arm, and the surgical tool attached to the arm.

The control of the telerobotic system is ideally handled in a manner which minimizes latency, so there is little perceived delay between the surgeon remotely directing the movement of the tool, the movement of the tool, and the video and, optionally, audio feed back to the surgeon.

One example of a suitable telerobotic communication system is described, for example, in U.S. Patent Publication No. 2013/0226343 by Baiden. Such a system can include a teleoperation center to transmit control data and receive non-control data by wireless connection to and from a surgeon, operating one or more input devices, and indirectly to and from the actual robotic system including the robotic arms and tools attached thereto.

The device used by the surgeon can include includes a transceiver for receiving and transmitting control and non-control data, respectively, and also a repeater for relaying control data to a robotic surgical system, and relaying non-control data back to the teleoperation center. The system can also include wireless repeaters to extend the communications distance between the site where the surgeon is controlling the robotic instruments, and the site where the instruments are located.

The electronics of the system can use control-specific input/output streams, and are, ideally, low latency. The electronics are preferably designed to be high speed and fast processing and to minimize latency. The system can include at least two main communication components: the first is a long distance directional transmitter/receiver, and the second is a transceiver.

A video system can perform image processing functions for, e.g., captured endoscopic imaging data of the surgical site and/or preoperative or real time image data from other imaging systems external to the simulated patient. The imaging system outputs processed image data (e.g., images of the surgical site, as well as relevant control and patient information) to the surgeon at the surgeon's console. In some aspects the processed image data is output to an optional external monitor visible to other operating room personnel or to one or more locations remote from the operating room (e.g., a surgeon at another location may monitor the video; live feed video may be used for training; etc.).

Remote surgery (also known as telesurgery) is the ability for a doctor to perform surgery on a patient even though they are not physically in the same location. Remote surgery combines elements of robotics, cutting edge communication technology such as high-speed data connections and elements of management information systems. While the field of robotic surgery is fairly well established, most of these robots are controlled by surgeons at the location of the surgery.

Remote surgery allows the physical distance between the surgeon and the simulated patient to be immaterial. It allows the expertise of specialized surgeons to be available to students worldwide, without the need for the surgeons to travel beyond their local hospital to meet the surgeon, or to a remote site where a simulated surgical center may be. A critical limiting factor is the speed, latency and reliability of the communication system between the surgeon and the robotic instrument where simulated patient is located.

Cloud Computing

Any communications approach which provides the desired low latency can be used, but cloud computing is preferred.

A cloud computing system is one where some part of the computing happens remotely through the Internet (aka "the cloud"). In the case of robotic surgery conducted remotely, this will involve a surgeon inputting information regarding the movement of robotic equipment using essentially the same tools available to the surgeon when he or she is in the same room as the robotic surgical equipment (i.e., gimbals, controllers, foot pedals, line of sight devices, and voice commands), but sending the signals over the internet, so that the controls are translated into movement of the robotic arms at the remote site.

Simultaneously, or substantially so, video signals, showing the movement of the robotic arms, and providing a video feed of the surgery taking place, is transmitted back to the surgeon.

The data is, in effect, running on a server in a data center connected to the internet, perhaps thousands of miles away, rather than on a local computer.

In one embodiment, the cloud computing experience is perceptually indistinguishable from a local computing experience. That is, when the surgeon performs an action, the surgeon experiences the result of that action immediately, just as if the surgery was being performed in the same room as the robotic device, and can view the results on a video monitor.

In one embodiment, the cloud computing system is an "OnLive" system (now owned by Sony). The OnLive system for "interactive cloud computing" is one in which the "cloud computing" (i.e., computing on a server in the internet) is indistinguishable from what computing experience would be if the application were running entirely on a local computer. This is done by minimizing latency.

It is critically important to minimize latency, because robotic surgery requires perceptually instantaneous response times, which can otherwise be difficult to achieve, given the complexity, erratic motion and unpredictability of real-time visual imagery.

The vast majority of current services, applications and media available on the internet use existing infrastructure and its inherent limitations exceedingly well. These applications generally are those that are largely unidirectional and with loose response deadlines: they download software, content and media objects based on limited amount of user interaction. Other applications from the web download executable programs which are then run in a user's local machine environment, using the internet only for a limited exchange of data and commands. This methodology requires an end-user machine to have the full extent of computing power (e.g., processor, memory, storage and graphics) as well as entire programs to be downloaded into the local user environment. With an Interactive Cloud Computing ("ICC") system, expensive hardware, software, data, and complex processes can stay in the data center. This reduces the need, cost, complexity and energy consumption of end user computers. Further, by sharing the central systems among many users, any negative impacts associated with those systems are divided amongst the many users.

The cloud computing system not only has to provide adequate bandwidth to allow data regarding the movement of the robotic arms, and a live video feed of the operation as it is being conducted remotely, it also has to quickly process data (using interactive, cloud-based systems) and then provide (i.e., render) the resulting audio/video in the data center, compress the audio/video, and condition the compressed audio/video to be transmitted to the end user as quickly as possible, simultaneously as the user is providing real-time feedback (via gimbals, foot pedals, mice, line-of-sight, voice control, and/or other methods of controlling the movement of the robotic arms) based on those real-time-transmitted sounds and images.

The performance metrics involve bandwidth (i.e., data throughput). Generally, the more bandwidth, the better the experience. A 100 Mbps connection is much more desirable than a 5 Mbps connection because data downloads 20 times faster. For this reason, the systems described herein preferably have a bandwidth of at least 5 Mbps, more preferably, at least about 50 Mbps, and even more preferably, at least about 100 Mbps.

That said, with ICC, as long as the bandwidth required for the resolution of the video display, audio stream, and transmission of data relative to movement of the robotic arms has been met, there may not be much need for additional bandwidth. For example, if a user has a 1280×720p@60 frame/second (fps) HDTV display and stereo audio, a 5 Mbps connection will deliver good sound and video quality, even with highly interactive content, like the control of robotic arms for a remote surgical instrument. A 10 Mbps connection will fully support 1920×1080p@60 fps HDTV, a cell phone-resolution screen can be supported with 400 Kbps, and so on.

One significant aspect of the online-computing experience is that there be constant availability of data transfer. Commercial ISP connections often are rated in terms of availability (e.g., percentage of downtime, and sometimes with further statistical guarantees). For example, one can purchase a fixed downstream connection speed, for example, rated at 1.5 Mbps, using a T1 line or a fractional T1 line, or can use a cable modem connection that provides "up to" 18 Mbps downstream when a high-reliability application (e.g., an IP telephone PBX trunk line) is at stake. Although the cable modem connection is a vastly better value most of the time, because cable modem connections are typically not offered with availability guarantees, the business may not be able to risk the loss of its phone service if the cable modem connection "goes down" or if the bandwidth drops precipitously due to congestion.

While in other uses for data transfer, availability requirements may be less stringent, and users can tolerate Internet Service Provider ("ISP") connections that occasionally go down or are impaired (e.g., from congestion), this is not the case with telerobotics.

With telesurgery, availability is extremely important. The loss of a internet connectivity can be crippling when attempting to perform a simulated surgery, particularly where the "patient" can experience bleeding, and changes on breathing rate and heartbeat, simulating a failed surgical procedure, or an error that must quickly be corrected.

Performance metrics which are particularly relevant for telesurgery include:

1. Latency: the delay when packets transverse the network, measured using Round Trip Time (RTT). Packets can be held up in long queues, or delayed from taking a less direct route to avoid congestion. Packets can also be reordered between the transmission and reception point. Given the nature of most existing internet applications, latency is rarely noticed by users and then only when latency is extremely severe (seconds). Now, users will be noticing and complaining about latencies measured in milliseconds because of the accumulation of latency as messages route through the internet, and the immediate-response nature of interactive cloud computing.

2. Jitter: random variations in latency. Prior-technology internet applications used buffering (which increased latency) to absorb and obscure jitter. As a result, users have not noticed or cared about jitter, and the common preconception is that jitter is a technical detail that has no impact on user experience or the feasibility of provisioning internet applications. With interactive cloud computing, excessive jitter can have a significant impact on user experience and perceived performance, ultimately limiting the range of applications.

3. Packet Loss: data packets lost in transmission. In the past, almost all internet traffic was controlled by TCP (Transmission Control Protocol), which hides packet losses by asking for retransmissions without the user's knowledge. Small packet losses come with small increases in latency and reductions in bandwidth, essentially invisible to users. Large packet losses (several percent and up) felt like a "slow network" not a "broken network." With interactive cloud computing the additional round-trip latency delay incurred by requesting a resend of a lost packet potentially introduces a significant and noticeable lag.

4. Contention: multiple users competing for the same bandwidth on an ISP's network in excess of the network's capacity, without a fair and consistent means to share the available throughput. As applications and use of internet infrastructure continue to grow, old assumptions about the rarity or improbability of contention are being overturned. Contention leads to exacerbation in all three areas: latency, jitter and packet loss, mentioned above.

It can be important to minimize all of these aspects.

When the surgeon performs an action on a surgical instrument connected to OnLive (e.g., moves an input device), that action is sent up through the internet to an OnLive data center and routed to a server that is controlling the robotic instrument the surgeon is using. The processor computes the movement of the robotic instrument being controlled by the input device, based on that action, then the signal is quickly compressed from the server, and the signal is translated by a processor into movement of a robotic tool. Similarly, video, and, optionally, audio feed is compressed, transmitted, decompressed, and displayed on the surgeon's video display. The signals can be decompressed using a controller (for example, a PC, Mac or OnLive MicroConsole™). The entire round trip, from the time the input device is manipulated to the time the display or TV is updated is so fast that, perceptually, it appears that the screen is updated instantly and that the surgery is actually being performed locally.

The key challenge in any cloud system is to minimize and mitigate the issue of perceived latency to the end user.

Latency Perception

Every interactive computer system that is used introduces a certain amount of latency (i.e., lag) from the point the surgeon performs an action and then sees the result of that action on the screen. Sometimes the lag is very noticeable, and sometimes it isn't noticeable. However, even when the brain perceives response to be "instantaneous," there is always a certain amount of latency from the point the action is performed and the display shows the result of that action. There are several reasons for this. To start with, when you press a button, or otherwise activate an input device, it takes a certain amount of time for that button press to be transmitted to the processor (it may be less than a millisecond (ms) with a wired controller or as much as 10-20 ms when some wireless controllers are used, or if several are in use at once). Next, the processor needs time to process the button press. So, even if the processor responds right away to a button action, and moves the robotic arm, it may not do so for 17-33 ms or more, and it may take another 17-33 ms or more for the video capture at the surgical site to reflect the result of the action.

Depending on the system, the graphics hardware, and the particular video monitor, there may be almost no delay, to several frame times of delay. Since the data is being transmitted over the cloud, there typically is some delay sending the data to other surgeons watching and/or participating in the surgical procedure.

So, in summary, even when the system is running on a local machine, there is always latency. The question is simply how much latency. As a general rule of thumb, if a surgeon sees a response within 80 ms of an action, not only will the surgeon perceive the robotic arm as responding instantaneously, but the surgeon's performance will likely be just as good as if the latency was shorter, and as a result, 80 ms is the desired "latency budget" for the systems described herein. That is, the system, which can be an OnLive system, has up to 80 ms to: send a controller action from the surgeon's location, through the internet to an OnLive data center, route the message to the OnLive server that controls the robotic arms, have a processor on the robotic system calculate the next movement of the robotic arm, while simultaneously outputting video and, optionally, audio feeds, which can be compressed, route the optionally compressed feeds through the internet, then decompress the feed, if it was compressed, at the surgeon's video display. Ideally, this can be carried out at video feed rate of at least 60 fps, with HDTV resolution video, over a consumer or business internet connection.

Over Cable and DSL connections, OnLive is able to achieve this if the surgeon and the remote surgical site are located within about 1,000 miles of the OnLive data center. So, through OnLive, a surgeon who is 1,000 miles away from a data center can perform remote surgery, and display the results of the surgery on one or more remote video displays, running on a server in the data center. Each surgeon, whether it is the surgeon or surgeons performing the simulated surgical procedure, or one or more students observing the procedure, will have the perception as if the surgery were performed locally.

OnLive's Latency Calculations

The simplified diagram below shows the latencies encountered after a user's action in the home makes it way to an OnLive data center, which then generates a new frame of the video game and sends it back to the user's home for display. Single-headed arrows show latencies measured in a single direction. Double-headed arrows show latencies measured roundtrip.

Figure 8:
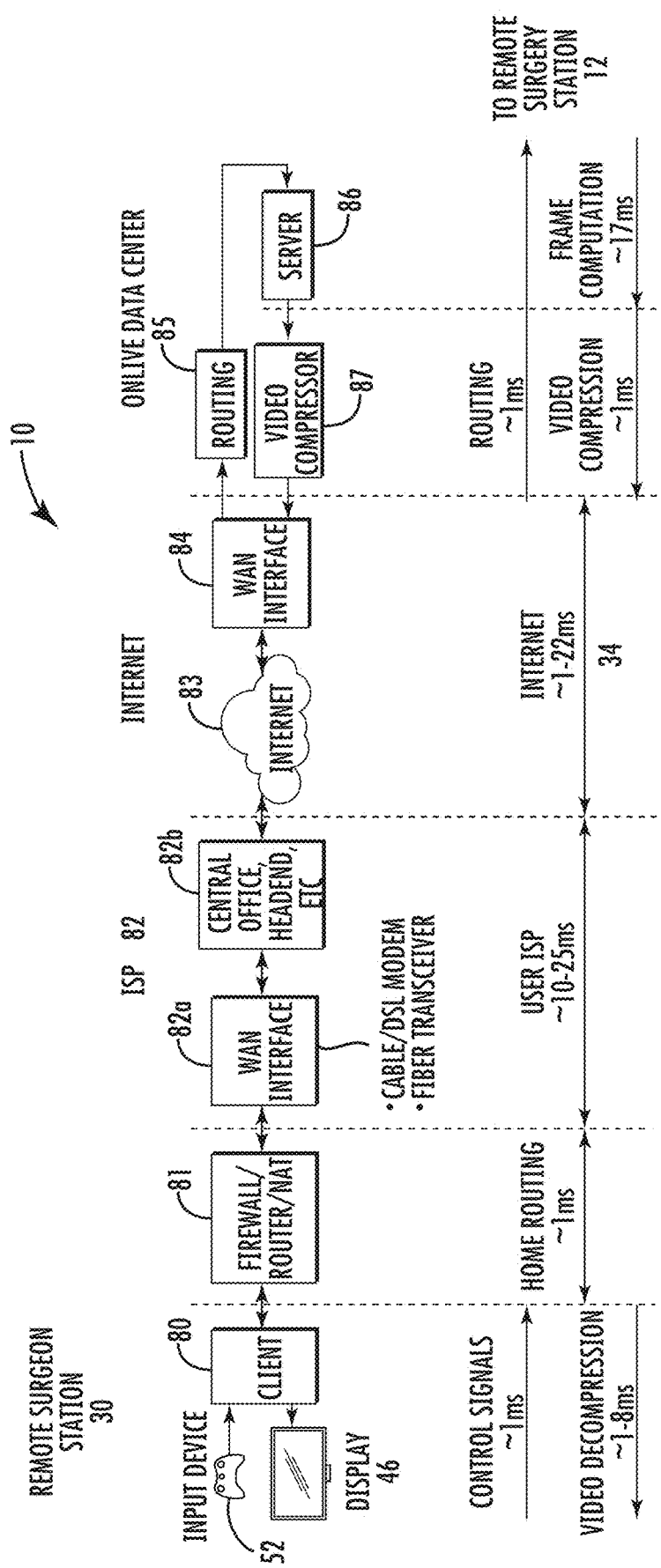
FIG. 8 shows an example of the flow of data to and from a surgeon to a surgical center, via an OnLive data center that may be used in accordance with a non-limiting example.

FIG. 8 shows the flow of data from the surgeon to the surgical center, via an OnLive data center. As illustrated in FIG. 8, the input device could correspond to a robotic surgeon station 30. The input device could be the controls 52 of FIG. 1 and connects to the client 80 with a connection to a firewall/router/NAT 81 and to the internet service provider 82 that includes a WAN interface 82*a* and a central office and head end 82*b*. It connects to the internet 83 and a WAN interface 84 that in turn connects to the OnLive data center with a routing center 85 including a router that connects to a server 86 and video compressor 87. At the client 80 video decompression occurs. This type of system is applicable for use with the telerobotic surgery system.

ISP Latency

Potentially, the largest source of latency is the "last mile" latency through the user's Internet Service Provider (ISP). This latency can be mitigated (or exacerbated) by the design and implementation of an ISP's network. Typical wired consumer networks in the US incur 10-25 ms of latency in the last mile, based on OnLive's measurements. Wireless cellular networks typically incur much higher last mile latency, potentially over 150-200 ms, although certain planned 4G network technologies are expected to decrease latency. Within the internet, assuming a relatively direct route can be obtained, latency is largely proportional to distance, and the roughly 22 ms worst case round-trip latency is based on about 1000 miles of distance (taking into account the speed of light through fiber, plus the typical delays OnLive has seen due to switching and routing through the internet.

Ideally, the data center and surgical center that are used will be located such that they are less than 1000 miles from each other, and from where a surgeon will be remotely accessing the robotic system. The compressed video, along with other required data, is sent through the internet back and forth from the surgeon to the robotic system. Notably, the data should be carefully managed to not exceed the data rate of the user's internet connection, as such could result in queuing of packets (incurring latency) or dropped packets.

Video Decompression Latency

Once the compressed video data and other data is received, then it is decompressed. The time needed for decompression depends on the performance of the system, and typically varies from about 1 to 8 ms. If there is a processing-constrained situation, the system will ideally will select a video frame size which will maintain low latency.

The system typically also includes controllers coupled to the articulate arms by a network port and one or more interconnect devices. The network port may be a computer that contains the necessary hardware and software to transmit and receive information through a communication link in a communication network.

The control units can provide output signals and commands that are incompatible with a computer. The interconnect devices can provide an interface that conditions the signals for transmitting and receiving signals between the control units and the network computer.

It is to be understood that the computer and/or control units can be constructed so that the system does not require the interconnect devices. Additionally, the control units may be constructed so that the system does not require a separate networking computer. For example, the control units can be constructed and/or configured to directly transmit information through the communication network.

The system can include a second network port that is coupled to a robot/device controller(s) and the communication network. The device controller controls the articulate arms. The second network port can be a computer that is coupled to the controller by an interconnect device. Although an interconnect device and network computer are described, it is to be understood that the controller can be constructed and configured to eliminate the device and/or computer.

The communication network can be any type of communication system including but not limited to, the internet and other types of wide area networks (WANs), intranets, local area networks (LANs), public switched telephone networks (PSTN), integrated services digital networks (ISDN). It is preferable to establish a communication link through a fiber optic network to reduce latency in the system. Depending upon the type of communication link selected, by way of example, the information can be transmitted in accordance with the user datagram protocol/internet protocol (UDP/IP) or asynchronous transfer mode/ATM Adaptation Layer 1 (ATM/AAL1) network protocols. The computers 140 and 150 may operate in accordance with an operating system sold under the designation VxWorks by Wind River. By way of example, the computers can be constructed and configured to operate with 100-base T Ethernet and/or 155 Mbps fiber ATM systems.

A mentor control unit can be accompanied by a touchscreen computer and an endoscope interface computer 158, where the touchscreen computer can be a device sold by Intuitive under the trademark HERMES. The touchscreen allows the surgeon to control and vary different functions and operations of the instruments. For example, the surgeon may vary the scale between movement of the handle assemblies and movement of the instruments through a graphical user interface (GUI) of the touchscreen. The touchscreen may have another GUI that allows the surgeon to initiate an action such as closing the gripper of an instrument.

The endoscope computer may allow the surgeon to control the movement of the robotic arm and the endoscope. Alternatively, the surgeon can control the endoscope through a foot pedal (not shown). The endoscope computer can be, for example, a device sold by Intuitive under the trademark SOCRATES. The touchscreen and endoscope computers may be coupled to the network computer by RS232 interfaces or other serial interfaces.

A control unit can transmit and receive information that is communicated as analog, digital or quadrature signals. The network computer may have analog input/output (I/O), digital I/O and quadrature interfaces that allow communication between the control unit and the network. By way of example, the analog interface may transceive data relating to handle position, tilt position, in/out position and foot pedal information (if used). The quadrature signals may relate to roll and pan position data. The digital I/O interface may relate to cable wire sensing data, handle buttons, illuminators (LEDs) and audio feedback (buzzers).

The position data is preferably absolute position information. By using absolute position information the robotic arms can still be moved even when some information is not successfully transmitted across the network. If incremental position information is provided, an error in the transmission would create a gap in the data and possibly inaccurate arm movement. The network computer may further have a screen and input device (e.g. keyboard) that allows for a user to operate the computer.

On the "patient" side, there is also a network and control computer. The controller may include separate controllers. The controller can receive input commands, perform kinematic computations based on the commands, and drive output signals to move the robotic arms and accompanying instruments to a desired position. The controller can receive commands that are processed to both move and actuate the instruments. Controller can receive input commands, perform kinematic computations based on the commands, and drive output signals' to move the robotic arm and accompanying endoscope.

Controllers can be coupled to the network computer by digital I/O and analog I/O interfaces. The computer may be coupled to the controller by an RS232 interface or other serial type interfaces. Additionally, the computer may be coupled to corresponding RS232 ports or other serial ports of the controllers. The RS232 ports or other serial ports of the controllers can receive data such as movement scaling and end effector actuation.

The robotic arms and instruments contain sensors, encoders, etc. that provide feedback information including force and position data. Some or all of this feedback information may be transmitted over the network to the surgeon side of the system. By way of example, the analog feedback information may include handle feedback, tilt feedback, in/out feedback and foot pedal feedback. Digital feedback may include cable sensing, buttons, illumination and auditory feedback. The computer can be coupled to a screen and input device (e.g. keyboard). Computers can packetize the information for transmission through the communication network. Each packet may contain two types of data, robotic data and other needed non-robotic data. Robotic data may include position information of the robots, including input commands to move the robots and position feedback from the robots. Other data may include functioning data such as instrument scaling and actuation.

Because the system transmits absolute position data the packets of robotic data can be received out of sequence. This may occur when using a UDP/IP protocol which uses a best efforts methodology. The computers are constructed and configured to properly treat any "late" arriving packets with robotic data. For example, the computer may sequentially transmit packets 1, 2 and 3. The computer may receive the packets in the order of 1, 3 and 2. The computer can disregard the second packet. Disregarding the packet instead of requesting a re-transmission of the data reduces the latency of the system. It is desirable to minimize latency to create a "real time" operation of the system.

It is preferable to have some information received in strict sequential order. Therefore the receiving computer will request a re-transmission of such data from the transmitting computer if the data is not errorlessly received. The data such as motion scaling and instrument actuation must be accurately transmitted and processed to insure that there is not an inadvertent command.

The computers can multiplex the RS232 data from the various input sources. The computers can have first-in first-out queues (FIFO) for transmitting information. Data transmitted between the computer and the various components within the surgeon side of the system may be communicated, for example, through a protocol provided by Intuitive under the name HERMES NETWORK PROTOCOL (HNP) Likewise, information may be transmitted between components on the patient side of the system in accordance with HNP.

In addition to the robotic and non-robotic data, the patient side of the system will transmit video data from the endoscope camera. To reduce latency in the system, the video data can be multiplexed with the robotic/other data onto the communication network. The video data may be compressed using conventional JPEG, etc., compression techniques for transmission to the surgeon side of the system.

Either computer can be used as an arbitrator between the input devices and the medical devices. For example, one computer can receive data from both control units. The computer can route the data to the relevant device (e.g. robot, instrument, etc.) in accordance with the priority data. For example, control unit may have a higher priority than control unit. The computer can route data to control a robot from control unit to the exclusion of data from control unit so that the surgeon at has control of the arm.

As an alternate embodiment, the computer cam be constructed and configured to provide priority according to the data in the SOURCE ID field. For example, the computer may be programmed to always provide priority for data that has the source ID from a control unit. The computer may have a hierarchical tree that assigns priority for a number of different input devices.

Alternatively, the computer can function as the arbitrator, screening the data before transmission across the network. The computer may have a priority scheme that always awards priority to one of the control units. Additionally, or alternatively, one or more of the control units may have a mechanical and/or software switch that can be actuated to give the console priority. The switch may function as an override feature to allow a surgeon to assume control of a procedure.

In operation, the system initially performs a start-up routine, typically configured to start-up with data from the consoles. The consoles may not be in communication during the start-up routine of the robotic arms, instruments, etc. therefore the system does not have the console data required for system boot. The computer may automatically drive the missing console input data to default values. The default values allow the patient side of the system to complete the start-up routine. Likewise, the computer may also drive missing incoming signals from the patient side of the system to default values to allow the control units to boot-up. Driving missing signals to a default value may be part of a network local mode. The local mode allows one or more consoles to "hot plug" into the system without shutting the system down.

Additionally, if communication between the surgeon and patient sides of the system are interrupted during operation the computer will again force the missing data to the last valid or default values as appropriate. The default values may be quiescent' signal values to prevent unsafe operation of the system. The components on the patient side will be left at the last known value so that the instruments and arms do not move.

Once the start-up routines have been completed and the communication link has been established the surgeons can operate the consoles. The system is quite useful for medical procedures wherein one of the surgeons is a teacher and the other surgeon is a pupil. The arbitration function of the system allows the teacher to take control of robot movement and instrument actuation at anytime during the procedure. This allows the teacher to instruct the pupil on the procedure and/or the use of a medical robotic system.

Additionally, the system may allow one surgeon to control one medical device and another surgeon to control the other device. For example, one surgeon—may move the instruments while the other surgeon moves the endoscope, or one surgeon may move one instrument while the other surgeon moves the other instrument. Alternatively, one surgeon may control one arm(s), the other surgeon can control the other arm(s), and both surgeons may jointly control another arm.

One or more of the control units can have an alternate communication link. The alternate link may be a telecommunication network that allows the control unit to be located at a remote location while control unit is in relative close proximity to the robotic arms, etc. For example, control unit may be connected to a public phone network, while control unit is coupled to the controller by a LAN. Such a system would allow telesurgery with the robotic arms, instruments, etc. The surgeon and patient sides of the system may be coupled to the link by network computers.

The control system can allow joint control of a single medical instrument with handles from two different control' units. The control system can include an instrument controller coupled to a medical instrument. The instrument controller can minimize the error between the desired position of the medical instrument and the actual position of the instrument.

In some embodiments, a patient has image data scanned into the system, and during a simulation or a real surgery operation, a portion of the display screen shows a prerecorded expert simulation via video tape, CDROM, etc., or a real-time tutorial by another doctor.

Telesurgery can be performed, in which a surgeon moves an input device (e.g., a full-size virtual scope or instrument) of a simulator while a robot actually performs a real operation based on the simulated motions of a surgeon at a remote location.

Telesurgery can be used in a teaching or testing embodiment, in which the virtual surgery device or other testing device questions via text and specific task questions. For example, in a medical embodiment, the virtual device might ask a test taker to go to a particular location in the anatomy and then perform a biopsy. Questions may be inserted in the test before, during or after a particular operation (such as a bronchoscopy). A multitude of tasks may be required of a student during the test procedure. The test taker may chose between different modes, such as an illustration, practice or exam mode.

In a typical operating room or training facility, several high-resolution video monitors are placed such that the surgical team can see the operation from the perspective of the operating surgeon (usually presented as a conventional 2-D image) as well as see the screen displaying the vital signs of the patient. Frequently, there are cameras positioned to record the entire operating theater to show to relative positions of the key players, such as anesthesiologists, nurses, physician assistants and training residents.

In training systems that do not use real animal tissue, computer-rendered images are displayed in lieu of actual tissue to represent the target of the surgical procedure. These images can be made to look extremely life-like. However, a trained medical professional can instantly distinguish between a computer-generated image of an operation versus a real operation performed on either living or non-living real tissue. The computer-generated image, however well-executed and made to appear as if it were moving, lacks the inherent differences that exist between multiple examples of real animals, such as those based on genetic diversity within the same species or even within the same litter.

The computer-generated image can offer substantial benefits in the training process in the same way that a well-drawn picture of an anatomical feature can help guide a surgeon to identify specific structures during the operation and during the pre- and post-operative imaging process. Specifically, drawing or rendering an anatomical feature or structure, without the naturally-occurring bleeding and spatial contortion sometimes present due to the viewing angle or viewing access, can offer a student substantial "clarity"

and allow the student to learn how to translate the images found in an anatomy atlas such as Gray's Anatomy.

In one embodiment of the telerobotic simulation system described herein, the video image of the operation as seen by the surgeon (performed on animated real animal tissue) is shown on part of the "screen" (field of view) and, can be supplemented by showing a computer-generated image (still or motion video) which can presented into the field of view as a separate image or superimposed and scaled over the image of the real tissue. Additionally, other instructional material can be presented into the surgeon's field of view which can contain useful information about the operation, the tools used, other metrics of performance or information about specific products, chemicals, pharmaceuticals or procedures that may be placed in the field of view of the surgeon to derive advertising benefit, as the law allows.

The composite image that is seen in the field of view of the surgeon may be displayed onto the video monitors in the operating theater, or, the monitors may display information that supplements the training experience, such as instructional video material regarding safety issues or a checklist of items that must be present and accounted for prior to the surgery training experience beginning. For educational and study purposes, all audio and video generated from each source may be time synchronized and recorded.

As a result of students tests, reports may be issued relating to the experience a particular student had during the test, how well they did, in comparison to the correct procedures with the individuals performance, and an indication of the performance of all individuals taking these tests for a particular question. In this manner, an exam can be determined and customized for a particular company, for example. In another embodiment, the Medical Examination Board can identify different test questions by case, one time individual performance, cumulative performance by an individual, etc., and can provide different levels of difficulty. The virtual surgery system of the present invention or other test taking device not related to surgery or medical applications can include training, test taking and records archiving abilities (for example, in a medical context this archiving can relate to a patient's medical records).

In an embodiment, it is possible to use live patients and telerobotic surgery. As latency issues are solved, this becomes possible.

All references referred to herein are hereby incorporated by reference for all purposes.

Figure 9:
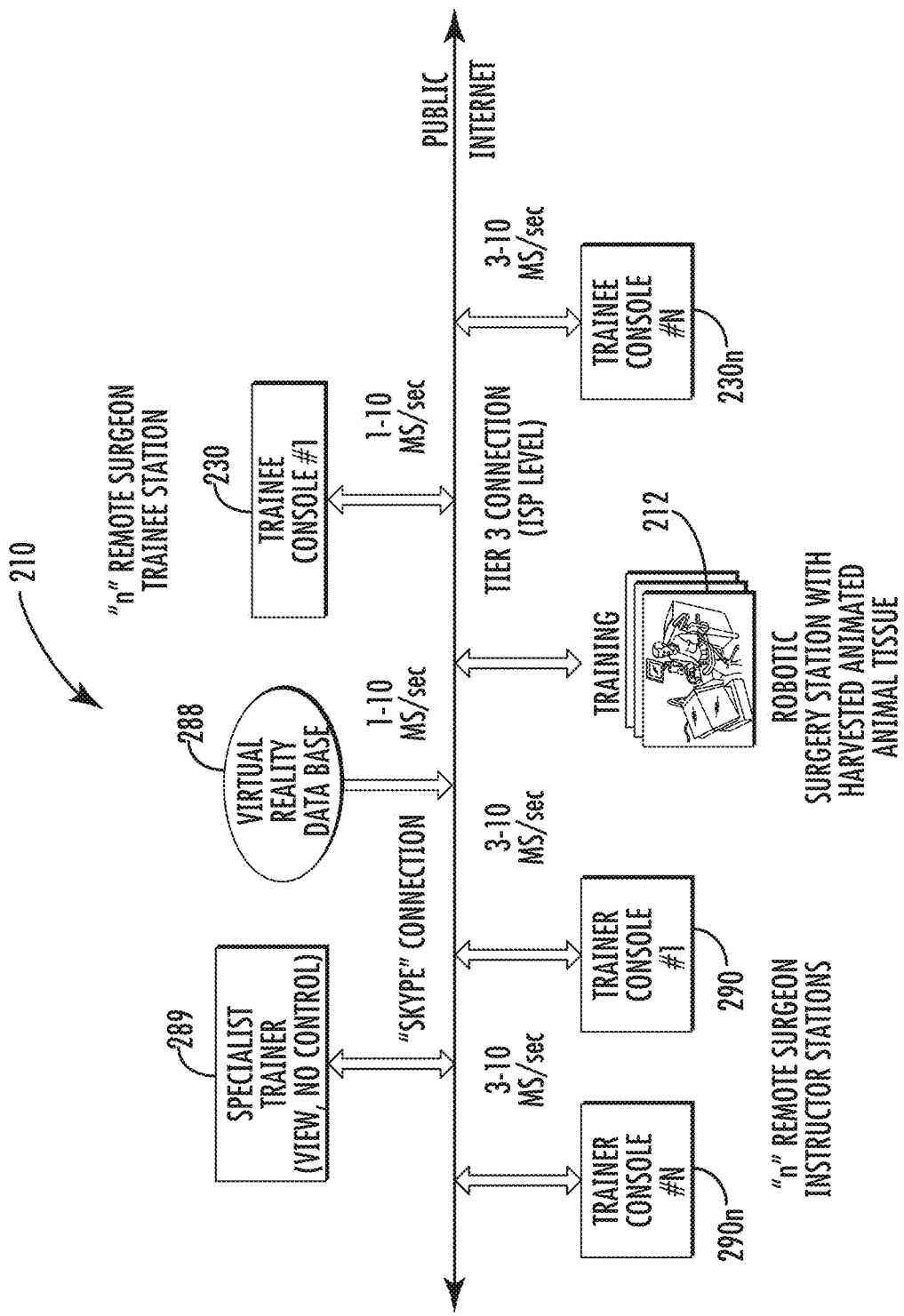
FIG. 9 shows an example of the flow of data to and from a remote surgery station, remote surgeon trainee station, and remote surgeon instructor station in accordance with a non-limiting example.
Figure 10:
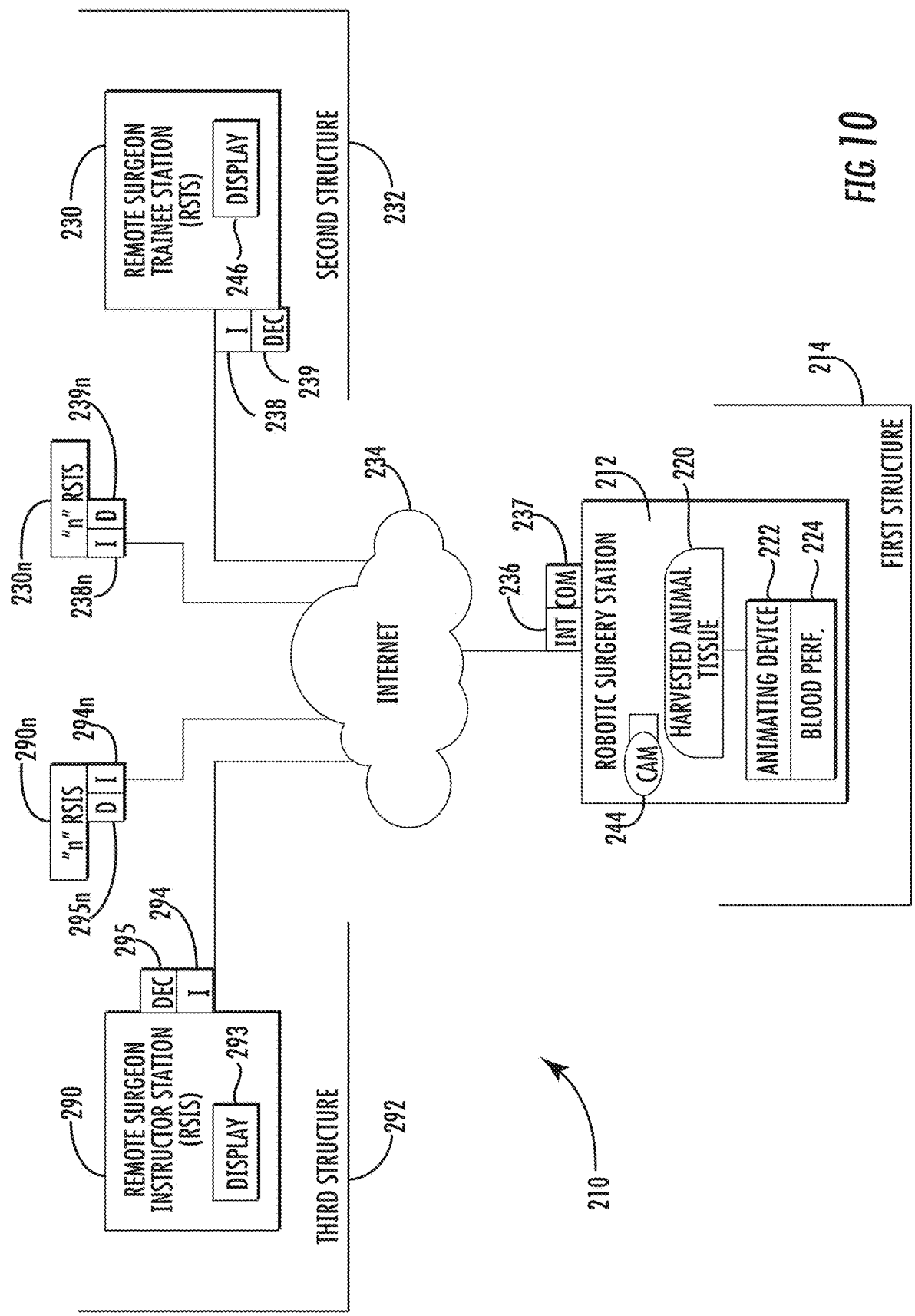
FIG. 10 is a fragmentary, block diagram of the telerobotic surgery system for a remote surgeon training and showing the robotic surgery station, remote surgeon trainee station, and remote surgeon instructor station in accordance with a non-limiting example.

FIG. 9 shows the flow of data in another embodiment of the telerobotic surgery system 210 and showing the flow of data from a robotic surgery station 212 to a remote surgeon trainee station 230 and remote surgeon instructor station 290. For purposes of description, many of the same elements described relative to FIG. 1 are shown in FIGS. 9 and 10 with reference to numerals in the 200 series. The system 210 includes a virtual reality database 288 that may bring up various image overlays or other images onto a display that pertain to surgeon training. A specialist trainer 289 may view a trainee operation without having control over the remote surgery training. Thus, a "skype" connection may be used between the specialist trainer 289 and the robotic surgery station 212 and internet since latency is not as critical. Different latency in milliseconds between different components are shown as non-limiting examples.

FIG. 10 is a block diagram showing the robotic surgery station 212 having the harvested animal tissue 220 and animating device 222 contained at a first structure 214 at a first location. This robotic surgery station 212 connects via a communications network 234 such as the internet to the remote surgeon trainee station 230 at a second structure 232 at a second location, and a remote surgeon instructor station 290 at a third structure 292 at a third location, for example.

As illustrated, the communications network 234 as the internet couples the robotic surgery station 212 to the remote surgeon instructor station 290 and remote surgeon trainee station 230 so that a trainee surgeon at the remote surgeon trainee station is able to remotely train by performing surgery on the harvested animated animal tissue at the robotic surgery station. An instructor surgeon at the remote surgeon instructor station 290 is able to remotely instruct the trainee surgeon by also performing surgery on the harvested animated animal tissue at the robotic surgery station 212.

As illustrated, one other remote surgeon trainee station 230n may be coupled to the communications network 234 and at least one other remote surgeon instructor station 290n may be coupled to the communications network. The remote surgeon instructor station 290 is at the third structure 292 at the third geographic point remote from the first and second geographic points represented by the first structure 214 and second structure 232 in this example.

The communications network has a latency of not greater than 200 milliseconds in one example, and in another example, has a latency of not greater than 140 milliseconds. The communications network also includes a first communications interface 236 coupled to the robotic surgery station 212 and a second communications interface 238 coupled to the remote surgeon trainee station 230. The first and second communications interface are configured to be coupled together via the internet 234. The robotic surgery station 212 as in the example shown in FIG. 1 includes at least one camera 244 and the remote surgeon station as in the example of FIG. 1 comprises at least one display 246 coupled to the at least one camera via the communications network. As in the example described relative to FIG. 1, the at least one camera 244 may be formed as a stereo image camera and the at least one display 246 may include a binocular display. A similar display 293 may also be used at the remote surgeon instructor station 290. As in the example relative to FIG. 1, the first communications interface 236 may be configured to determine if the latency is above a threshold, and when above a threshold, perform at least one of image size reduction and reducing peripheral image resolution as described relative to FIG. 2. The first communications interface 236 may include a data compression device 237 and the second communications interface 238 may include a data decompression device 239. The at least one animating device 222 includes a movement animating device to simulate at least one of breathing and heartbeat such as simulating normal and abnormal breathing and normal and abnormal heartbeat. The at least one animating device 222 also includes a blood perfusion device 224. As described before, the harvested animated animal tissue 220 may be formed from porcine tissue.

As also illustrated, a third communications interface 294 is coupled to the remote surgeon instructor station 290 and the first, second and third communications interfaces 236, 238, 294 are configured to be coupled via the internet 234 so that a trainee surgeon at the remote surgeon station is able to remotely train by performing surgery on the harvested animated animal tissue 220 at the robotic surgery station 212, and while an instructor surgeon is able to remotely instruct the trainee surgeon by also performing surgery on the harvested animated animal tissue at the robotic surgery station. A number of remote surgeon trainee stations 230n may be used with each including a communications interface 238n that may include a data decompression device 239*n*. Likewise, a number of remote surgeon instructor stations 290*n* may interconnect to other stations and the robotic surgery station 212 via the interface 294*n* and decompression device 295*n*. The first, second and third communications interfaces 236, 238, 294 when coupled via the internet define the latency of not greater than 200 milliseconds, in one example, and not greater than 140 milliseconds in another example.

As further shown in FIG. 9, the round-trip latency is less than 140 milliseconds in an example and has a full three-dimensional high definition at 60 frames per second in any displays with full operative control for both the remote surgeon trainee station and remote surgeon instructor station. Frame-by-frame compression may be controlled by proprietary feedback loops. A trainee surgeon at the remote surgeon trainee station 230 is able to train remotely by performing surgery on the harvested animated animal tissue 220 at the robotic surgery station 212. Besides having a conversation as part of the training, it is possible for the remote instructor at a remote surgeon instructor station 290 to take control of the operation and perform part of the surgery. For example, the remote surgeon instructor station could include a switch or other means allowing the instructor surgeon or another surgeon located at the remote surgeon instructor station to take over the operation from the trainee located at the remote surgeon trainee station 230.

As illustrated in FIG. 9, more than one remote surgeon trainee station 230*n* can be used in the system and more than one remote surgeon instructor station 290*n* can be used. Although one specialist trainer station 289 is shown in FIG. 9, it is possible to use multiple specialist trainer stations that have no control and only view the surgical training procedures, thus, allowing a skype connection since data latency is not as critical. The remote surgeon trainee station 230 could be located where live surgery takes place such as a real operating room having the robotic surgical equipment and the trainee learns on such equipment.

As noted before, it is possible to use image recognition software, and more particularly, a modified form of facial recognition software to identify anatomical structures and organs in the mannequin and animal tissue that forms the body and then warp other images to fit the field of view of the surgery and overlay/combine the two sets. Preferably, it is three-dimensional imaging, which is sent to a display device that the surgeon uses during robotic surgery. An example of such imaging is included in commonly assigned U.S. patent application Ser. No. 15/138,403 filed on Apr. 26, 2016, and U.S. patent application Ser. No. 15/150,635 filed on May 10, 2016, the disclosures which are hereby incorporated by reference in their entirety.

The surgical simulation device may generate a large amount of data that may initiate machine learning systems with the surgical simulation device and be a source of continuing data on the learning curve of surgeons and students as they train on robotic-assisted surgery devices or other surgical robots. The surgical simulation device as described may be a source of continuing data on the learning curve of surgeons as they train to become more experienced at robotic-assisted surgery devices or migrate from different platforms such as the daVinci robotic platform into a new type of robotic-assisted surgery device. Data is generated as a machine learning data generation feature set ("feature set") to allow digitally-enabled surgery, also termed Surgery 4.0. The video data may be used by companies engaged in surgeon training or robot manufacture.

Figure 11:
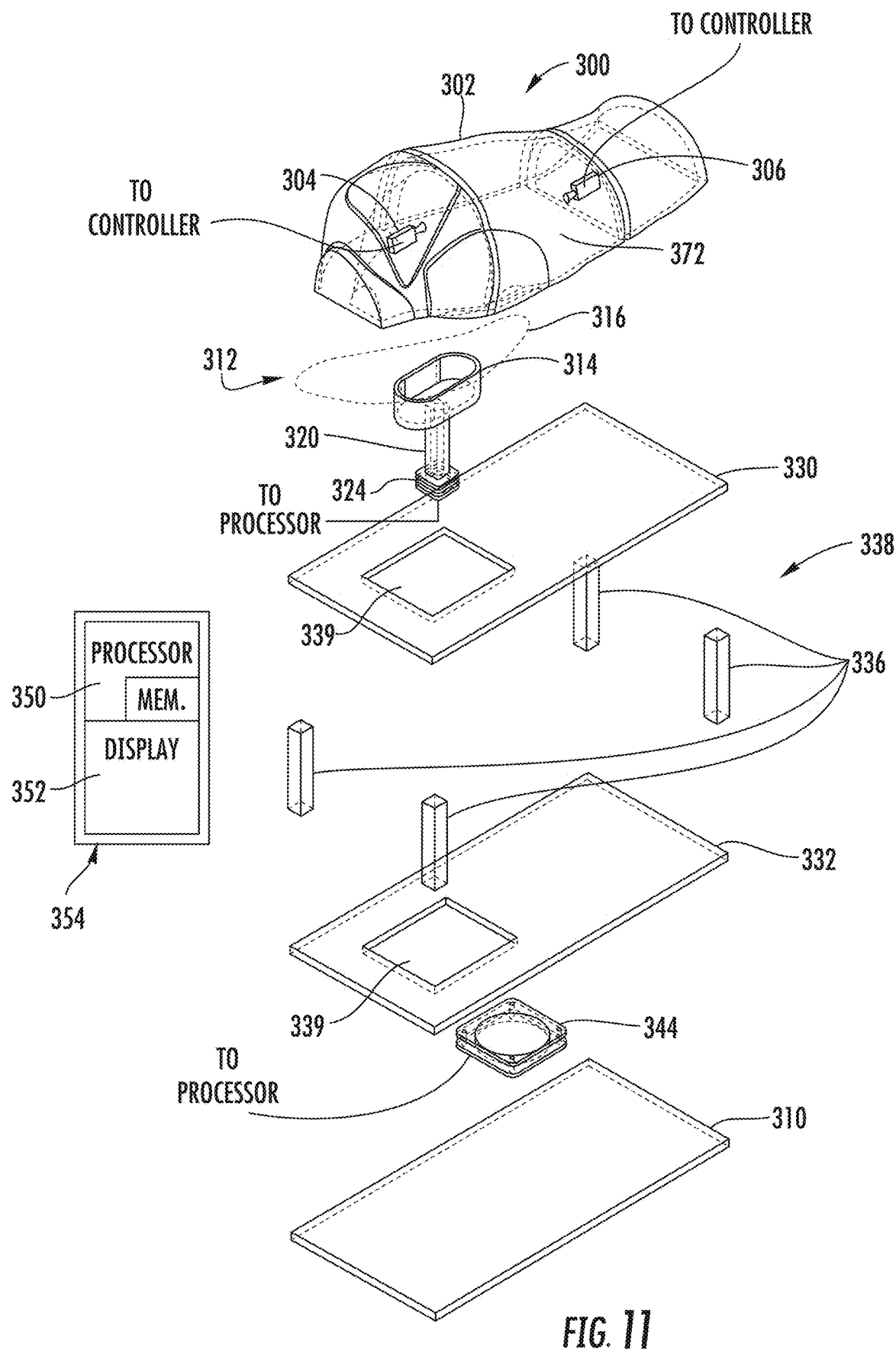
FIG. 11 is an exploded isometric view of the surgical simulation device in accordance with a non-limiting example.
Figure 12:
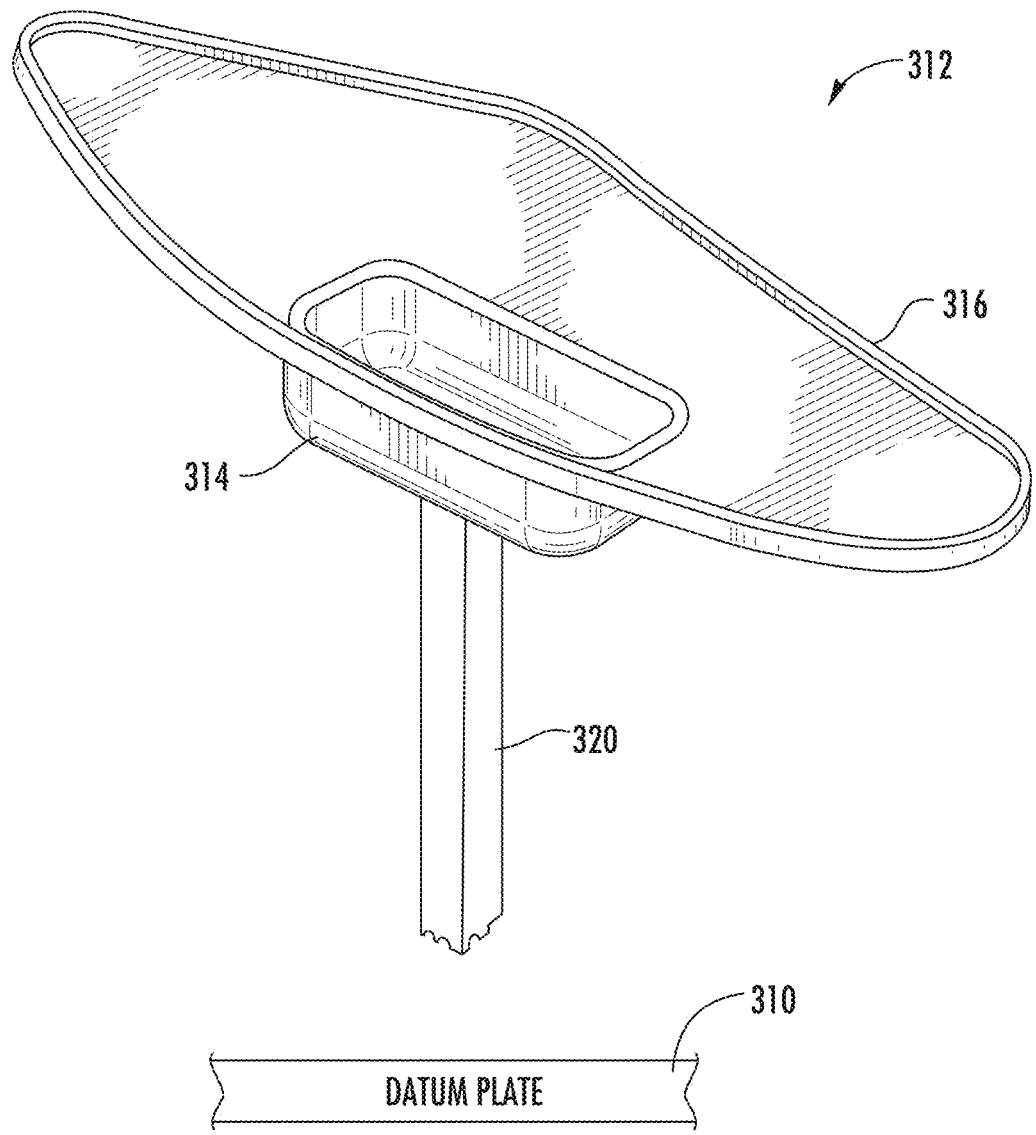
FIG. 12 is a fragmentary, partial perspective view of the tissue tray used in the surgical simulation device.
Figure 13:
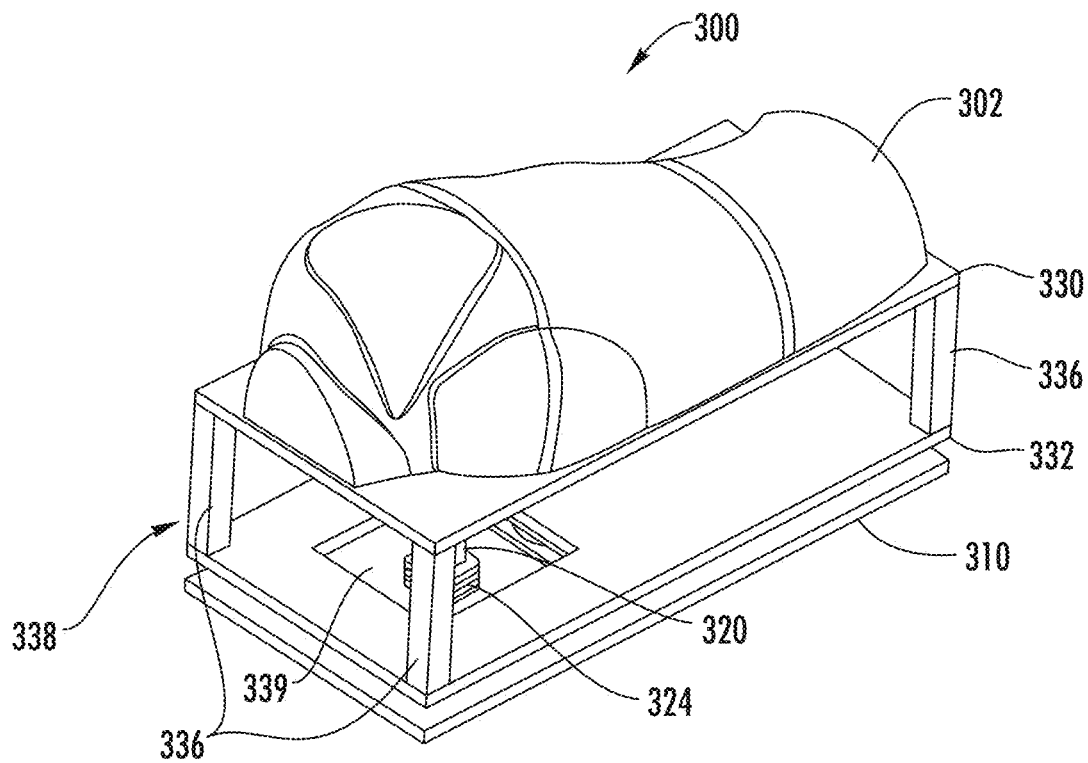
FIG. 13 is an isometric view of the surgical simulation device in accordance with a non-limiting example.
Figure 14:
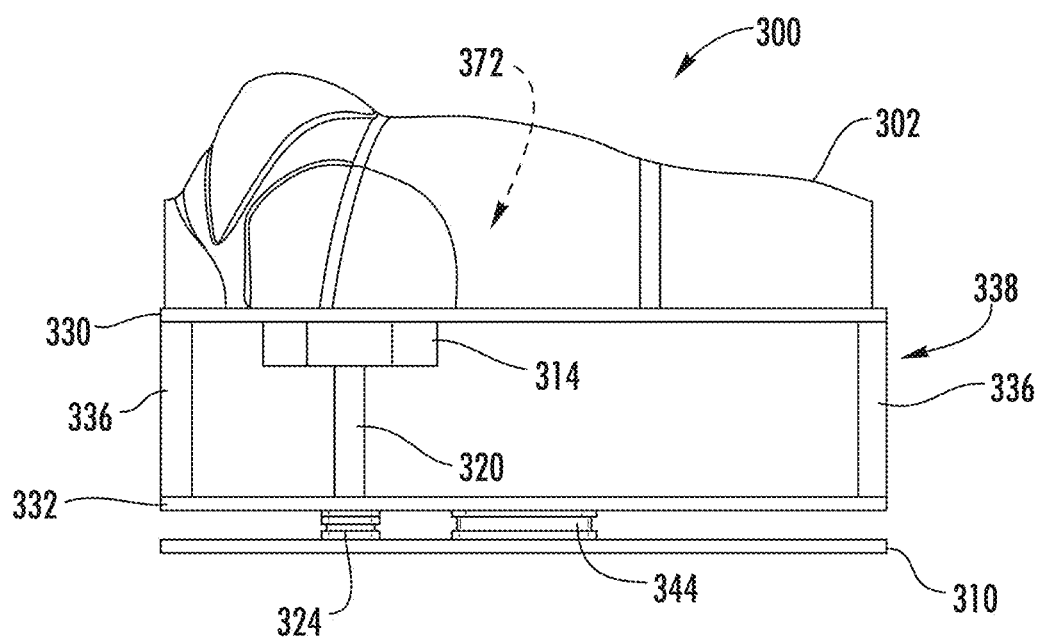
FIG. 14 is a side elevation view of the surgical simulation device in accordance with a non-limiting example.
Figure 15:
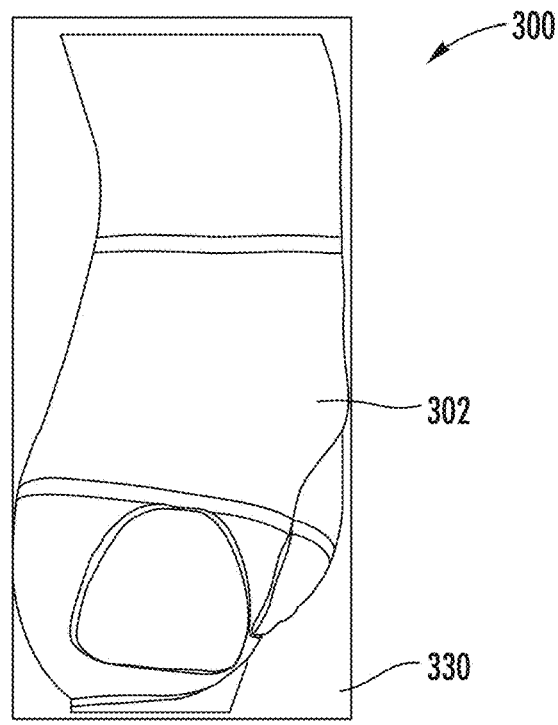
FIG. 15 is a top plan view of the surgical simulation device in accordance with a non-limiting example.

Referring now to FIGS. 11-20, a surgical simulation device 300 is shown and in the example of the exploded isometric view of FIG. 11 and FIGS. 13-16, shows a silicon mannequin 302 corresponding to both the thorax and abdomen to form a simulated body for surgical training. A first 3-D video camera 304 is positioned in a front hollow space corresponding to the area under the shoulder, and a second video camera 306 is positioned in the rear hollow space corresponding to the area under the hips. A datum plate 310 as a datum reference is formed as a planar support plate and is a base support that may be positioned on an operating table or bed (not illustrated). In an example, the datum plate 310 is a MIC-6 aluminum one-half inch plate. A tissue tray 312, such as shown in greater detail in FIG. 12, is formed as a surgical bottom indentation tray 314 and includes a raised and peripheral larger section as a tray perimeter 316, which together support the animal tissue, such as porcine tissue that may be animated as described above by the techniques explained. The tissue tray 312 may be machined from an aluminum billet and may be formed similar to the tissue tray or surgical tray as it is often termed and disclosed in commonly assigned U.S. Design Pat. No. D773,686, the disclosure which is hereby incorporated by reference in its entirety.

The tissue tray 312 is supported on a pedestal 320, such as formed from an aluminum or similar material, and is adjustable in height in an example. A first sensor 324 as a force and torque sensor is supported at the end of the pedestal 320 and engages the support or datum plate 310 as illustrated best in FIG. 14. An example first sensor 324 as a force and torque sensor may be an ATI Net 40 IP65 4/torque multi-sensor with two calibrations that are selectable by software control. The first sensor 324 is supported on the datum plate 310 such as the example MIC-6 aluminum one-half inch plate that forms the datum reference. A top plate 330 and bottom plate 332 are spaced from each other and supported by corner posts 336 as illustrated and each may be a solid one-quarter inch MIC-6 aluminum plate for rigidity and forms a mannequin support structure 338. The top plate 330 supports the silicon mannequin 302. Both top and bottom plates 330, 332 may also be formed from aluminum MIC-6 plates, such as a one-half inch aluminum plate as with the datum plate 310. Each of the top and bottom plates 330, 332 include cut-outs 339 that permit the pedestal 320 to extend upward through the top and bottom plates 330, 332 as supported by the datum plate 310. The top and bottom plates 330, 332 may each include an aluminum side sheet or other side structure 340 that encloses the plates to form a box structure (FIG. 20) and completes the mannequin support structure 338. The bottom plate 332 is supported on the datum plate 310 by a second sensor 344 as a torque sensor, and in an example as an ATI Net Delta IP65 4/torque multi-sensor with two calibrations and selectable by software control. The first and second video cameras 304, 306, first sensor 324 and second sensor 344 connect to a suitable processor 350 operating as an image processor, which in turn, is connected to a display 352. The processor 350 and display 352 in a non-limiting example could be a portable or laptop computer 354. In an example, it is possible that the first sensor 324 connects to a first computer and the second sensor 344 connects to a second computer, which in these non-limiting examples are laptop or notebook computers. In the example shown in FIG. 11, the first sensor 324 is mounted on the datum plate 310 and the pedestal 320 interconnects the first sensor 324 and tissue tray 312. It is possible for the pedestal 320 to be mounted on the datum plate 310 and the first sensor 324 connected to the bottom of the tissue tray.

Figure 16:
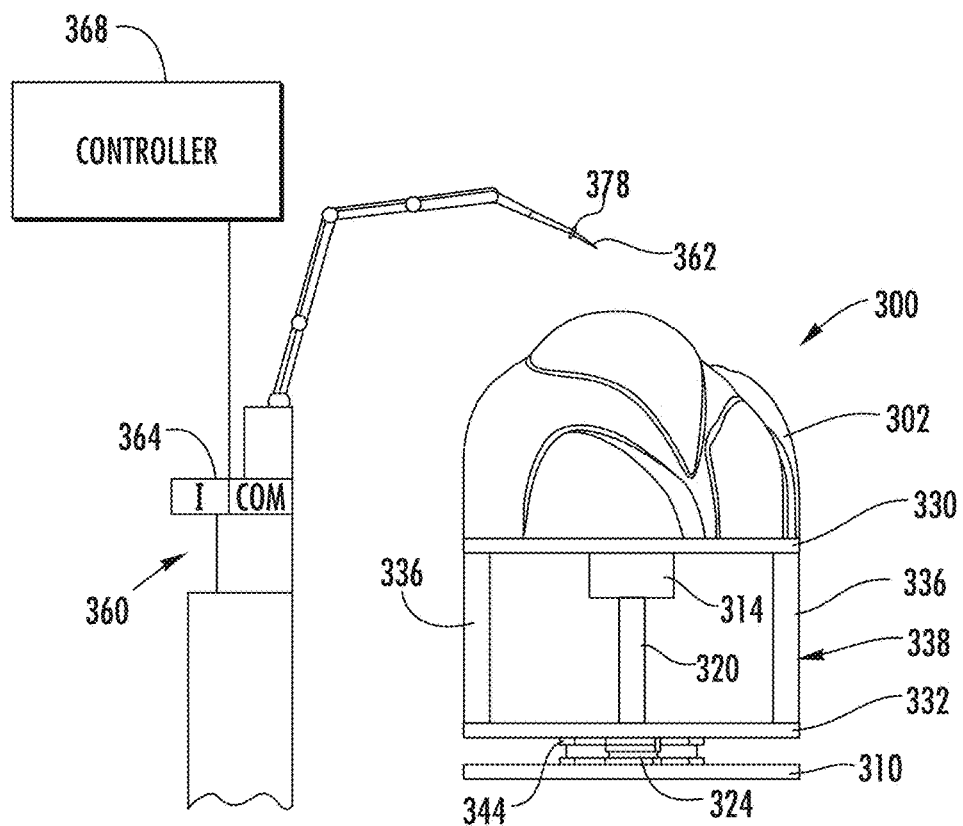
FIG. 16 is a front elevation view of the surgical simulation device and a robotic surgery station positioned adjacent the surgical simulation device.

The processor 350 in this example could be part of a larger networked or stand-alone computer system, or be a single computer, or first and second computers such as portable computers and receive video feed from the first video camera 304 and second video camera 306 and any other cameras or three-dimensional endoscopes and store it in a suitable memory 351. The processor 350 will receive real-time control codes and safety codes coming from a surgeon's control console at a robotic surgery station 360 such as shown in FIG. 16 In the example shown in FIG. 16, the robotic surgery station 360 is positioned adjacent the surgical simulation device 300.

As explained above, the robotic surgery station 360 includes the surgical tool 362 and may include other components such as a communications interface 364 that may connect to remote locations and connect to a controller 368 that operates the local surgical robot as the robotic surgery station. The first and second video cameras 304, 306 take video images, and preferably the three-dimensional video that is used in conjunction with motion analysis software. There may be other video feed in some cases such as produced from a high definition, three-dimensional endoscope that in one example may contain an optical fiber that carries white light with reduced infrared output as "cold light" and may be used with the "firefly" intravenous dye that surgeons often use to identify areas of angiogenesis. The mannequin 302 is separated from any operating table by the mannequin support structure 338 formed by the top and bottom plates 330, 332 and datum plate 310.

Ground truth may be established by placing markers at key location points inside the mannequin 302, such a specific sites along the ribs formed in the mannequin or along the vertebrae. These markers could be passive markers such as a reflective material or active switchable light sources, such as light emitting diodes (LED's) or the tips of lighted fiber optics. Markers can be placed on the animal tissue used in the simulator during the preparation process. The markers can be active or passive and can be positioned to keep anatomical points of interest or a fixed distance from an anatomical point of interest or in a fixed dimensional "constellation" of the tissue. The markers can be inside and/or outside the tissue and can be discovered such as revealed by operative dissection. The markers can be non-single points such as a string of markers placed inside a vessel and can produce infrared (IR), ultraviolet (UV), or visible light and can be switched on and off by external control. The markers could contain information such as a bar or a QR code can be used to serialize and track the tissue or the simulator.

Figure 17:
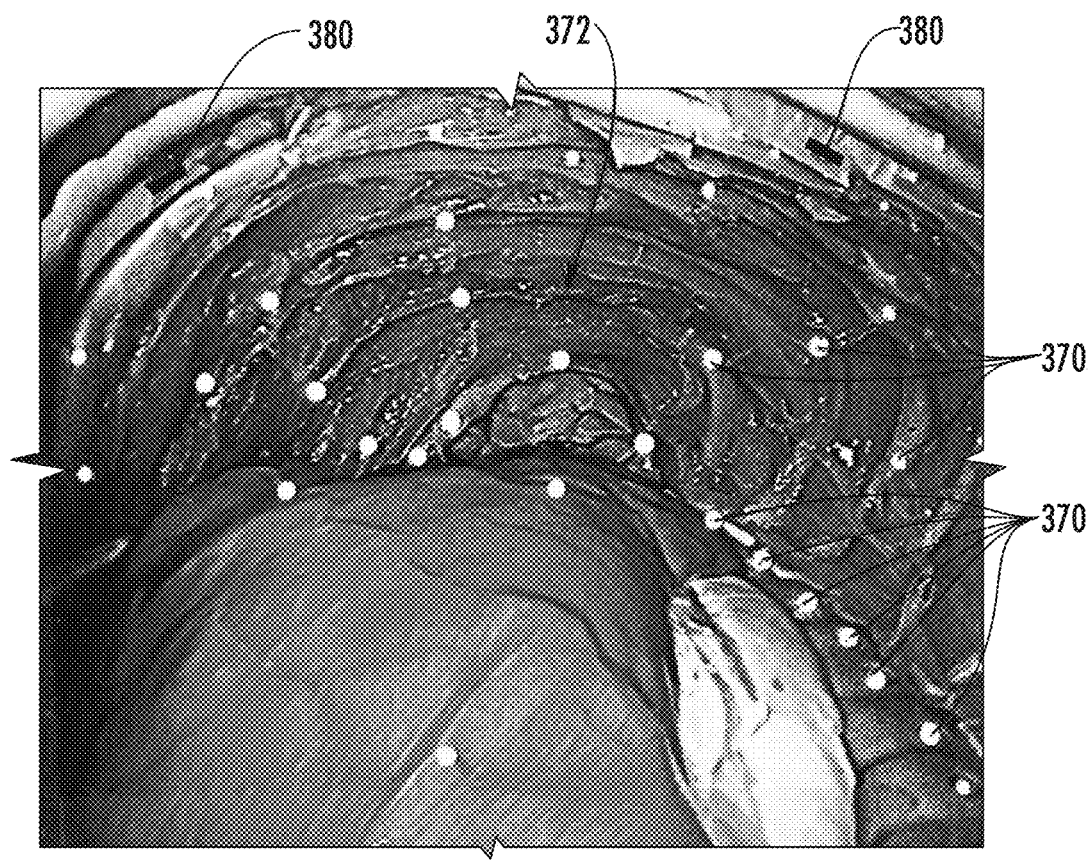
FIG. 17 is an image showing the inside of the mannequin and a portion of the tissue and the location of light emitting diodes in accordance with a non-limiting example.
Figure 18:
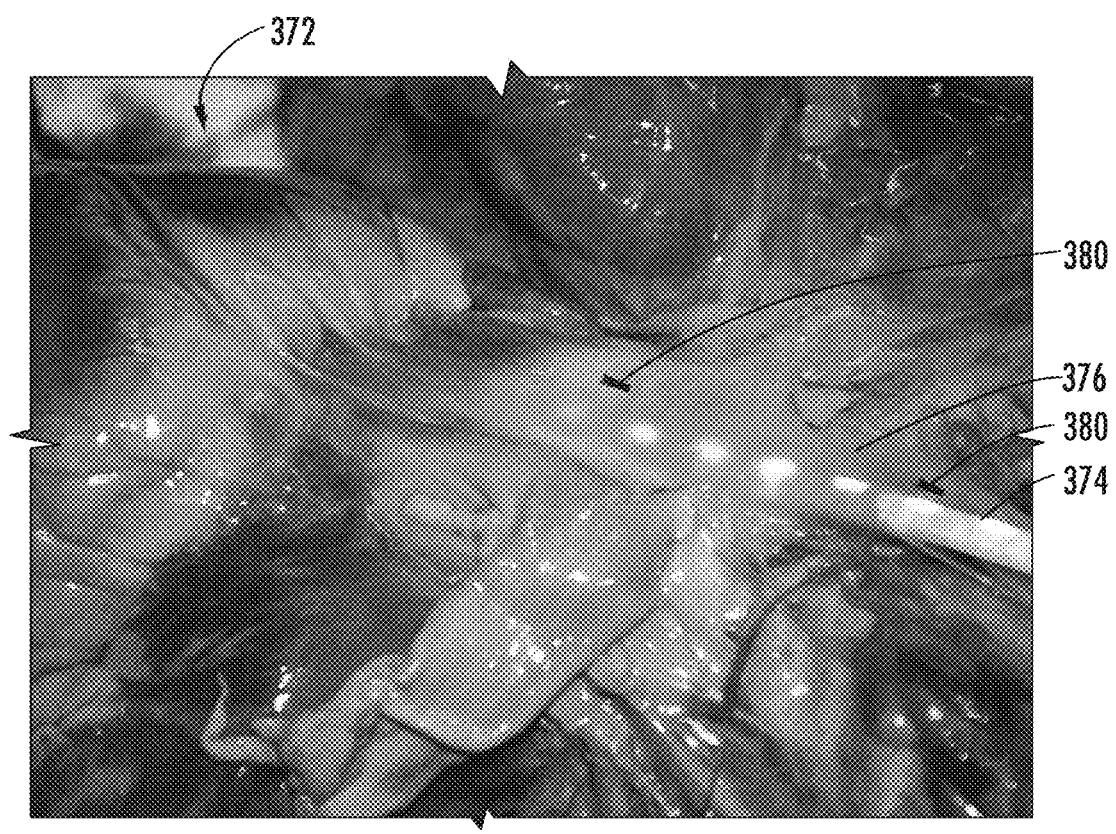
FIG. 18 is an image showing an optical fiber extending through a blood vessel of tissue contained within the tissue tray in accordance with a non-limiting example.
Figure 19:
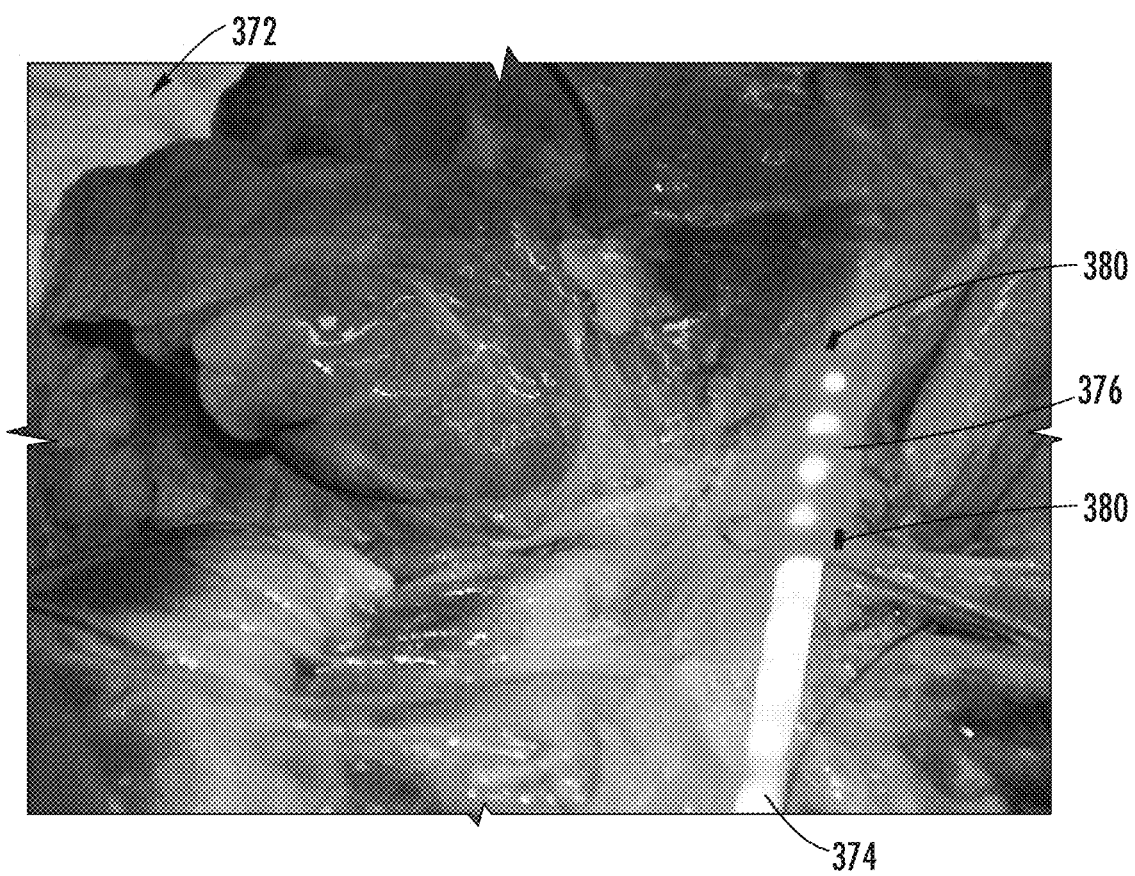
FIG. 19 is another image similar to FIG. 18 of an optical fiber extending through a blood vessel.

Referring now to FIG. 17, an example is illustrated of the light emitting diodes 370 positioned in the thorax formed by the interior of the mannequin 302 and showing the animal tissue. The light emitting diodes 370 are shown by the white spheres or dots and operate in this example as markers for training purposes so that one training remotely or at the location of the mannequin may see the more readily the points of interest defined by the market such as arteries or organs. A body cavity 372 is formed by the interior of the silicon mannequin 302 and FIG. 17. It is possible to use a string of LED's 374 such as shown in FIGS. 18 and 19, where the string of LED's is positioned inside a blood vessel 376. The string of LED's 374 may be turned on and off as desired in a training or demonstration process, and in an example, run on 8 to 10 volts DC. It is also possible to place labels on the ribs with the correct rib number so that the surgeon training on the system can see which rib number is identified when the surgical tool is near. Some instructions in a training situation may begin similar to "starting between the fifth and sixth ribs: . . . " The labels may be considered by some doctors to be demeaning and distracting and the text or numbers can be placed in as markers, which can be backlit by switchable light sources or "rib color" when not backlit. In this manner, the markers are not seen during normal surgery, but the trainer can illuminate them at will and then turn them off. It is possible to drill tiny holes at key points and insert fiber guides within the mannequin 302.

It should also be understood that not only may any animal tissue that is contained within the tissue tray 312 and portions of the body cavity 372 of the silicon mannequin 302 include markers as described, but also parts of the tissue tray may include markers for guidance. A tool marker 378 may also be placed on the surgical tool 362 such as at the tool effector end (FIG. 16). In that example, this tool marker 378 on the surgical tool may be a fluorescent ink or other passive reflector.

With or without markers, it is possible to use commercial or open sourced facial recognition software packages to identify key parameters of the mannequin 302 and the animated animal tissue and label these parameters with a naming convention or with other functional information such as the flow direction of simulated blood within a vessel. Markers may be included inside the body cavity 372 of the mannequin 302 and along various formed areas within the mannequin to assist in surgical tool alignment and facilitate the use of facial recognition software for organ recognition based on the known images of organs. It is possible to retrieve the generated video or other images from the first and second video cameras 304, 306 and use the ground truth established by the markers as obtained from the silicon mannequin 302 and tissue to "warp" and "stretch" an external image to scale, align it and fit it to the tissue presented on a display 352 so that the surgeon training on the system has a better idea of what the surgeon trainee is looking at on the display 352, for example, the display associated with the robotic surgery station 360 or any other computer display. These external images can contain text, color or other information that can be displayed in three-dimensional alignment with the tissue. It may be possible to use spatial light modulation of various images and process it with Fast Fourier Transforms (FFT) of known images to the tissue presented such described in U.S. Pat. Nos. 6,538, 791 and 6,693,712, the disclosures which are hereby incorporated by reference in their entirety.

In these systems, a high rate optical correlator performs real-time optical comparisons and compares a sample image to a wide variety of reference images by using a multiple quantum well spatial light modulator that rapidly presents a large number of reference images for correlation. The multiple quantum well spatial light modulator may be a spatial light modulator as a Van Der Lugt image correlator in combination with a spectrometer that permits optical comparisons at 300,000 frames per second versus 10,000 frames per second. It is possible to have a substrate surface as a reference point and alignment of the optical pieces may be achieved within a wavelength to eliminate the possibility of a "no correlation" result due to optical misalignment of the optical pieces.

It is also possible to use laser based scanning equipment along with multiple sensor (camera) locations to create a three-dimensional model of the body cavity 372 in the mannequin 302, the animated animal tissue and any tools. Virtual camera locations can look at various locations and models can be created on a frame-by-frame basis and post-processed or processed in real-time. Wire frames may be formed from the data.

It is also possible to affix strain gauges 380 to the tissue such as shown in the example shown in FIGS. 18 and 19. It may be possible to use single glass or plastic optical fiber with fiber optic strain gauges. Further information for force and compression may be desired. The measurements of impedance such as the resistance, inductance and capacitance can be captured between any grounding pads and specified areas of tissue to ensure that conductivity may be identical to live human tissue when using energy devices such as cautery. Actual versus intended placement of various robotic tools and wristing mechanisms can be marked and identified. It is possible to calculate actual versus intended placement that may be desirable when working with high BMI mannequins having thick abdominal walls causing distortion of tool position. Stereotactic analysis of tool position is possible.

It is possible that the data in the feature set as collected from the markers and/or other known imagery may be incorporated with other simulator data and used by robot manufacturers and applied in machine learning systems. The data gives ground truth and can be based on the markers and other data acquisition. It is possible to collect the data on the surgical simulation device 300 and to have a better training system and understand better where the surgical tool can go inside the mannequin 302 and around the tissue in the tissue tray 312 and how best to manipulate the surgical tool 362 so as to not puncture blood vessels and other organs, thus imparting a more realistic and effective training scenario. The system may provide a topographical map of the body cavity 372 inside of the silicon mannequin 302 corresponding to the thoracic cavity or an anatomical cavity including a lower or upper abdomen area. The image recognition software, such as facial recognition software, may identify organs or parts of organs and establish ground truth and be configured to locate certain organs. Valid data points or repeatable data points known in a three-dimensional space can be located in both temporal and synchronized data.

As noted before, it is possible to place an LED 370 (FIG. 17) or tip of an optical fiber at each vertebrae and at other certain points where it connects to a rib. These may be blinked during a training session to identify certain rib numbers. They may be turned on and off to assist in training. They provide the ground truth for a fixed spot in the mannequin 302 on the tissue. As an example, if a trainee surgeon is operating and performing an upper left lobectomy and removes a lobe of a lung, there may be three connections or areas that are important to locate and identify and avoid damage, e.g., the pulmonary vein, the pulmonary artery, and the bronchus. These components become critical points. The image recognition software may assist in recognizing and distinguishing among the pulmonary vein, the pulmonary artery, and the bronchus. Markers may be placed on each of these components, such as an optical fiber string or LED's 370 of different colors, and may be blinked at different rates during training to assist the training surgeon. It is possible that the tissue tray 312 as a cassette as described above may be prepared before it is placed in the mannequin with the various markers.

It is possible from the data received from the various markers and video cameras to form a wireframe or three-dimensional computer model to assist in surgical training. The first and second sensors 324, 344 provide better control over how the student or surgeon trainee may be operating the robotic tool during the surgical training and register how much force is pulled or pushed on the tissue, and how much force is pulled or pushed on the body itself, formed by the mannequin, which may include various anatomical components such as the ribs, muscles and vessels and forming the body cavity. The processor 350 and display 352, such as the portable computer, may give an indication of how the forces are distributed on the tissue and on the body, i.e., the mannequin 302 in this example. Data may also be used to create a consistent experience for different trainees and their performance is compared. This could aid and implement machine learning database.

Markers can be placed in the mannequin 302, in the tissue tray 312, in any tissue contained in the tissue tray and on the robotic surgical tool 362. The markers help create the three-dimensional wireframe from the constellation of those various markers. The video data from the first video camera 304 and the second video camera 306 may be used to form the constellation and wireframe for display, which the surgeon trainee can view on the appropriate display 352. The robotic surgery tool 362 may work in association with an endoscope, which could be a three-dimensional endoscopic camera. An example of possible markers includes the Firefly™ system used by Intuitive Surgical Corporation as a fluorescence imaging pack (indocyanine green fluorescence). This type of system can be imaged by different light, including ultraviolet light. LED's 370 could be used or an optical fiber run through various holes in the mannequin 302 as noted above. The light sources may operate at different frequencies or wavelengths as chosen by the training personnel. The use of markers is advantageous because the trainee may know the exact place on each of the ribs where the rib joins the vertebrae or becomes cartilage by placing markers at those points, in this instance corresponding to the inside or body cavity 372 of the mannequin 302.

The surgical simulator device 300 as described is advantageous since better control over training is established and errors reduced such as brushing a thin or high pressure artery wall may be avoided by training with the various markers and use of the three-dimensional imaging. Another advantage of the surgical simulation device 300 as described and shown in FIGS. 11-19 is the tissue tray 312 and any animal tissue as a tissue set is isolated from the interior body wall, i.e., the body cavity 372 of the silicon mannequin, but the forces and torque generated by the surgical tool 362 against the mannequin as body, such as formed ribs and on the animal tissue as a heart or lung block may be separated and the forces shown on the respective display 352, as an example, are one or more laptops connected to the respective first and second sensors.

In conjunction with the motion analysis software, it is possible to create a three-dimensional wireframe image on the display 352. It may also be possible to adhere the animated animal tissue such as a heart/lung body unit into the tissue tray 312. The first and second pressure sensors 324, 344 operate to determine torque in the X, Y, and Z direction and force in the X, Y, and Z direction. A laptop, portable computer or processing device may be connected to both or each of the first and second pressure sensors 324, 344 and display the appropriate graphs of the force and torque on a real-time basis. Thus, in a non-limiting example, a portable computer 354 connected to the first sensor 324 will determine the isolated tissue force that is exerted on the animated animal tissue such as the heart and lung, while the same or second portable computer could be connected to the second sensor 344 and show the forces extending down to the operating table through the body of the silicon mannequin 302. Two portable computers 354 could be used, one connected to the first sensor 324 and a second connected to the second sensor 344. The datum plate 310 is the reference for both first and second sensors 324, 344. This system would give the flexion data on the body corresponding to the silicon mannequin and on the heart and lung tissue block contained within the tissue tray 312. This system works in conjunction with the cameras 304, 306 and markers such as LED's 370 so that a three-dimensional wireframe may be established.

It is also possible for the software to filter out the movement provided by the simulated heart beat and lung breathing. The beats per minute and breaths per minute can be established at exact quantities since they are artificially induced. The first and second sensors 324, 344 as force and torque sensors are usually wired, and not wireless, since often high RF energy is produced by a cauterizing tool and the high RF energy would interfere with wireless links and any synchronization of data.

Although the thoracic model was illustrated, it is possible to use an anatomical or abdominal model where the spleen, stomach, liver, gallbladder and pancreas form one unit or a colorectal tissue unit. It is possible to train robotically on upper or lower abdomens or a prostate model. Also, the heartbeat and breath movement can be filtered since in an example, the sustained heart rate and breath rate could be 78 beats per minute for the heart and 12 breaths per minute for the lung. That movement could be filtered since they are known movements and the data generated for the amount of forces generated by the surgeon trainee on the robot surgical tool 362. The data set may include the three components of the optical data, force and torque sensing of the tool on the tissue from the first sensor and the force and torque sensing from the tool against the mannequin acting as the body and onto the datum plate.

The first force torque sensor 324 and second force torque sensor both may be force torque sensors manufactured by TI Industrial Automation of Apex, N.C. The first force torque sensor 324 may be a mini 40 IP65/IP68 that has a low profile design with high capacity and operates as a multi-axis force/torque sensor system that measures six components of force and torque and includes basic components of a transducer, processor interface electronics and cabling, including the microprocessor. Each sensor may have an internet protocol (IP) address. A monolithic transducer uses silicon strain gauges to sense forces and provide high noise immunity and allow high overall protection. It has built-in capabilities of tool transformations to translate and/or rotate the force/torque reference frame with software that is configured with basic data logging capabilities. It includes a monolithic sensing structure with high-strength alloy that provides IP60, IP65, and IP68 environmental protection with low-noise interface electronics that interfaces for Ethernet, PCI, USE, Ethernet/IP, ProfiNet, can and other communications protocols. It includes beams and flexures that create stiffness and provide high overhead load protection. The second force torque sensor is a high strength system that has much greater sensing ranges sold under trade designation Delta IP65.

An example three-dimensional video camera for each of the first and second video cameras 304, 306 may be a three-dimensional camera sold by Sony Corporation under the designation HDR-TD 30V as a full HD 3D handicam camcorder with a 3.5 inch LCD. This camera includes two full HD sensors to capture 1920×1080 3D video with the lens and processor plus 24P/60P W/20.4 MP Exmor R CMOS sensors in a dual wide-angle G lenses. It may include 29.8 mm/2D and 33.4 mm focal length and video mode.

It is possible to use motion analysis software such as produced by Motion Analysis Corporation of Santa Rosa, Calif. It is also possible to place labels on the ribs with their correct number, which can aid in surgeon training since many instructions may begin with statements similar to "starting between the fifth and sixth rib: . . . " Text or numbers may be inserted as markers and they may be back lit by switchable light sources and "rib color" would not be back lit. In this manner, they would not be seen during normal surgery, but the trainer may eliminate them at will and then turn them off. It is possible to drill tiny holes at key points in the mannequin 302 and insert fiber guides such as the strand LED fiber optic cable, for example, typically found for use in some automotive or other applications and usually about 0.5 MM in diameter in one example.

Figure 20:
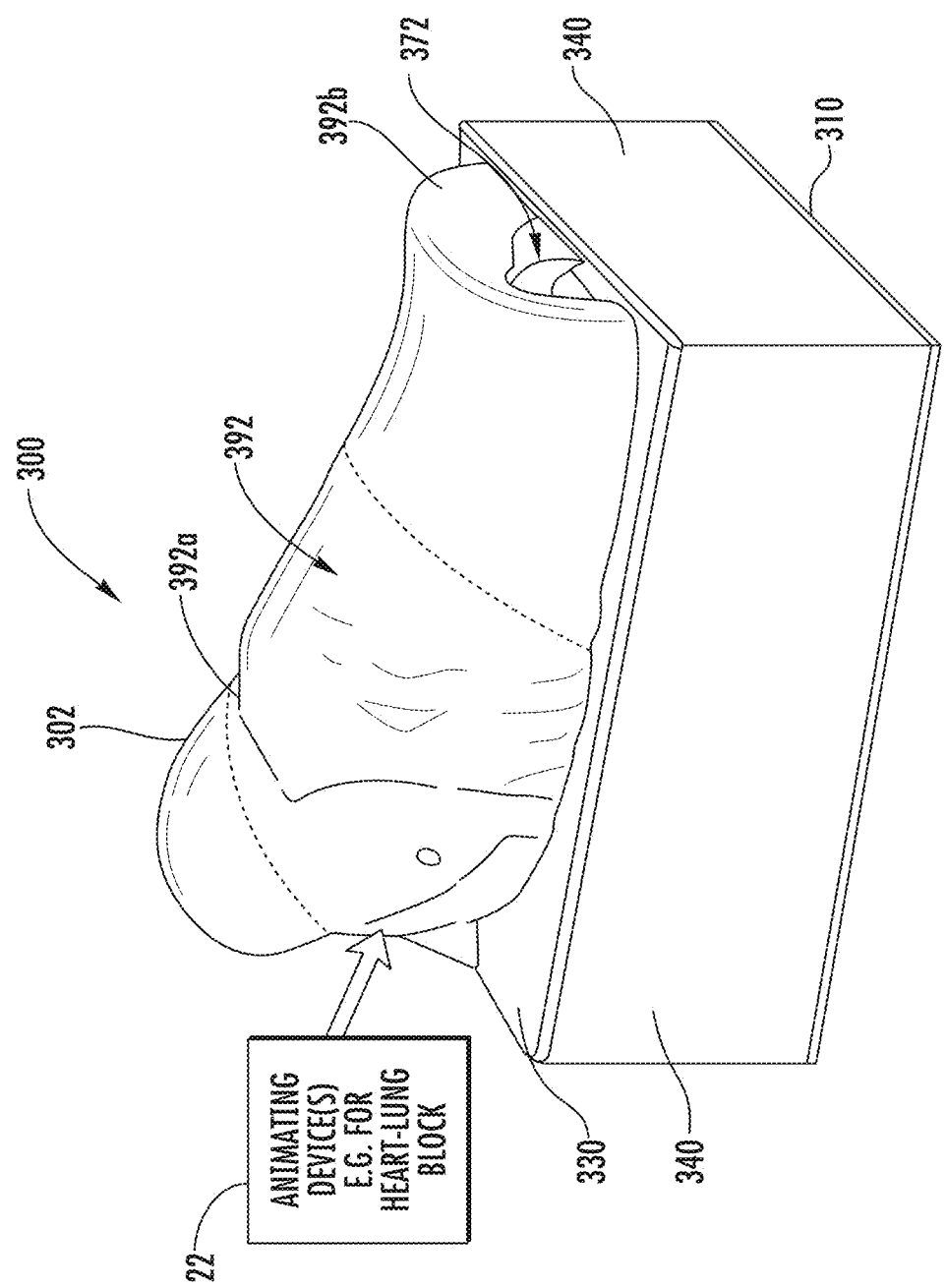
FIG. 20 is an isometric view of the surgical simulation device showing the side panels covering the support structure and the simulated skin over the simulated skeleton in accordance with a non-limiting example.
Figure 21:
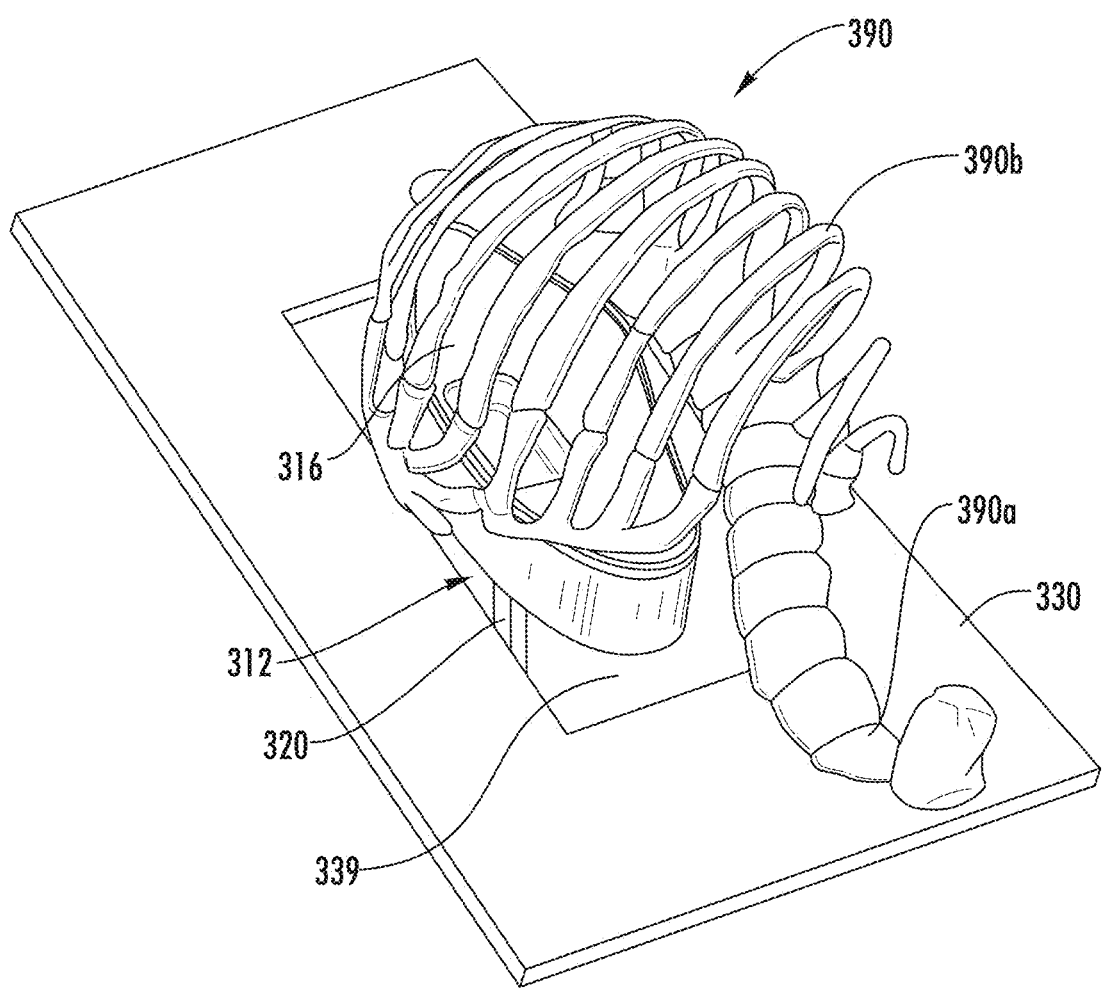
FIG. 21 is a isometric view showing the top plate, tissue tray and simulated human skeleton and rib cage in accordance with a non-limiting example.

Referring now to FIGS. 20 and 21, there is illustrated the surgical simulation device 302 that includes a simulated human skeleton 390 portion carried by the mannequin support structure 338, and more particularly, the top plate 330 of the mannequin support structure shown in FIGS. 11-19, and located above the animal tissue carried in the tissue tray 312 as better shown in FIG. 21. The mannequin support structure 338 in this example shows the four sides forming a side structure 340 as box with the bottom datum or support plate 310 supporting the internal components of the mannequin support structure and the pedestal 320 as better shown in FIGS. 11-19, which connects to the first sensor 324. The mannequin support structure 338 includes the top and bottom plates 330, 332 as noted before and connected to each other by the corner support posts 336 and supported on the datum or support plate 310 defining the datum reference by the second sensor 344 as illustrated in FIG. 11. A simulated skin 392 covers the simulated human skeleton rib cage 390 and includes a midsection of the thorax 392*a* and a lower spinal and pelvis area 392*b* (FIG. 20). As illustrated in FIG. 21, the simulated human skeleton rib cage 390 includes a spinal column 390*a* supported on the top plate 330 and ribs 390*b* connected to the spinal column.

Figure 22:
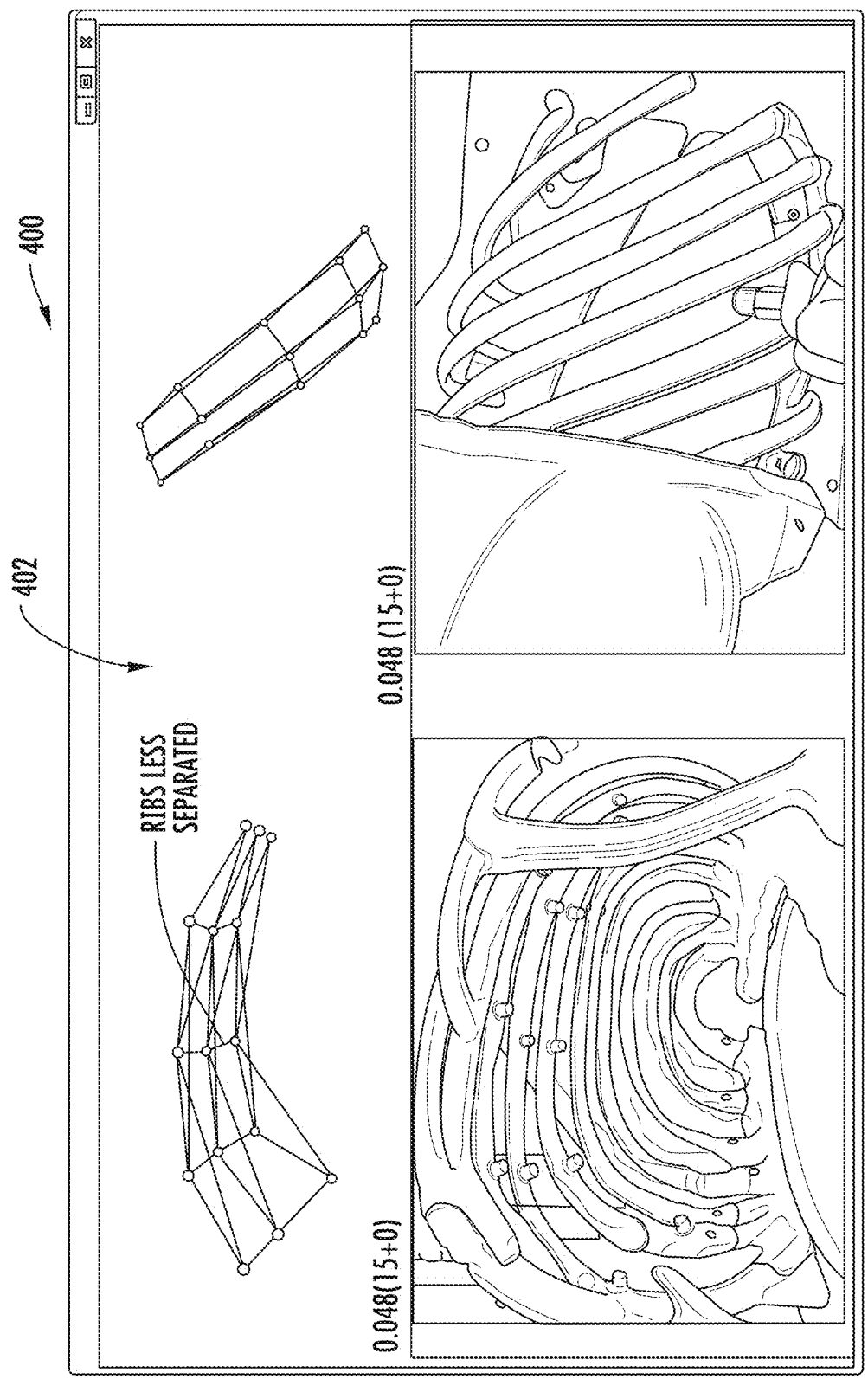
FIG. 22 is a screen shot showing an image of the inside of the rib cage, an outside view, and a three-dimensional wireframe model image based on the markers in accordance with a non-limiting example.

Referring now to FIG. 22, a screen shot 400 shown on the display 352 from the one or more portable computers 354 in this example shows the inside of the human skeleton portion and partially covered by the simulated human skin. The various markers as light emitting diodes 370 (LED's) in this example are shown positioned on the interior section of the ribs 390*b* forming the simulated human skeleton 310. An end of simulated robotic surgery tool 362 is shown inserted between the ribs 390*b*, although in this example, the robotic surgical tool is manually grasped and moved along the ribs as if in robotic surgery for purposes of illustration. The resulting three-dimensional wireframe model image 402 that is formed and imaged by the processor 350 is illustrated. In FIG. 22, the surgical tool 362 partially separates the ribs 390*b*, and in FIG. 23, the surgical tool is removed from that position. Two ribs 390*b* are now closer since the markers as LED's 370 are positioned closer to each other in this example with one rib farther away from the other rib.

Figure 23:
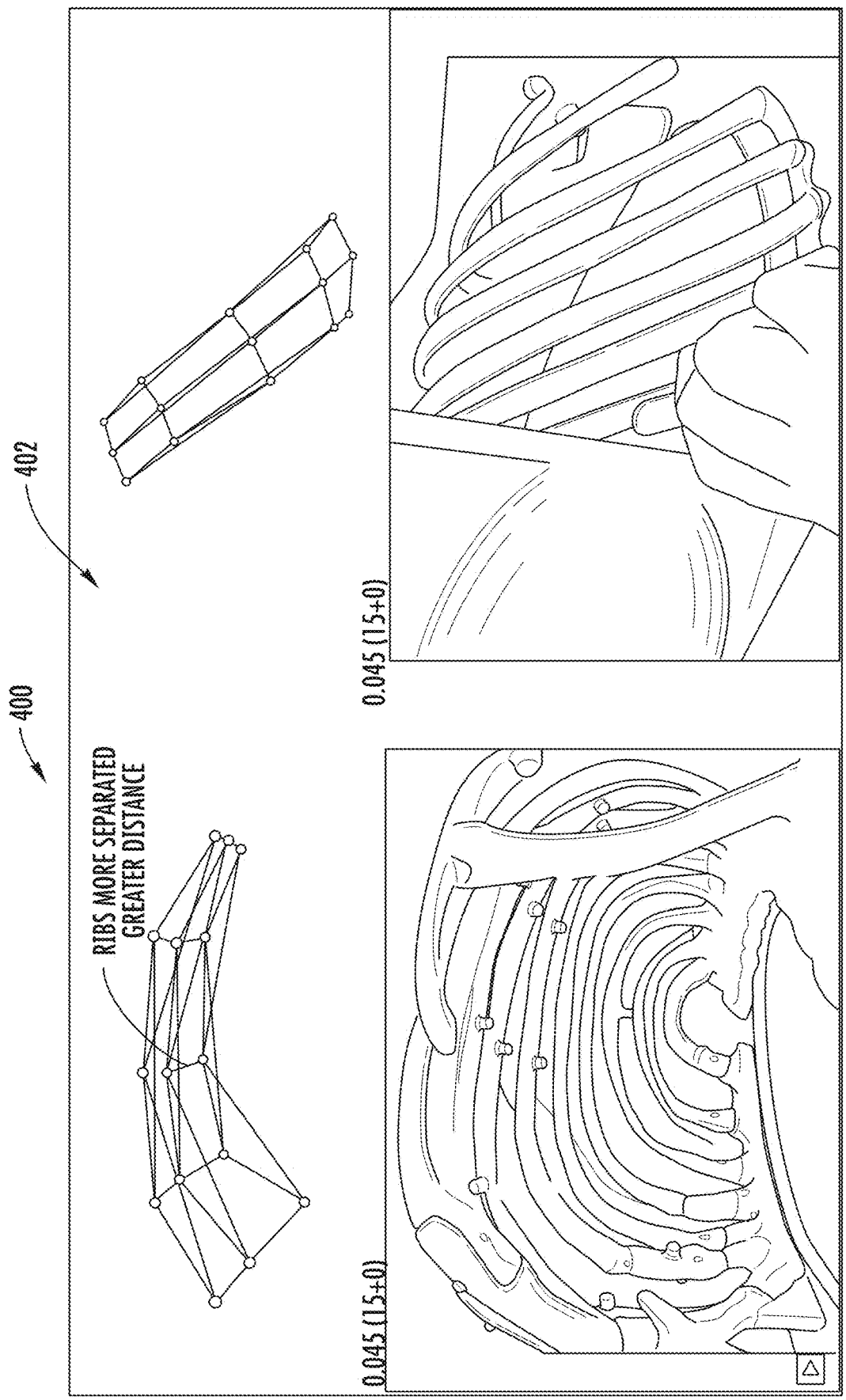
FIG. 23 is another screen shot similar to FIG. 22 but showing a slight deviation in the three-dimensional wireframe model image corresponding to a slight deviation in movement on a rib in accordance with a non-limiting example.

In a simulated surgery such as at a medical school, a camera could be positioned at one end of the simulated human skeletal portion 390 to show the inside of the body cavity 372 of the mannequin 302, which includes the simulated human skeleton portion 390 and simulated human skin 392, while an image on the right could be looking from the opposite side and inside the simulated human skeleton portion and a simulated human skin covering. In this example, the right-hand side image of FIGS. 22 and 23 shows manipulation of the surgical tool 362, illustrating how in actual training the robotic surgical tool may be inserted between the ribs 390*b* and effect displacement of the ribs and illustrate the forces generated by the surgical tool against the simulated human skeleton portion as part of the mannequin and also against any tissue that it may encounter.

Figure 24:
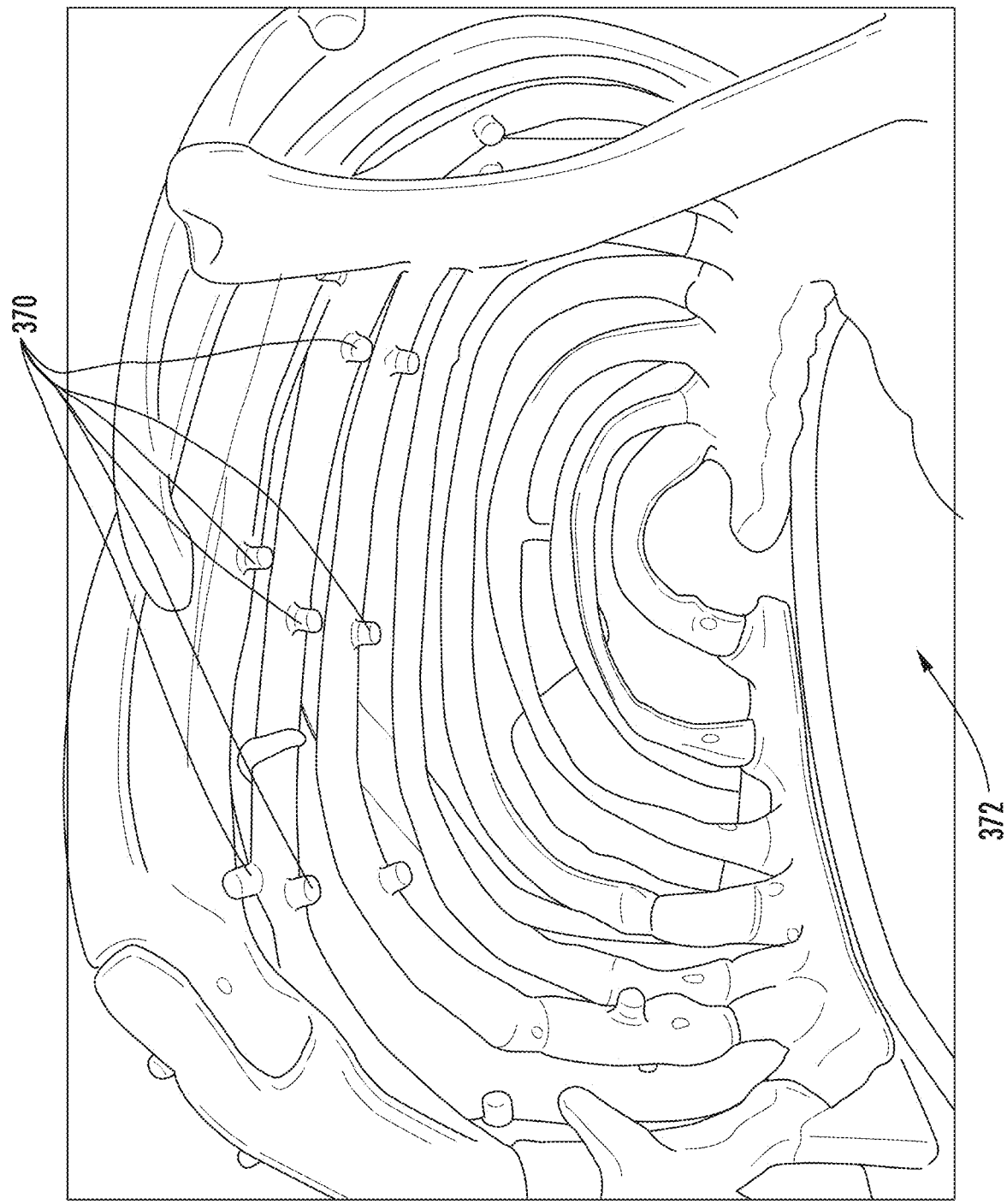
FIG. 24 is an enlarged view inside the rib cage shown in FIG. 22 and showing in detail the location of the markers in accordance with a non-limiting example.
Figure 25:
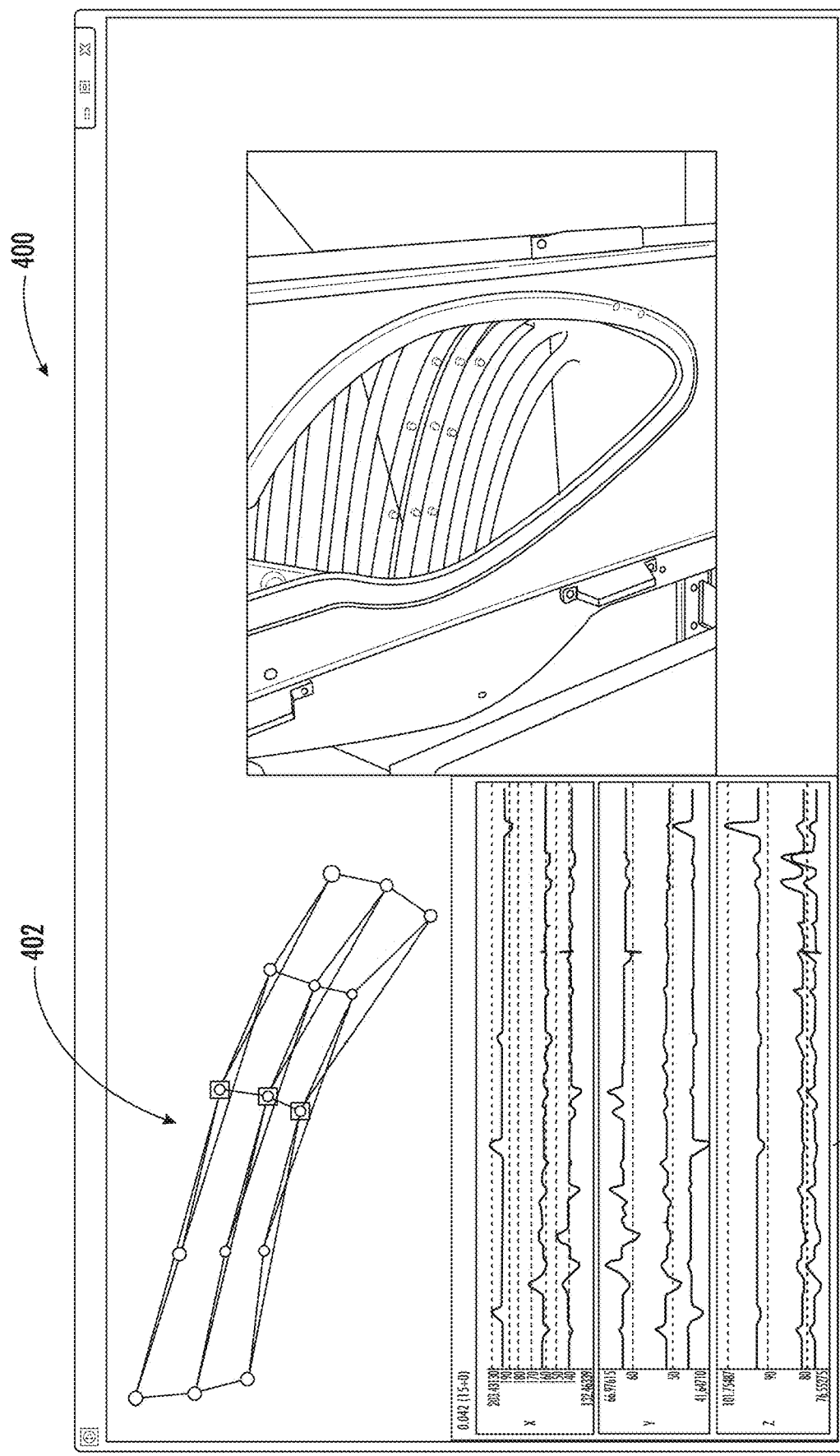
FIG. 25 is another screen shot showing an image from the camera of the rib cage, a three-dimensional wireframe model image and graph representing x, y and z in accordance with a non-limiting example.
Figure 26:
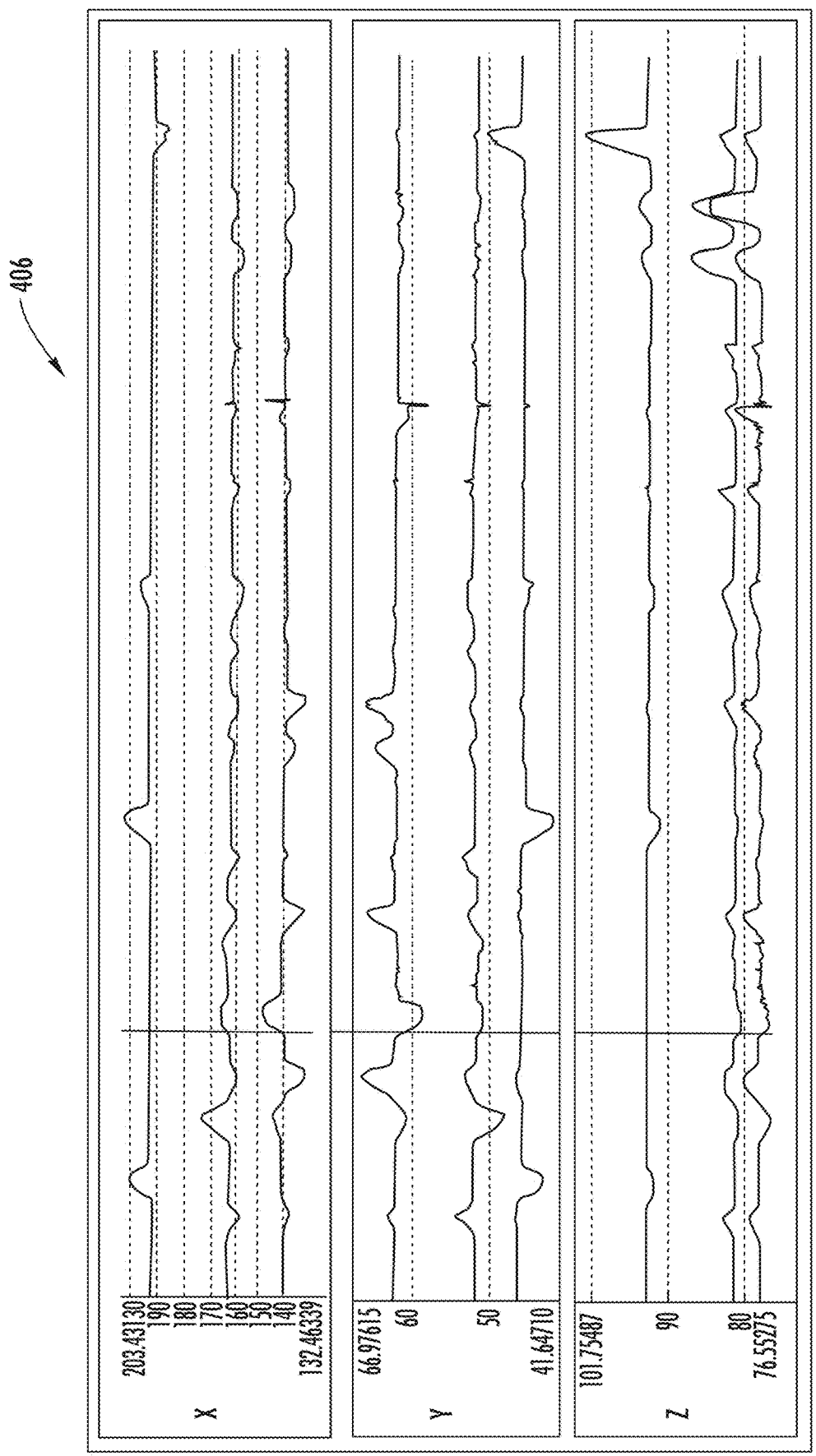
FIG. 26 is enlarged view of the graph shown in FIG. 25 in accordance with a non-limiting example.

Referring now to FIG. 24, an enlarged view of the left-hand drawing of FIG. 22 shows the inside of the simulated human skeleton portion 390 and a portion of the simulated human skin covering 392. FIG. 25 shows an example of the type of graph 406 that may be displayed based on the generated forces of the surgical tool 362 and may show any displacement by the surgery tool. The right-hand side image may show a portion of the simulated human skeleton portion. FIG. 26 is an enlarged view of the graph 406 of FIG. 25.

These figures illustrate the surgical simulation device 300 includes the mannequin support structure 338 and the top and bottom plates 330, 332 and the animal tissue carried by the tissue tray 312 and the simulated human skeleton portion 390 carried by the support structure above the animal tissue. The simulated human skin 392 covers the simulated human skeleton portion and markers such as LED's 370 are positioned on the ribs as illustrated, but also may be positioned on the animal tissue. The markers may be infrared or ultraviolet light emitting diodes that can be turned on and off at will and also used on tissue but could be other markers as explained above. The markers could be an optical fiber or passive reflectors.

The at least one camera such as the first video camera 304 is positioned to image the animal tissue and simulated human skeleton portion during surgeon training. The processor 350 operates as an image processor and is connected to the at least one camera and configured to receive images of the markers and form a three-dimensional wireframe model image 402 of the tissue and of the skeleton, and in the example shown in FIGS. 22 and 23, of the skeleton. The three-dimensional wireframe model image 402 as illustrated will change slightly as forces are generated by the surgical tool 362 during training and a video may be recorded via a three-dimensional video camera that includes a video recorder connected thereto. The memory 351 is coupled to the image processor 350 and stores the three-dimensional wireframe model images as they change during surgical training, for example, the changes that are shown in the three-dimensional wireframe model images in FIGS. 22 and 23. Even though the changes are slight, they show that forces are generated against one of the ribs.

In an example, the simulated human skeleton portion 390 includes a spinal column 390a and a rib cage 390b and the simulated human skin 392 includes an innermost layer and an outermost layer with the innermost layer protruding between ribs of the rib cage as better shown in FIG. 17. A simulated human diaphragm may be within the rib cage and the animal tissue may be a heart and lung block as explained in greater detail with reference to FIGS. 1-10, but could be other sections such as a colon area of lower abdominal section or other sections, such as the large intestine. At least one animating device 22 is coupled to the heart and lung block as shown in FIG. 20. The animal tissue in an example may be harvested porcine tissue, but in some examples, could be human cadaver tissue.

Referring now again to FIG. 16, the robotic surgery station 360 is adjacent the surgical simulation device 300 and includes at least one surgical tool 362 for surgical training. The tissue tray 312 as noted before may be formed as a disposable tray that is pre-loaded with the suitable animal-derived organs, such as a porcine heart and lung block. A pneumatically-actuated balloon may be inserted in the heart with no-drip connections to the arterial and venous vascularization. For example, IV bags may be filled with artificial (theater) blood and be attached to perfuse the heart/lung block. It is possible that the tissue tray 312 may be sealed in a vacuum bag to facilitate proper storage and handling. A 20-25% ethanol solution may be used as a preservative for the tray and tissue. A loaded and sealed tissue tray 312 may be referred to as a "cassette." Once the simulated surgical operation is complete, the tissue tray 312 with organs may be disposed. If surgery is to be restarted, a new cassette may be placed on the surgical simulation device 300.

The tissue tray 312 may include the lower portion as the indentation sized to receive organs and create an organ cavity. The tissue tray 312 may contain one or more graduated troughs for housing tubes and hoses, and channels for housing additional tubes and drainage channels with apertures (not shown). These hoses may be air hoses and tubes housed in the trough and channels to simulate a beating heart or blood flow through the simulated organs. The lower portion as the indentation may receive the heart and hold the heart in a position to simulate the relative location of the human heart with the mannequin.

In operation, the tubes and hoses may provide some combination of one or more pneumatic supply lines, one or more pressurized fluid supply lines, or optionally, one or more instrument communication buses. A plate may be positioned within a plate recess created by the tray to keep the hoses within the troughs and channels and it may cover the hoses before affixing the simulator organs to the tray. Thus, the tubes are concealed under the organs to create a more realistic surgical environment. The indentation in this example is designed for use with porcine organs, but may be designed for use in connection with other animal organs, including human cadaveric organs (as may be desired). An example of a modified tray is disclosed and commonly assigned U.S. Patent Publication No. 2017/0076636, the disclosure which is hereby incorporated by reference in its entirety.

Referring now again to FIG. 21, the simulated human skeleton 390 includes a portion of the human rib cage 390b, spinal column 390a and could include a pelvis portion and rest over the top plate 330 of the mannequin support structure forming the box as illustrated. The innermost layer of the simulated human skin 392 may be dyed to resemble the red muscles between the ribs 390b, and the outer layer may resemble one of several human skin colors. The simulated skin 392 may be molded so that the red layer protrudes slightly between the ribs 390b and locks into the rib cage, providing a realistic look when viewed from a vision systems such as first or second cameras 304, 306 placed within the thorax and showing the view as shown in FIG. 22 where a portion of the human skin covering is removed.

It should be understood that in the 81% of the US GDP that is not healthcare-related, there is a rapidly emerging convergence of commercially-available technologies that are broadly described as "Artificial Intelligence (AI)." New cars routinely are equipped with sensor suites that detect objects in blind spots, activate steering to maintain lane position and automatically apply brakes to avoid collisions. The step beyond this, where cars will assume complete control of their operation, is called "autonomous driving" and is being pursued by major automobile manufacturers.

The use of robots in factories is growing as is the exchange of information between the machines to facilitate significant increases in productivity. Factories are being designed to run continuously with minimal, if any, human intervention. This is sometimes referred to as "Industry 2.0."

In the government-regulated Healthcare field, implemented advances in automation and information sharing lag behind industry by years, if not decades. Since 2009, many electronic health care records have been mandated. Efforts to establish data interoperability have been discussed since the late 1990's, but most hospitals and operating rooms are only beginning to work off of common data networks in real time. There is significant change coming, however, particularly in the field of surgery.

Popular nomenclature regards traditional open surgery as Surgery 1.0. Laparoscopic or Minimally-Invasive Surgery (MIS) is considered Surgery 2.0 and the use of Robotic-Assisted Surgery Devices (RASD) is Surgery 3.0.

Surgery 4.0 is the integration of RASD and Artificial Intelligence. It will be driven by a wave of new RASD-makers coming into a market that has been dominated by Intuitive Surgical since 1999. The current $3 billion dollar market is expected to grow to over $20 billion by 2022 and Accenture is predicting that the value of Artificial Intelligence associated with RASD surgery will account for an additional $40 billion by 2026. There are emerging articles and press releases discussing the attributes of Surgery 4.0. A new working group has been formed by a team of surgeons, healthcare professionals and data scientists and they describe their new affiliated field as "Surgery Data Science."

RASD companies have hypothecated the features of Surgery 4.0-equipped RAS devices, such as autonomous suturing and warning signals when anatomical structures are in danger of being damaged. However, the animations and virtual reality displays seem to be skipping over the process of obtaining the data needed to provide such automated surgery assistance. This is noted in the literature as being the largest restraining factor in implementing Surgery 4.0.

An example system with the surgical simulation device 300 should be able to connect to a RAS device's hand control signals and endoscopic vision system and be able to determine, using Artificial Intelligence and Machine Learning principles, if the surgeon is operating safely. If the surgeon is not operating safely, then a "Surgeon's Third Eye" (STE) associated with the surgical simulation device 300 may issue a notification to the surgeon of the unsafe condition. The notification can be audible or visual or it may cause a "safety fault" and temporarily prevent the RASD from moving until the unsafe condition is resolved or the surgeon overrides the notification. It is envisioned that the STE would be licensed to the RASD maker and would either be a separate integrated hardware and software processing device or would be integrated into the design of the RAS device. It is anticipated that the STE would be licensed on a "per operation" basis to develop a recurring revenue stream and would also log all available data in a time-stamped manner to facilitate product improvement and to provide a reliable record of the operation.

Since the STE captures all available data of an operation, it would be able to keep a real time running accounting of stresses and strains imposed upon the patient that may lead to techniques that lessen post-operative pain and shorten recovery time. Such data would include the cumulative pressure and force exerted through the thoracic or abdominal wall and especially when RASD tools are placed in trocars between the ribs. This information would be available to the surgeon not as a safety fault, but rather as an indication of wear and tear on the patient as the surgery progressed.

The STE would be able to store data and compare the motion of the RASD tools and the patient's tissue in order to facilitate "Machine Learning (ML)" and "Deep Learning" algorithms, which can be used for instruction, certification or general assessment of a surgeon's skill when compared to normalized data of many surgeons performing the same operation with the same equipment. Recent literature (January 2017) suggests that there is no available method of creating the validation pathway to initiate the AI/ML data acquisition process.

The STE could exist in at least two versions. The first version could be FDA approved and there may not be a predicate device available for a substantial equivalence application, thus necessitating a Pre-Market Approval process for the device. The second version of the product could be focused on training and using real-tissue simulators such as those described above and may include operating on live animals and cadavers. This training system could have many more functions of tracking and guiding the learning process. It would not likely require FDA approval and could be used in conjunction with the telesimulation system as described above.

The STE could operate as follows:

a) Obtain patient data (gender, height, weight, age, disease state, BMI, etc.) during the pre-surgery diagnosis and preparation phase.

b) Also during the pre-surgery phase, obtain patient-specific high-resolution imagery taken from CT or MRI devices while the patient is positioned either normally in the image-gathering device or when the patient is positioned in the image-gathering device in the most likely position that the surgeon will choose to perform the operation (lateral, supine, Trendelenburg angles, etc.).

c) Prior to the operation, convert the patient imagery into a 3D model using Finite Element Analysis (FEA) techniques.

d) Prior to the operation, mathematically adjust (warp and stretch) a standard 3D FEA model of a statistically average human to the statistically average size and anatomy of a hypothetical patient with the same patient-specific data as found in (a) above.

e) Prior to the operation, combine the two FEA models and note the differences between the hypothetical patient model and the patient-specific model. They should be close and the steps in (d) and (e) should save considerable computer processing power.

f) Prior to the operation, using known FEA techniques, it is possible to refine, filter and locate all anatomical structures of interest to the surgeon in the patient specific model using the hypothetical model as a guide for locating these features. For example, it is possible to isolate the abdominal aorta from the patient imaging data (CT and MRI). There could be an initial volume rendering of the original imaging data and a contour is extracted from the imaging data from which the abdominal aorta is segmented. The medical axis and linear skeleton imagery may be extracted from which an initial control polyhedron and a final NURBS model is created.

g) During the operation, insert a second 3DHD endoscopic camera into the body cavity through an auxiliary port. This camera will feed a Motion Analysis™ system.

h) The surgeon will then suture or otherwise affix reflective markers at specific points in the anatomy.

i) The Motion Analysis™ endoscopic cameras are sensitive to 850 nm infrared light and this light and the reflectors are not visible to the normal surgeon's 3DHD endoscopic camera used for primary surgery.

j) The Motion Analysis™ endoscopic cameras may be positioned to see as wide a field of view as possible and will not be unnecessarily moved during surgery.

k) The wire frame Computer Assisted Design model produced by the Motion Analysis™ system may be warped, stretched and registered to the patient-specific model described in (f) above, thus synchronizing all of the FEA and optically-derived models.

l) The surgeon's hand control signals may be fed into the STE in real time and the intended positions of the tools will be known.

m) Based on a Rule Set (as obtained from the Data Initiation Process), the relationship of the tools, their entry points into the thorax or abdomen (or other surgical cavity) may be calculated. When tools become too close to anatomical features of interest, or another safety fault occurs, the STE may issue a signal that can be presented to the surgeon or cause the RASD to alter its behavior.

n) Other calculations may be performed, as described in the 2.0 Vision section, such as cumulative wear and tear on the intercostal spaces of the ribs due to the pivoting action of the RASD tool and trocar.

In order to have the STE approved by the FDA or other governmental regulator body, it will be necessary to trace the science of the STE back to a consistent simulation model that can generate hundreds of data sets with state-of-the-art repeatability.

The latest literature cites the lack of such consistent simulation models as a barrier to the development of Surgery 4.0.

This set of data, also referred to as the data patient, is suitable to provide a surgical platform whereby hundreds or thousands of identical operations can be performed by surgeons of varying skill and experience to establish an initial data set of hand control movement and tissue response which can be reduced to essential machine learning data by commercial techniques. This data patient described is not limited to thoracic models and the same basic layout and topology can be adapted readily to thoracic operations in the right lateral and supine position, as well as adapted to upper and lower abdominal procedures, and eventually, surgical procedures in all human anatomy.

It is possible to locate multiple data patients in surgery simulation facilities strategically located across the world to optimize for ease of accessibility, low communications latency, quality of service of the communication pathway, regulatory approval of working with ex-planted animal tissue and balancing of time zones with the location of surgeons requiring training. Access to these data patients will be made using the telesimulation technology as described above, offering low latency for operations that are imperceivably different from operations occurring in the same room as the surgeon's RASD console. The data arising from developing the learning set of operations may be used for development and improving the system. Because access to a real operation is made possible by the telesimulation system from nearly any location of a RASD control console, scaling the number of operations to several thousand events per procedure will be dramatically simpler than relocating surgeons to a central site.

Figure 27:
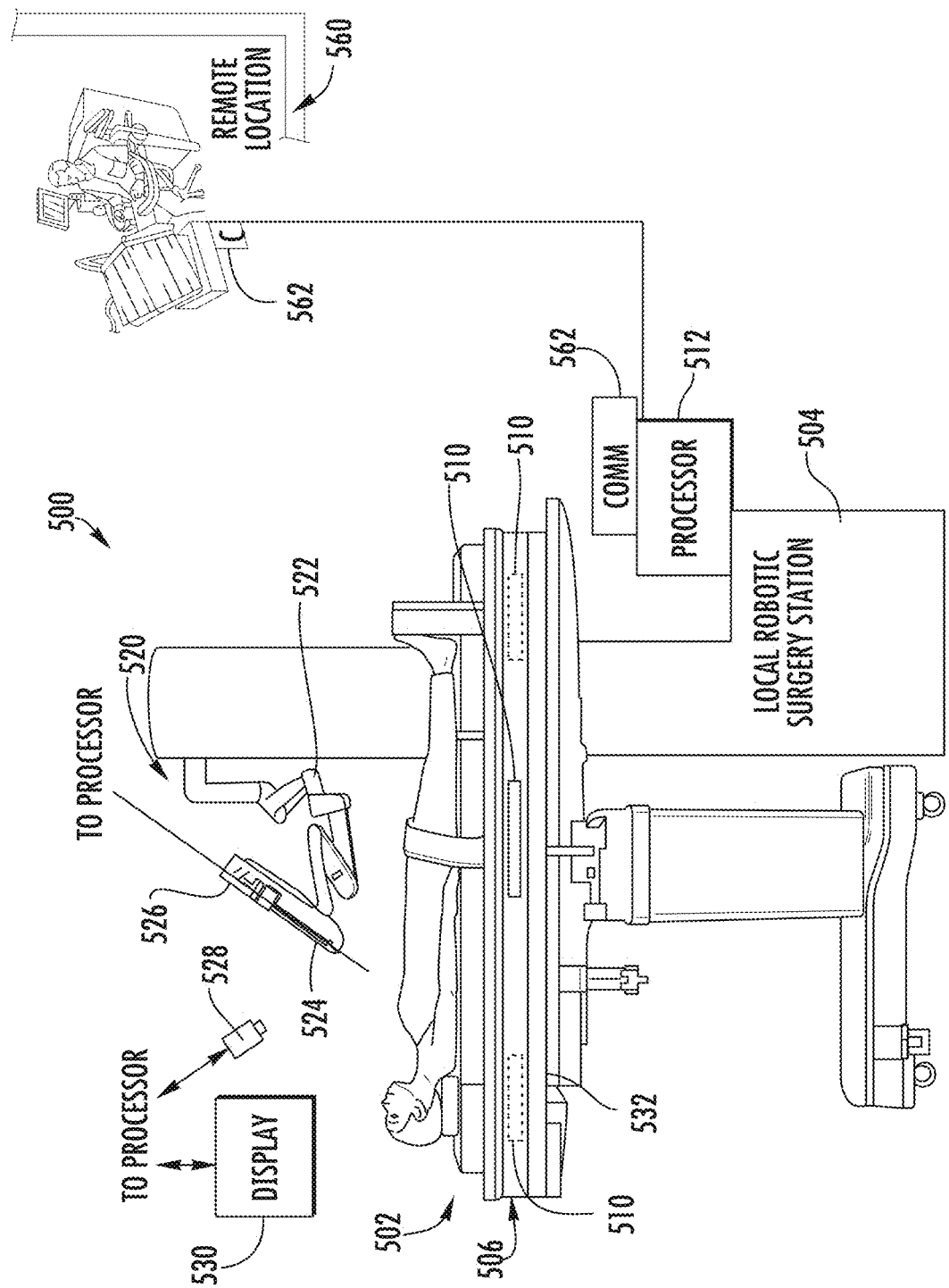
FIG. 27 is a fragmentary, block diagram of a robotic surgery system that senses at least one of force and torque experienced by the patient during robotic surgery.

The rule set, machine learning data, and the optical tracking and force/torque sensors, such as first and second sensors 324, 344 described above, may be applied to a robotic surgery system 500 that includes a local robotic surgery station configured to perform robotic surgery on a live patient such as shown in FIG. 27. As illustrated in this embodiment, an operating table 502 is adjacent the local robotic surgery station 504. The operating table 502 includes at least one patient support 506 configured to support the patient during robotic surgery and at least one patient force/torque sensor 510 coupled to the at least one patient support and configured to sense at least one of force and torque experienced by the patient during robotic surgery. In this example, a processor 512 is coupled to the at least one patient force/torque sensor 510 and configured to generate an alert indication when a threshold is exceeded, such as when excessive force is applied by a robotic surgery device 520 as part of the local robotic surgery station 504 and which includes a robotic surgery arm 522 and surgery tool 524 coupled thereto for performing the robotic surgery. As an example, excessive force may be generated on tissue near a blood vessel and an alarm alert may be generated indicative to the surgeon that the surgery tool 524 is applying excessive force on the tissue. As a result, the surgeon may "back off" and in some cases, the robot may halt surgical operation.

Thus, the processor 512, such as part of a networked larger computer or local computer or portable computer, may be configured to stop the local robotic surgery station 504 when that threshold is exceeded. In an example, the robotic surgery device 520 includes at least one robot force/torque sensor 526 coupled thereto and is configured to sense at least one of force and torque experienced by the robotic surgery device during robotic surgery. In this example, the robot force/torque sensor 526 may be coupled between the robotic surgery arm 522 and the surgery tool 524 as illustrated. At least one camera 528 may image the operating table and operation. The imagery from the camera 528 may be displayed on a suitable display 530 that is positioned for the surgeon trainee, robot operator, or other surgical aids may view.

Figure 29:
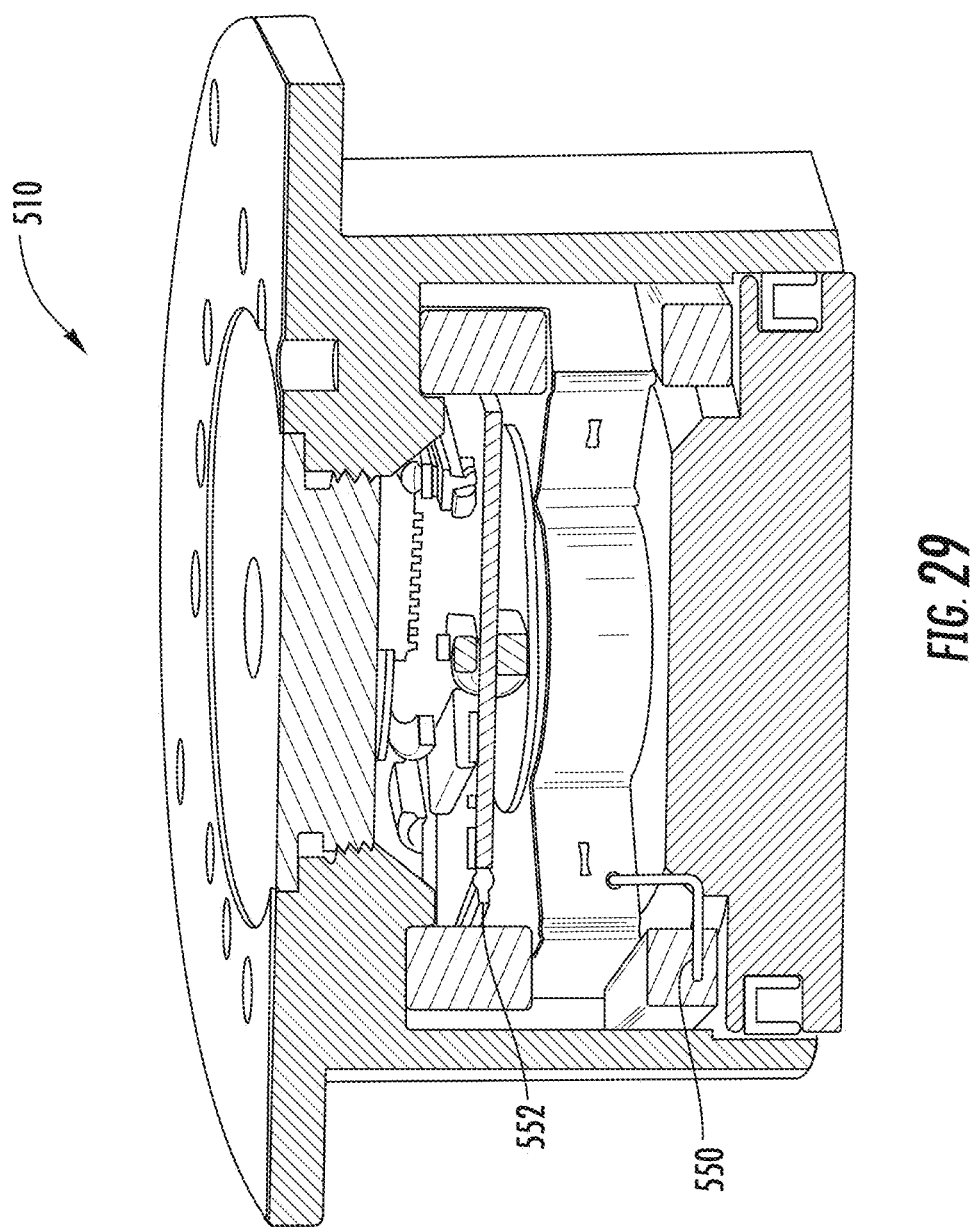
FIG. 29 is an example of a force/torque sensor used in the robotic surgery systems shown in FIGS. 27 and 28.

In the example shown in FIG. 27, the operating table 502 includes a frame 532. The at least one patient force/torque sensor 510 is coupled between the frame 532 and the at least one patient support 506 that includes straps or other connectors to help hold the patient steady during live operations. Although one force/torque sensor 510 is illustrated, other optional force/torque sensors as indicated by the dashed lines may be connected between the patient support 506 and the operating table frame 532. The force/torque sensors, in an example, output six components of force/torque. An example force/torque sensor 510 is shown in FIG. 29 and includes three sensor beams 550 that connect to circuitry 552 that outputs the six components of force/torque.

This example force/torque sensor 510 is also generally described above and is manufactured by ATI Industrial Automation. In this example, the processor 512, such as part of a larger networked computer or portable computer, may also record data so that a record is kept of each surgery and data records kept for each operation performed by a surgeon to produce a data set such as described above. As illustrated, a remote robotic surgery station 560 may be coupled to the local robotic surgery station 520 via a cable or other communications line, including wired or wireless connections, e.g., via internet, or other communications network and coupling the two stations via suitable communications modules 562 as described above. The remote robotic surgery station is configured in an example for use geographically remote from the local robotic surgery station.

The robotic surgery system 400 shown in FIG. 27 may sense multiple forces and torques exerted on the arms, tools and effectors of the surgical robot and its surgical arm 522 in contact with a patient, which could be a live human, cadaver or animal and process the collected data within the processor and compare that information to the output of one or more six-axis force/torque sensors 510 that are placed between the patient and the patient support 506 as the base of the operating table and operating table frame 532 to determine the amount of residual force applied from the robot to the patient that is passing through the patient's body and tissue.

Figure 28:
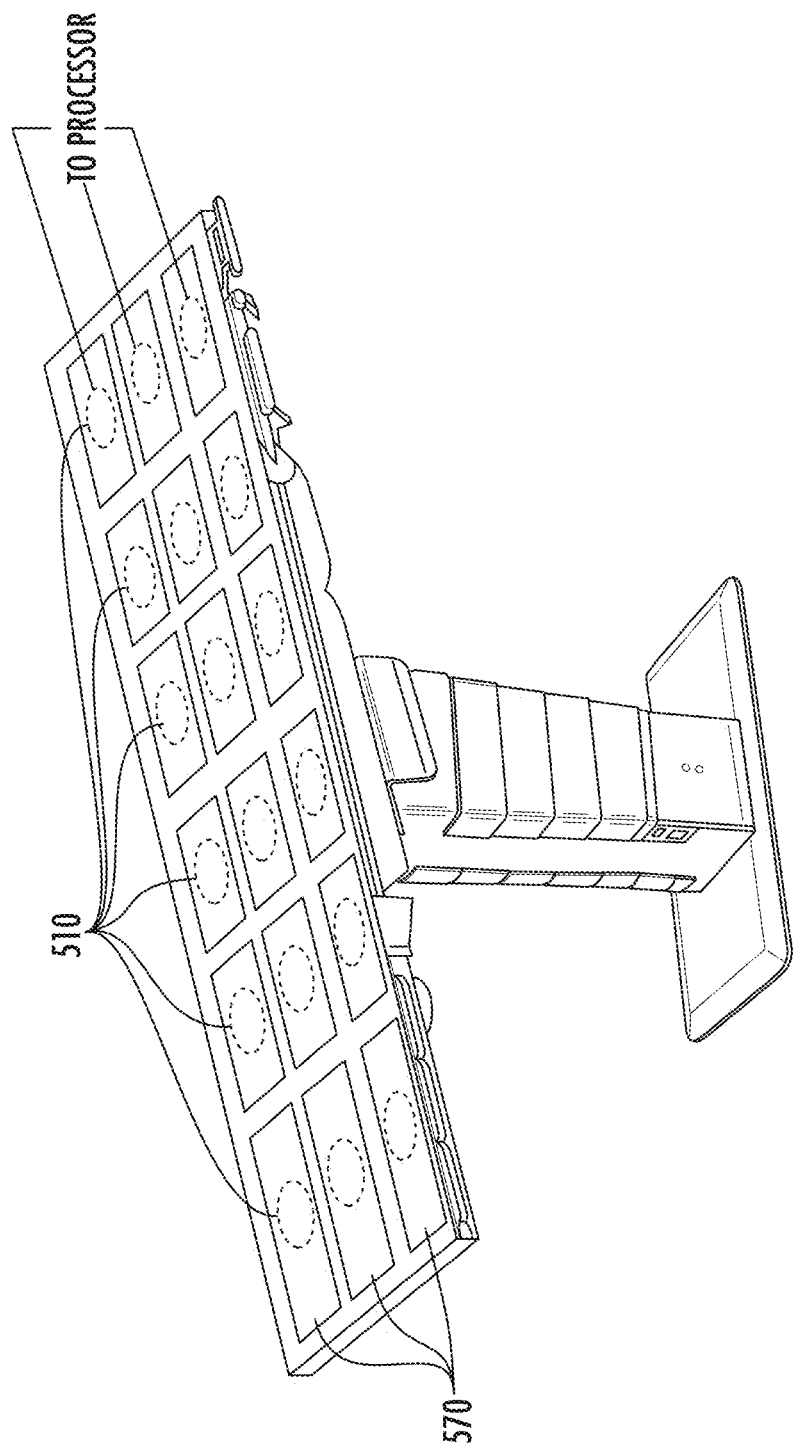
FIG. 28 is another example of a portion of the operating table in the robotic surgery system shown in FIG. 27.

Referring now to FIG. 28, the interface may include a set of rigid patient support plates 570 made of metal or non-metallic composite materials positioned between the patient and the operating table during surgery. There could be, as shown in FIG. 28, a plurality of segmented plates 570. The top plate or set of the plates 570 may be equipped with attachment points allowing the patient to be secured to the top plate or set of the plates by straps, tape, Velcro straps, or other means to immobilize the patient in the proper position for surgery. The operating table frame 532 may include a bottom plate or set of plates and may be separated from the top plate or set of plates 570 by one or more six-axis force/torque sensors 510, which detect, condition and amplify the forces and torques present between the top and bottom plates as the patient is moved by the surgical instruments during the live operation.

Designated pivot points can be used to cause the plate or plates 570 to move in such ways that the forces and torques can be further isolated and identified. For example, it is possible to use a large number of patient supports plates 570 each having a force/torque sensor between the patient support and the frame as shown in FIG. 28. By knowing the forces and torques that pass through the tissues and bodies of the patient when compared to those forces induced by the robot, many useful parameters may be calculated that would indicate manipulation, twisting, torqueing, bruising and even tearing of the body and tissues that could result in post-operative patient discomfort. By monitoring these forces in real-time, signals can be issued to the surgeon regarding the cumulative manipulation during the course of the operation and may give the surgeon timely indications to move trocars and tissue entry points or to adjust methods of surgery technique.

Figure 30:
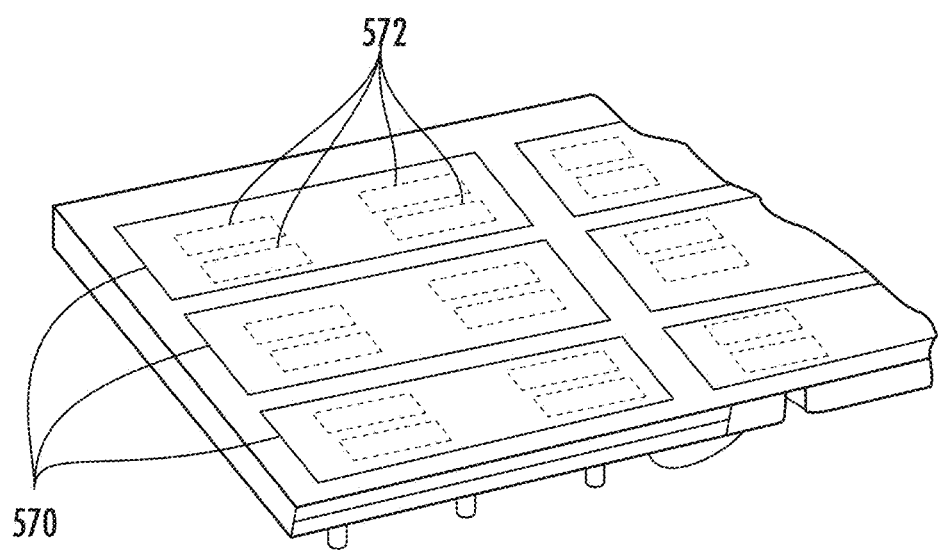
FIG. 30 is a fragmentary, isometric view of a portion of the operating table of FIG. 28 showing use of strain gauges.

It is also possible to include stain gauges 572 (FIG. 30) with circuitry output for the six components of force/torque. Thus, a sensor could individually be formed from a plurality of semiconductor stain gauges between a patient support 506 and frame 532.

Additionally, as haptics are introduced into surgical robots, there is a possibility that the haptic "feel" is generated between the movable portions of the end-effector tools, and the forces that are placed on the tissues and body of the patient from the shaft of the tool or trocar arm of the robot are not being properly measured. As a result, damage to the patient may occur away from the focal point of the operation. By comparing what forces and torques are generated into the patient from the surgical robot as the local robotic surgery station 504 and comparing those forces and torques to the residual forces that are transferred to the operating table 502, a set of desirable operating parameters may be calculated and used in the robotic surgery system and provide warning signals, safety "halts," and braking controls to avoid adverse events and conditions. In the example where the surgical tool 524 is generating excessive force on tissue near a blood vessel, the speed of the surgical tool may be slowed or even halted while audible or other warnings generated. Warning colors or other indicia could be generated on the display.

The robotic surgery system 400 shown in FIG. 28 using the plurality of segmented plates 520 as patient supports, each with a force/torque sensor, and connected to the common datum plane of the operating table frame 532, allows each patient support defined by a plate to become a data generator of the specific forces and torques generated at that location. Data would indicate where a particular force or torque is coming from and this would be valuable because it would lessen the need to have sensors inside a patient, which could be difficult to implement in many instances. In one example shown in the partial, isometric view of the operating table frame of FIG. 30, each force/torque sensor may be formed as a plurality of semiconductor strain gauges 572 with appropriate circuitry to generate an output of six components of force/torque that are then processed at the processor.

The segmented plates 520 as patient supports operate with respective force/torque sensors similar to a sensor array. The processor receives the pertinent force/torque signals and may determine where the excessive forces or torques are generated on tissue to pinpoint the location of a problem in a more precise manner.

During surgery, it is not only possible to generate an alert indication when a threshold is exceeded, but it is also possible to display the forces generated on the patient tissue so that the surgeon can view the forces in an image. For example, as the forces generated by the surgical tool against the patient increase, the colors on the display 530 at the area of surgery may change and increase from green (acceptable) to yellow and then red, indicating unacceptable forces being generated at the surgical site of the patient. This could be accomplished using an overlay to an image with the overlay imaging and processing techniques described above.

Figure 31:
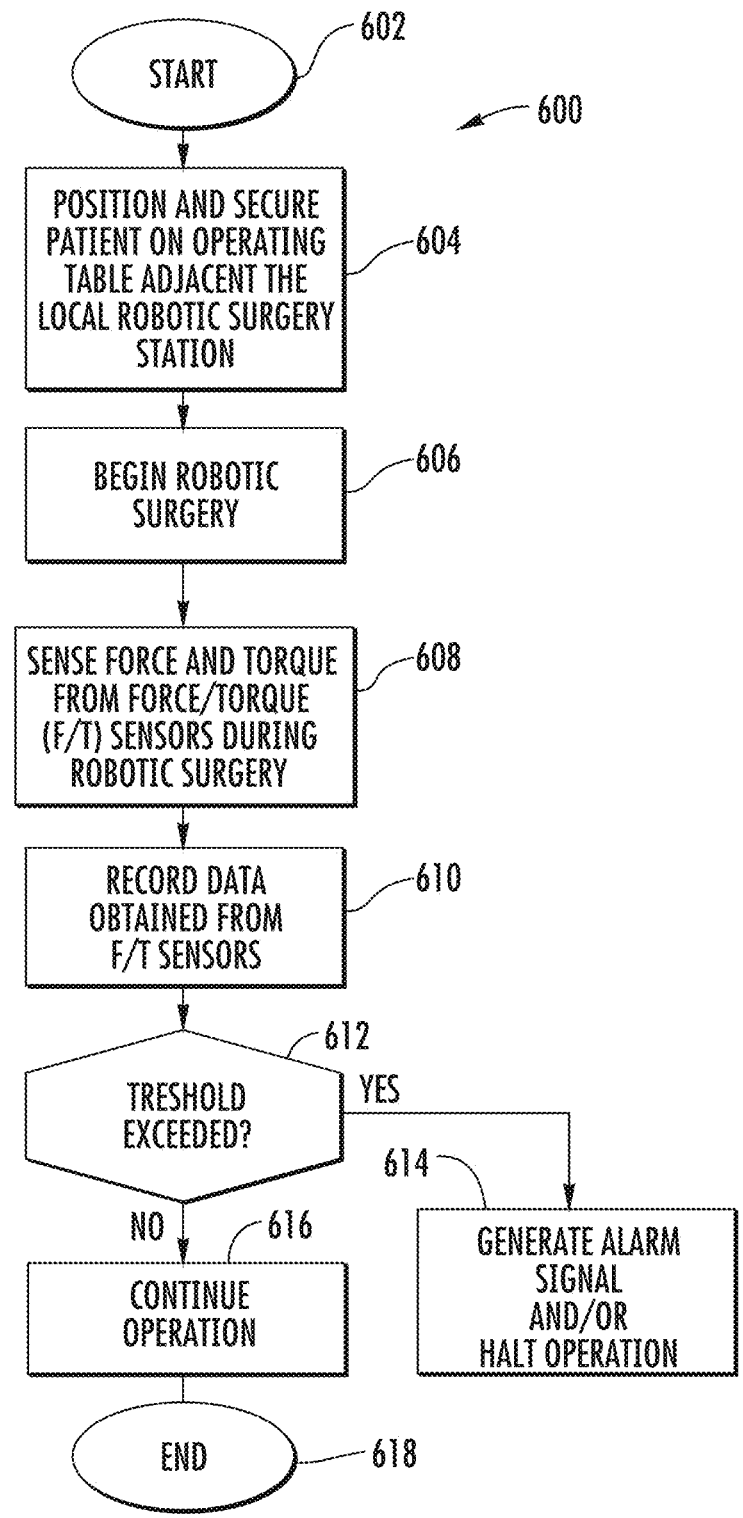
FIG. 31 is a flowchart illustrating a method of operating using the robotic surgery stations of FIGS. 27 and 28.

Referring now to FIG. 31, there is illustrated a flowchart generally at 600 showing a method of operating on a live patient using the robotic surgery stations described above. The process starts (Block 602) by positioning and securing a patient on an operating table adjacent the local robotic surgery station (Block 604). Robotic surgery begins (Block 606) and the system senses the force and torque in this example from the F/T sensors during robotics surgery (Block 608). The data generated from the F/T sensors is recorded (Block 610). During surgery, the system determines if a threshold is exceeded (Block 612) such as excessive force generated against tissue, and if yes, then the alarm signal may be generated and/or the operation halted (Block 614). If the threshold is not exceeded, the operation is continued (Block 616) and the process ends (Block 618).

Many modifications and other embodiments of the invention will come to the mind of one skilled in the art having the benefit of the teachings presented in the foregoing descriptions and the associated drawings. Therefore, it is understood that the invention is not to be limited to the specific embodiments disclosed, and that modifications and embodiments are intended to be included within the scope of the appended claims.

That which is claimed is:

1. A surgical simulation device comprising:
   a support plate defining a datum reference;
   a mannequin support structure carried by the support plate and comprising spaced, top and bottom interconnected plates, each of the top and bottom plates having a cut-out;
   a mannequin carried by the mannequin support structure on the top plate and having a body cavity corresponding to at least one of a thorax and abdomen;
   a pedestal connected to the support plate and extending upward through the cut-outs of top and bottom plates of the mannequin support structure;
   a tissue tray carried by the pedestal within the body cavity;
   animal tissue carried by the tissue tray;

a first sensor connected to the pedestal between the tissue tray and support plate and configured to sense force and torque exerted against the animal tissue from at least one surgical tool exerting force against the tissue during surgical training;

a second sensor connected between the bottom plate of the mannequin support structure and support plate and configured to sense force and torque exerted against the mannequin onto the support plate; and a processor connected to the first and second sensors and configured to determine the force exerted against respective areas of the animal tissue and mannequin during surgeon training.

2. The surgical simulation device according to claim 1, further comprising at least one camera connected to said processor, and markers positioned within the mannequin and on the animal tissue, wherein said processor is configured to receive video images and form a three-dimensional wireframe image of the body cavity and animal tissue.

3. The surgical simulation device according to claim 2, wherein said markers comprise one or more of light emitting diodes, an optical fiber, and passive reflectors.

4. A surgical simulation device comprising:

a mannequin support structure;

a tray carried by the mannequin support structure;

animal tissue carried by the tray;

a mannequin comprising simulated human skeleton portion that includes ribs carried by the mannequin support structure over the animal tissue and simulated human skin covering the simulated human skeleton portion;

markers comprising one or more of light emitting diodes, an optical fiber and passive reflectors positioned on the ribs and the animal tissue;

at least one camera positioned to image the animal tissue and simulated human skeleton portion during surgeon training; and an image processor connected to said at least one camera and configured to receive images of the markers and form a three-dimensional wireframe image of the tissue and the skeleton.

5. The surgical simulation device according to claim 4, further comprising a display connected to said image processor for displaying the three-dimensional wireframe image during surgical training.

6. The surgical simulation device according to claim 4, further comprising a video recorder connected to said at least one camera.

7. The surgical simulation device according to claim 4, further comprising a memory coupled to said image processor for storing the three-dimensional wireframe image and changes made to the wireframe image during surgical training.

8. The surgical simulation device according to claim 4, wherein the animal tissue comprises a heart and lung block and further comprising at least one animating device coupled to the heart and lung block.

9. The surgical simulation device according to claim 4, wherein the animal tissue comprises harvested porcine tissue or human cadaver tissue.

10. The surgical simulation device according to claim 4, further comprising a robotic surgery station adjacent said support structure and comprising at least one surgical tool.

\* \* \* \* \*